（12）United States Patent
Perna et al.

(10) Patent No.: US 10,425,814 B2
(45) Date of Patent: *Sep. 24, 2019

(54) CONTROL OF WIRELESS COMMUNICATION DEVICE CAPABILITY IN A MOBILE DEVICE WITH A BIOMETRIC KEY

(71) Applicant: Princeton Identity, Inc., Hamilton, NJ (US)

(72) Inventors: Steven N. Perna, Lawrenceville, NJ (US); Mark A. Clifton, Brick, NJ (US); Jongjin Kim, East Windsor, NJ (US); Bobby S. Varma, Princeton, NJ (US); Stephen J. Piro, Moorestown, NJ (US); Barry E. Mapen, Stonington, CT (US); Kevin P. Richards, Narragansett, RI (US); David Alan Ackerman, Hopewell, NJ (US); Ann-Marie Lanzillotto, Lawrenceville, NJ (US); David J. Wade, Stonington, CT (US); Timothy J. Davis, Columbus, NJ (US); Michael P. Fleisch, Manalapan, NJ (US); Jitendra J. Bhangley, Morganville, NJ (US); Glen J. Van Sant, Langhorne, PA (US)

(73) Assignee: Princeton Identity, Inc., Hamilton, NJ (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/514,098

(22) PCT Filed: Sep. 24, 2015

(86) PCT No.: PCT/US2015/051863
§ 371 (c)(1),
(2) Date: Mar. 24, 2017

(87) PCT Pub. No.: WO2016/049273
PCT Pub. Date: Mar. 31, 2016

(65) Prior Publication Data
US 2017/0251366 A1    Aug. 31, 2017

Related U.S. Application Data

(60) Provisional application No. 62/054,415, filed on Sep. 24, 2014.

(51) Int. Cl.
*H04W 12/06* (2009.01)
*G06F 21/32* (2013.01)
(Continued)

(52) U.S. Cl.
CPC .......... *H04W 12/06* (2013.01); *A61B 3/1216* (2013.01); *A61B 5/1171* (2016.02); *G06F 21/32* (2013.01);
(Continued)

(58) Field of Classification Search
CPC .......... G06F 21/32; G06F 21/31; G06F 21/10; G06F 21/83; H04W 12/06; H04L 63/08; H04L 63/0861; H04L 63/14; G06Q 20/322
See application file for complete search history.

(56) References Cited

U.S. PATENT DOCUMENTS 3,852,592 A   12/1974   Scoville et al.
3,993,888 A   11/1976   Fellman
(Continued)

FOREIGN PATENT DOCUMENTS

CN   102708357 A   10/2012
CN   103048848 A   4/2013
(Continued)

OTHER PUBLICATIONS

International Search Report dated Dec. 10, 2015, issued in connection with International Application No. PCT/US2015/051863 (1 page).
(Continued)

*Primary Examiner* — Khalil Naghdali
*Assistant Examiner* — Shaqueal D Wade
(74) *Attorney, Agent, or Firm* — McCarter & English, LLP

(57) ABSTRACT

An iris biometric recognition module includes technology for capturing images of an iris of an eye of a person, whether the person is moving or stationary. The iris biometric recognition technology can perform an iris matching procedure for, e.g., authentication or identity purposes, by comparing a digital iris image to a reference iris image and, if the
(Continued)

digital and reference iris images match, authenticating a person as authorized to access a first device and transmitting a wireless communication from the first device to a second device.

20 Claims, 24 Drawing Sheets

(51) Int. Cl.

| | |
|---|---|
| *G06F 21/83* | (2013.01) |
| *A61B 3/12* | (2006.01) |
| *A61B 5/1171* | (2016.01) |
| *H04L 29/06* | (2006.01) |
| *G06Q 20/10* | (2012.01) |
| *G07F 19/00* | (2006.01) |
| *G06Q 20/32* | (2012.01) |
| *G06Q 20/40* | (2012.01) |
| *H04W 12/08* | (2009.01) |
| *A61B 3/11* | (2006.01) |
| *A61B 5/117* | (2016.01) |
| *G06K 9/00* | (2006.01) |
| *G06K 9/20* | (2006.01) |
| *H04W 88/02* | (2009.01) |
| *G07C 9/00* | (2006.01) |
| *H04W 12/00* | (2009.01) |

(52) U.S. Cl.
CPC ......... *G06F 21/83* (2013.01); *G06Q 20/1085* (2013.01); *G06Q 20/322* (2013.01); *G06Q 20/40145* (2013.01); *G07F 19/20* (2013.01); *G07F 19/201* (2013.01); *H04L 63/0861* (2013.01); *A61B 3/112* (2013.01); *A61B 5/117* (2013.01); *G06K 9/00604* (2013.01); *G06K 9/2027* (2013.01); *G07C 9/00087* (2013.01); *H04W 12/00504* (2019.01); *H04W 12/08* (2013.01); *H04W 88/02* (2013.01)

(56) References Cited

U.S. PATENT DOCUMENTS

| | | | |
|---|---|---|---|
| 4,109,237 A | 8/1978 | Hill | |
| 4,641,349 A | 2/1987 | Flom et al. | |
| 5,291,560 A | 3/1994 | Daugman | |
| 5,337,104 A | 8/1994 | Smith et al. | |
| 5,481,622 A | 1/1996 | Gerhardt et al. | |
| 5,572,596 A | 11/1996 | Wildes et al. | |
| 5,835,616 A | 11/1998 | Lobo et al. | |
| 5,861,940 A | 1/1999 | Robinson et al. | |
| 5,933,515 A | 8/1999 | Pu et al. | |
| 5,953,440 A | 9/1999 | Zhang et al. | |
| 5,966,197 A | 10/1999 | Yee | |
| 5,987,459 A | 11/1999 | Swanson et al. | |
| 6,055,322 A | 4/2000 | Salganicoff et al. | |
| 6,081,607 A | 6/2000 | Mori et al. | |
| 6,119,096 A | 9/2000 | Mann et al. | |
| 6,144,754 A | 11/2000 | Okano et al. | |
| 6,204,858 B1 | 3/2001 | Gupta | |
| 6,229,907 B1 | 5/2001 | Okano et al. | |
| 6,247,813 B1 | 6/2001 | Kim et al. | |
| 6,252,976 B1 | 6/2001 | Schildkraut et al. | |
| 6,301,370 B1 | 10/2001 | Steffens et al. | |
| 6,307,954 B1 | 10/2001 | Suzaki | |
| 6,320,610 B1 | 11/2001 | Van Sant et al. | |
| 6,421,462 B1 | 7/2002 | Christian et al. | |
| 6,424,727 B1 | 7/2002 | Musgrave et al. | |
| 6,433,326 B1 | 8/2002 | Levine et al. | |
| 6,525,303 B1 | 2/2003 | Gladnick | |
| 6,526,160 B1 | 2/2003 | Ito | |
| 6,542,624 B1 | 4/2003 | Oda | |
| 6,549,644 B1 | 4/2003 | Yamamoto | |
| 6,614,919 B1 | 9/2003 | Suzaki et al. | |
| 6,714,665 B1 | 3/2004 | Hanna et al. | |
| 6,765,581 B2 | 7/2004 | Cheng | |
| 6,836,554 B1 | 12/2004 | Bolle et al. | |
| 6,850,252 B1 | 2/2005 | Hoffberg | |
| 6,895,103 B2 | 5/2005 | Chen et al. | |
| 6,912,298 B1 | 6/2005 | Wilensky | |
| 6,977,989 B2 | 12/2005 | Bothe et al. | |
| 7,015,955 B2 | 3/2006 | Funston et al. | |
| 7,095,901 B2 | 8/2006 | Lee et al. | |
| 7,099,495 B2 | 8/2006 | Kodno et al. | |
| 7,118,042 B2 | 10/2006 | Moore et al. | |
| 7,130,453 B2 | 10/2006 | Kondo et al. | |
| 7,146,027 B2 | 12/2006 | Kim et al. | |
| 7,295,686 B2 | 11/2007 | Wu | |
| 7,310,443 B1 | 12/2007 | Kris et al. | |
| 7,380,938 B2 | 6/2008 | Chmielewski, Jr. et al. | |
| 7,428,320 B2 | 9/2008 | Northcott et al. | |
| 7,466,308 B2 | 12/2008 | Dehlin | |
| 7,466,847 B2 | 12/2008 | Komura | |
| 7,542,628 B2 | 6/2009 | Lolacono et al. | |
| 7,574,021 B2 | 8/2009 | Matey | |
| 7,583,823 B2 | 9/2009 | Jones et al. | |
| 7,599,524 B2 | 10/2009 | Camus et al. | |
| 7,627,147 B2 | 12/2009 | Lolacono et al. | |
| 7,634,114 B2 | 12/2009 | Zappia | |
| 7,657,127 B2 | 2/2010 | Lolacono et al. | |
| 7,751,598 B2 | 7/2010 | Matey et al. | |
| 7,925,059 B2 | 4/2011 | Hoyos et al. | |
| 8,050,463 B2 | 11/2011 | Hamza | |
| 8,170,293 B2 | 5/2012 | Tosa et al. | |
| 8,189,879 B2 | 5/2012 | Cambier | |
| 8,195,576 B1 * | 6/2012 | Grigg | G06Q 20/20 380/229 |
| 8,200,980 B1 | 6/2012 | Robinson et al. | |
| 8,317,325 B2 | 11/2012 | Raguin et al. | |
| 8,337,104 B2 | 12/2012 | Takiguchi et al. | |
| 8,374,404 B2 | 2/2013 | Williams et al. | |
| 8,553,948 B2 | 10/2013 | Hanna | |
| 8,603,165 B2 | 12/2013 | Park | |
| 8,639,058 B2 | 1/2014 | Bergen et al. | |
| 8,682,073 B2 | 3/2014 | Bergen | |
| 8,755,607 B2 | 6/2014 | Bergen et al. | |
| 8,854,446 B2 | 10/2014 | Bergen et al. | |
| 8,934,005 B2 | 1/2015 | De Bruijn | |
| 9,100,825 B2 | 8/2015 | Schultz et al. | |
| 9,131,141 B2 | 9/2015 | Tinker et al. | |
| 9,195,890 B2 | 11/2015 | Bergen | |
| 9,514,365 B2 | 12/2016 | Tinker et al. | |
| 9,665,772 B2 | 5/2017 | Bergen | |
| 9,836,647 B2 | 12/2017 | Perna et al. | |
| 9,836,648 B2 | 12/2017 | Perna et al. | |
| 10,025,982 B2 | 7/2018 | Perna et al. | |
| 2002/0080141 A1 | 6/2002 | Imai et al. | |
| 2002/0118864 A1 | 8/2002 | Kondo et al. | |
| 2002/0150280 A1 | 10/2002 | Li | |
| 2002/0154794 A1 | 10/2002 | Cho | |
| 2002/0164054 A1 | 11/2002 | McCartney et al. | |
| 2002/0180586 A1 | 12/2002 | Kitson et al. | |
| 2003/0046553 A1 | 3/2003 | Angelo | |
| 2003/0103652 A1 | 6/2003 | Lee et al. | |
| 2003/0123711 A1 | 7/2003 | Kim et al. | |
| 2003/0169334 A1 | 9/2003 | Braithwaite et al. | |
| 2003/0174211 A1 | 9/2003 | Imaoka et al. | |
| 2004/0037452 A1 | 2/2004 | Shin | |
| 2004/0088584 A1 | 5/2004 | Shachar et al. | |
| 2004/0146187 A1 | 7/2004 | Jeng | |
| 2004/0170304 A1 | 9/2004 | Haven | |
| 2004/0213437 A1 | 10/2004 | Howard et al. | |
| 2004/0236549 A1 | 11/2004 | Dalton | |
| 2005/0047655 A1 | 3/2005 | Luo et al. | |
| 2005/0063582 A1 | 3/2005 | Park et al. | |
| 2005/0084179 A1 | 4/2005 | Hanna et al. | |
| 2005/0088200 A1 | 4/2005 | Takekuma et al. | |
| 2005/0210267 A1 | 9/2005 | Sugano et al. | |
| 2005/0270386 A1 | 12/2005 | Saitoh et al. | |
| 2006/0008125 A1 | 1/2006 | Lauper et al. | |
| 2006/0028617 A1 | 2/2006 | Matsumura et al. | |
| 2006/0098097 A1 | 5/2006 | Wach et al. | |

(56) References Cited

U.S. PATENT DOCUMENTS

| | | |
|---|---|---|
| 2006/0105806 A1 | 5/2006 | Vance et al. |
| 2006/0120570 A1 | 6/2006 | Azuma et al. |
| 2006/0140454 A1 | 6/2006 | Northcott et al. |
| 2006/0150928 A1 | 7/2006 | Lehmann et al. |
| 2006/0184243 A1 | 8/2006 | Yilmaz |
| 2006/0202036 A1 | 9/2006 | Wang et al. |
| 2006/0210123 A1 | 9/2006 | Kondo et al. |
| 2006/0222212 A1 | 10/2006 | Du et al. |
| 2006/0245623 A1 | 11/2006 | Loiacono et al. |
| 2006/0274918 A1 | 12/2006 | Amantea et al. |
| 2007/0014439 A1 | 1/2007 | Ando |
| 2007/0025598 A1 | 2/2007 | Kobayashi et al. |
| 2007/0036397 A1 | 2/2007 | Hamza |
| 2007/0047770 A1 | 3/2007 | Swope et al. |
| 2007/0140531 A1 | 6/2007 | Hamza |
| 2007/0160266 A1 | 7/2007 | Jones et al. |
| 2007/0189582 A1 | 8/2007 | Hamza et al. |
| 2007/0198850 A1 | 8/2007 | Martin et al. |
| 2007/0201728 A1 | 8/2007 | Monro |
| 2007/0206935 A1 | 9/2007 | Ono |
| 2007/0236567 A1 | 10/2007 | Pillman et al. |
| 2007/0285537 A1 | 12/2007 | Dwinell et al. |
| 2008/0049185 A1 | 2/2008 | Huffman et al. |
| 2008/0069411 A1 | 3/2008 | Friedman et al. |
| 2008/0121721 A1 | 5/2008 | Chen et al. |
| 2008/0180544 A1 | 7/2008 | Drader et al. |
| 2008/0187174 A1 | 8/2008 | Metaxas et al. |
| 2008/0219515 A1 | 9/2008 | Namgoong |
| 2008/0271116 A1 | 10/2008 | Robinson et al. |
| 2009/0041309 A1 | 2/2009 | Kim |
| 2009/0208064 A1 | 8/2009 | Cambier |
| 2009/0216606 A1 | 8/2009 | Coffman et al. |
| 2009/0220126 A1 | 9/2009 | Claret-Tournier et al. |
| 2009/0232418 A1 | 9/2009 | Lolacono et al. |
| 2009/0278922 A1 | 11/2009 | Tinker et al. |
| 2010/0026853 A1 | 2/2010 | Mokhnatyuk |
| 2010/0034529 A1 | 2/2010 | Jelinek |
| 2010/0046808 A1 | 2/2010 | Connell et al. |
| 2010/0063880 A1 | 3/2010 | Atsmon et al. |
| 2010/0082398 A1 | 4/2010 | Davis et al. |
| 2010/0142938 A1 | 6/2010 | Zhang |
| 2010/0176802 A1 | 7/2010 | Huguet |
| 2010/0278394 A1 | 11/2010 | Raguin et al. |
| 2010/0287053 A1 | 11/2010 | Ganong et al. |
| 2010/0290668 A1 | 11/2010 | Friedman et al. |
| 2010/0301113 A1 | 12/2010 | Bohn et al. |
| 2010/0310133 A1 | 12/2010 | Mason et al. |
| 2010/0328420 A1 | 12/2010 | Roman |
| 2011/0007205 A1 | 1/2011 | Lee |
| 2011/0043683 A1 | 2/2011 | Beach et al. |
| 2011/0075893 A1 | 3/2011 | Connel, II et al. |
| 2011/0081946 A1 | 4/2011 | Singh |
| 2011/0134268 A1 | 6/2011 | MacDonald |
| 2011/0142297 A1 | 6/2011 | Yu et al. |
| 2011/0187878 A1 | 8/2011 | Mor et al. |
| 2011/0317991 A1 | 12/2011 | Tsai |
| 2012/0086645 A1 | 4/2012 | Zheng et al. |
| 2012/0154536 A1 | 6/2012 | Stoker et al. |
| 2012/0155716 A1 | 6/2012 | Kim |
| 2012/0163783 A1 | 6/2012 | Braithwaite et al. |
| 2012/0243729 A1 | 9/2012 | Pasquero |
| 2012/0293642 A1 | 11/2012 | Berini et al. |
| 2013/0014153 A1 | 1/2013 | Bhatia et al. |
| 2013/0044199 A1 | 2/2013 | Nanu et al. |
| 2013/0051631 A1 | 2/2013 | Hanna |
| 2013/0081119 A1 | 3/2013 | Sampas |
| 2013/0083185 A1 | 4/2013 | Coleman, III |
| 2013/0089240 A1* | 4/2013 | Northcott ........... G06K 9/00604 382/117 |
| 2013/0091520 A1 | 4/2013 | Chen |
| 2013/0147603 A1 | 6/2013 | Malhas et al. |
| 2013/0150120 A1 | 6/2013 | Wu et al. |
| 2013/0162798 A1 | 6/2013 | Hanna et al. |
| 2013/0188943 A1 | 7/2013 | Wu |
| 2013/0194407 A1 | 8/2013 | Kim |
| 2013/0215228 A1 | 8/2013 | Stoker et al. |
| 2013/0250085 A1 | 9/2013 | MacKinnon |
| 2013/0329115 A1 | 12/2013 | Palmeri |
| 2014/0046772 A1 | 2/2014 | Raman |
| 2014/0055337 A1 | 2/2014 | Karlsson |
| 2014/0059607 A1 | 2/2014 | Upadhyay et al. |
| 2014/0071547 A1 | 3/2014 | O'Neill et al. |
| 2014/0078389 A1 | 3/2014 | Merz |
| 2014/0161325 A1 | 6/2014 | Bergen |
| 2014/0171150 A1 | 6/2014 | Hurst et al. |
| 2014/0232930 A1 | 8/2014 | Anderson |
| 2014/0327815 A1 | 11/2014 | Auger |
| 2014/0369575 A1 | 12/2014 | Riopka et al. |
| 2015/0037935 A1 | 2/2015 | Kim et al. |
| 2015/0098629 A1 | 4/2015 | Perna et al. |
| 2015/0098630 A1 | 4/2015 | Perna et al. |
| 2015/0126245 A1 | 5/2015 | Barkan et al. |
| 2015/0193666 A1 | 7/2015 | Derakhshani et al. |
| 2015/0227790 A1 | 8/2015 | Smits |
| 2015/0286864 A1 | 10/2015 | Gottemukkula et al. |
| 2015/0338915 A1 | 11/2015 | Publicover et al. |
| 2015/0379325 A1 | 12/2015 | Tinker et al. |
| 2016/0012275 A1 | 1/2016 | Bergen |
| 2016/0012292 A1 | 1/2016 | Perna et al. |
| 2016/0014121 A1 | 1/2016 | Perna et al. |
| 2016/0117544 A1 | 4/2016 | Hoyos et al. |
| 2016/0148384 A1 | 5/2016 | Bud et al. |
| 2016/0274660 A1 | 9/2016 | Publicover et al. |
| 2016/0345818 A1 | 12/2016 | Suzuki et al. |
| 2016/0364609 A1 | 12/2016 | Ivanisov et al. |
| 2017/0111568 A1 | 4/2017 | Hsieh et al. |
| 2017/0124314 A1 | 5/2017 | Laumea |
| 2017/0132399 A1 | 5/2017 | Pawluk et al. |
| 2017/0286790 A1 | 10/2017 | Mapen et al. |
| 2017/0286792 A1 | 10/2017 | Ackerman et al. |
| 2017/0323167 A1 | 11/2017 | Mapen et al. |
| 2017/0337439 A1 | 11/2017 | Ackerman et al. |
| 2017/0337440 A1 | 11/2017 | Green et al. |
| 2017/0337441 A1 | 11/2017 | Mapen et al. |
| 2017/0347000 A1 | 11/2017 | Perna et al. |
| 2018/0025244 A1 | 1/2018 | Bohl et al. |
| 2018/0165537 A1 | 6/2018 | Ackerman |

FOREIGN PATENT DOCUMENTS

| | | |
|---|---|---|
| CN | 103099624 A | 5/2013 |
| EP | 0821912 A2 | 2/1998 |
| EP | 1324259 A1 | 7/2003 |
| JP | 2007011667 A | 1/2007 |
| JP | 2008-538425 A | 10/2008 |
| JP | 4372321 B2 | 11/2009 |
| KR | 2003-0066512 A | 8/2003 |
| KR | 10-2011-0134848 A | 12/2011 |
| WO | WO-1996/19132 A1 | 6/1996 |
| WO | WO-1997/14873 A1 | 4/1997 |
| WO | WO-1997/21188 A1 | 6/1997 |
| WO | WO-1998/08439 A1 | 3/1998 |
| WO | WO-1999/31183 A1 | 6/1999 |
| WO | WO-2000/39760 A1 | 7/2000 |
| WO | WO-2013/056001 A1 | 4/2013 |
| WO | WO-2014/093227 A1 | 6/2014 |
| WO | WO-2014/100250 A2 | 6/2014 |
| WO | WO-2015/102704 A2 | 7/2015 |
| WO | WO-2017/172695 A1 | 10/2017 |
| WO | WO-2017/173228 A1 | 10/2017 |

OTHER PUBLICATIONS

Written Opinion of the International Searching Authority dated Dec. 10, 2015, issued in connection with International Application No. PCT/US2015/051863 (5 pages).

International Preliminary Report on Patentability dated Mar. 28, 2017, issued in connection with International Application No. PCT/US2015/051863 (6 pages).

Daugman (Daugman, J.), "High Confidence Visual Recognition of Persons by a Test of Statistical Independence," IEEE Transactions on Pattern Analysis and Machine Intelligence, 15 (11), pp. 1148-1161 (1993) (14 pages).

(56) References Cited

OTHER PUBLICATIONS

Monro (D. M. Monro and D. Zhang), "An Effective Human Iris Code with Low Complexity," Proc. IEEE International Conference on Image Processing, vol. 3, pp. 277-280 (Sep. 2005) (4 pages).
Tan (Tan et al), "Efficient Iris Recognition by Characterizing Key Local Variations," IEEE Transactions on Image Processing, vol. 13, No. 6 (Jun. 2004) (12 pages).
Annapoorani et al., Accurate and Fast Iris Segmentation. International Journal of Engineering Science and Technology. 2010;2(6):1492-1499.
Arfken, G., "Mathematical Methods for Physicists," Academic Press, NY 6.sup.th Ed. (2005).
Atos Origin, "UK Passport Service, Biometrics Enrollment Trial." Atos Origin Report (May 2005).
Bertalmio et al., Navier-Stokes, Fluid Dynamics, and Image and Video Inpainting. Proceedings of the 2001 IEEE Computer Society Conferenc on Computer Vision and Pattern Recognition. CVPR 2001, 8 pages, (2001).
Betke, et al., "Preliminary Investigation of Real-time Monitoring of a Driver in City Traffic," IEEE Intelligent Vehicles Syposium, Oct. 3-5, 2000, Dearborn, MI, 563-568.
Boehnen et al., A Multi-Sample Standoff Multimodal Biometric System, Theory, Aoolications and Systems (BTAS), Sep. 23, 2012, pp. 127-134.
Bowyer et al., Image Understanding for Iris Biometrics: A Survey. Computer Vision and Image Understanding. 2008;110:281-307.
Braithwaite, Michael et al., "Application-Specific Biometric Templates," AutoID 2002 Workshop, Tarrytown, NY, pp. 1-10 (2002).
Burt, et al., "The Laplacian Pyramid as a Compact Image Code," IEEE Transactions on Communications, 31(4): 532-540, 1983.
Canadian Offic Action for Application 2,833, 740 dated Jan. 15, 2018.
Office Action dated Sep. 26, 2018, issued in connection with U.S. Appl. No. 15/471,131 (15 pages).
Daugman John, "How Iris Recognition Works," IEEE Transactions on Circuits and Systems for Video Teohnology, vol. 14, No. 1 (Jan. 2004).
Daugman, J., "Recognizing Persons by Their Iris Patterns," in Biometrics: Personal Indentification in a Networked Society, A.K. Jain, et al., eds. Kluwer Academic Pub. 1999.
Daugman, John et al., "Iris recognition border-crossing system in the UAE," International Airport Review, Issue 2 (2004).
Daugman, John."How Iris Recognition Works".Jun. 13, 2003. IEEE Transactions on Circuits and Systems for Video technology, vol. 14, No. 1.
Daugman, The Importance of Being Random: Statistical Principles of Iris Recognition. Pattern Recognition. Pre-publication version. 13 pages, Dec. 21, 2001.
DellaVecchia, et al., "Methodology and apparatus for using the human iris as a robust biometric," Ophthalmic Technologies VIII, SPIE Biomedical Optics Society, Photonics West Conference, San Jose, CA Jan. 24, 1998.
Du et al., Analysis of Partial Iris Recognition Using a 1-D Approach. Proceedings, IEEE International Conference on Acoustics, Speech, and Signal Processing. Mar. 18-23, 2005;2;961-964.
European Office Action for Application 12719332.4 dated Jan. 29, 2018.
European Search Report for Apllication 14876521.7 dated Oct. 19, 2017.
Extended European Search Report in connection with European Patent Application No. 15864635.6 dated Jun. 6, 2018 (8 pages).
Fan, et al., "An Efficient Automatic Iris Image Acquisition and Preprocessing System," Proceedings of the 2006 IEEE International Conference on Mechatronics and Automation, pp. 1779-1784 (6 pages).
Final Office Action dated Aug. 18, 2016 from U.S. Appl. No. 14/858,715, filed Sep. 18, 2015 (6 pages).
Final Office Action dated Aug. 4, 2016 from U.S. Appl. No. 14/509,366, filed Oct. 8, 2014 (24 pages).
Final Office Action dated Mar. 21, 2017 from U.S. Appl. No. 14/863,936, filed Sep. 24, 2015 (17 pages).
Final Office Action dated Mar. 22, 2017 from U.S. Appl. No. 14/863,950, filed Sep. 24, 2015 (16 pages).
Final Office Action dated Mar. 22, 2017 from U.S. Appl. No. 14/863,960, filed Sep. 24, 2015 (21 pages).
Final Office Action for U.S. Appl. No. 10/818,307, dated Jan. 21, 2009, 28 pages.
Final Office Action for U.S. Appl. No. 10/818,307, dated Jan. 30, 2008, 19 pages.
Final Office Action for U.S. Appl. No. 11/377,042, dated Nov. 14, 2008, 20 pages.
Final Office Action for U.S. Appl. No. 11/510,197, dated May 5, 2009, 16 pages.
Final Office Action for U.S. Appl. No. 12/464,369, dated Aug. 5, 2014, 22 pages.
Final Office Action for U.S. Appl. No. 12/464,369, dated Oct. 3, 2012, 27 pages.
Final Office Action for U.S. Appl. No. 12/576,644, dated Oct. 13, 2010, 11 pages.
Final Office Action for U.S. Appl. No. 14/100,615, dated Sep. 1, 2015, 22 pages.
Final Office Action for U.S. Appl. No. 14/509,356, dated Sep. 28, 2016, 20 pages.
Final Office Action for U.S. Appl. No. 14/509,366, dated Aug. 4, 2016, 29 pages.
Final Office Action for U.S. Appl. No. 14/846,090, dated Jun. 15, 2016, 17 pages.
Final Office Action for U.S. Appl. No. 14/858,715, dated Aug. 18, 2016, 29 pages.
Final Office Action for U.S. Appl. No. 14/858,715, dated Aug. 18, 2016, 6 pages.
Final Office Action for U.S. Appl. No. 14/863,936, dated Mar. 21, 2017, 17 pages.
Final Office Action for U.S. Appl. No. 14/863,950, dated Mar. 22, 2017, 16 pages.
Final Office Action for U.S. Appl. No. 14/863,960, dated Mar. 22, 2017, 21 pages.
First Japanese Office Action for Application 2015-545911 dated Feb. 26, 2018 ( with English translation).
FIT Validation Studies, http://www.pmifit.com/validation.htm, Mar. 2, 2004.
Google Scholar Search—"Rida Hadma" pp. 1 of 2.
Haro, et al., "Detecting and Tracking Eyes by Using Their Physiological Properties, Dynamics and Appearance," CVPR 2000, 163-168.
Hutchinson, et al., "Human-Computer Interaction Using Eye-Gaze Input," IEEE Transaction on Systems, Man and Cybernetics, 19(6): 1527-1534, 1989.
International Biometrics Group, "Independent Testing of Iris Recognition Technology, Final Report," Study Commissioned by the US Department of Homeland Security (May 2005).
International Search Report and Written Opinion for Application No. PCT/US17/13110, dated May 18, 2017, 12 pages.
International Search Report and Written Opinion for Application No. PCT/US17/24444, dated Jun. 19, 2017, 9 pages.
International Search Report and Written Opinion for Application No. PCT/US2013/073887, dated Mar. 20, 2014, 11 pages.
International Search Report and Written Opinion for Application No. PCT/US2017/025303, dated Jun. 16, 2017, 11 pages.
International Search Report and Written Opinion for PCT/US2017/24444 dated Jun. 19, 2017 pp. 1-15.
International Search Report and Written Opinion for PCT/US2018/042807, dated Sep. 27, 2018, pp. 1-19.
International Search Report and Written Opinionf for PCT/US2017/025303 dated Jun. 16, 2017.
International Search Report for Application No. PCT/US2017/065793, dated Feb. 16, 2018, 3 pages.
International Search Report for PCT/US2015061024, dated Mar. 31, 2016.
International Search Report of the International Searching Authority dated Jun. 28, 2018, issued in connection with International Application No. PCT/US2018/025895 (3 pages).

(56) References Cited

OTHER PUBLICATIONS

Iwai, Daisuke, Shoichiro Mihara, and Kosuke Sato. "Extended depth-of-field projector by fast focal sweep projection." IEEE transactions on visualization and computer graphics 21.4 (2015): 462-470.
Jacob, R., "The Use of Eye Movements in Human-Computer Interaction Techniques: What you Look At is What you Get," ACM Trans. Info.Sys., 9(3):152-169.
Japanese Office Action for Application No. 2015-545911, dated Feb. 20, 2018, 6 pages.
Li, Zexi, "An Iris Recognition Algorithm Based on Coarse and Fine Location," 2017 IEEE 2nd International Conference on Big Data Analysis, pp. 744-747 (4 pages).
Ma et al., "Efficient Iris Recognition by Characterizing Key Local Variations", IEEE Transactions on Image Processing, vol. 13, No. 6, Jun. 2004, 12 pages.
Ma., et al. "Iris Recognition Using Circular Symmetric Filters," Pattern Recognition, 2002, Proceedings 16th International Conference on vol. 2 IEEE, 2002 (4 pages).
Ma., et al., "Iris Recognition Based on Multichannel Gabor Filtering" ACCV2002: The 5th Asian Conference on Computer Vision, Jan. 23-25, 2002, Melbourne, Australia (5 pages).
Mansfield, Tony et al., "Biometric Product Testing Final Report," CESG Contract X92A/4009309, CESG/BWG Biometric Test Programme; Centre for Mathematics & Scientific Computing, National Physical Laboratory (2001).
Matey et al., Iris on the Move: Acquisition of Images for Iris Recognition in Less Constrained Environments. Proceedings of the IEEE. Nov. 2006;94(11):1936-1947.
Miyazawa et al., Iris Recognition Algorithm Based on Phase-Only Correlation, The Institute of Image Information and Television Engineers, JapanJun. 27, 2006, vol. 30, No. 33, pp. 45-48.
Narayanswamy, et al., "Extended Depth-of-Field Iris Recognition System for a Workstation Environment," Proc. SPIE. vol. 5779 (2005) (10 pages).
Negin, et al., "An Iris Biometric System for Public and Personal Use," IEEE Computer, pp. 7075, Feb. 2000.
Nguyen, et al., "Quality-Driven Super-Resolution for Less Constrained Iris Recognition at a Distance and on the Move," IEEE Transactions on Information Forensics and Security 6.4 (2011) pp. 1248-1558 (11 pages).
Non-Final Office Action for U.S. Appl. No. 10/809,471, dated Mar. 19, 2007, 12 pages.
Non-Final Office Action for U.S. Appl. No. 10/818,307, dated Jul. 10, 2008, 28 pages.
Non-Final Office Action for U.S. Appl. No. 10/818,307, dated Mar. 20, 2007, 22 pages.
Non-Final Office Action for U.S. Appl. No. 11/334,968, dated Jan. 6, 2009, 28 pages.
Non-Final Office Action for U.S. Appl. No. 11/377,042, dated Apr. 8, 2009, 22 pages.
Non-Final Office Action for U.S. Appl. No. 11/377,042, dated Jan. 7, 2008, 13 pages.
Non-Final Office Action for U.S. Appl. No. 11/510,197, dated Oct. 10, 2008, 36 pages.
Non-Final Office Action for U.S. Appl. No. 11/510,197, dated Oct. 8, 2009, 21 pages.
Non-Final Office Action for U.S. Appl. No. 11/849,969, dated Dec. 19, 2008, 17 pages.
Non-Final Office Action for U.S. Appl. No. 11/857,432, dated Dec. 30, 2008, 23 pages.
Non-Final Office Action for U.S. Appl. No. 12/429,695, dated Sep. 2, 2009, 11 pages.
Non-Final Office Action for U.S. Appl. No. 12/464,369, dated Jan. 2, 2015, 23 pages.
Non-Final Office Action for U.S. Appl. No. 12/464,369, dated May 9, 2012, 33 pages.
Non-Final Office Action for U.S. Appl. No. 12/576,644, dated Jul. 14, 2010, 14 pages.
Non-Final Office Action for U.S. Appl. No. 13/096,716, dated May 23, 2013, 16 pages.
Non-Final Office Action for U.S. Appl. No. 13/096,724, dated Jan. 16, 2014, 29 pages.
Non-Final Office Action for U.S. Appl. No. 13/096,728, dated May 7, 2013, 33 pages.
Non-Final Office Action for U.S. Appl. No. 13/096,728, dated Nov. 8, 2012, 37 pages.
Non-Final Office Action for U.S. Appl. No. 14/100,615, dated Mar. 4, 2015, 19 pages.
Non-Final Office Action for U.S. Appl. No. 14/509,356, dated Feb. 29, 2016, 19 pages.
Non-Final Office Action for U.S. Appl. No. 14/509,356, dated Mar. 16, 2017, 21 pages.
Non-Final Office Action for U.S. Appl. No. 14/509,366, dated Feb. 21, 2017, 25 pages.
Non-Final Office Action for U.S. Appl. No. 14/509,366, dated Mar. 3, 2016, 40 pages.
Non-Final Office Action for U.S. Appl. No. 14/846,090, dated Jan. 7, 2016, 35 pages.
Non-Final Office Action for U.S. Appl. No. 14/858,715, dated Mar. 14, 2016, 37 pages.
Non-Final Office Action for U.S. Appl. No. 14/863,936, dated Aug. 4, 2016, 16 pages.
Non-Final Office Action for U.S. Appl. No. 14/863,936, dated Sep. 26, 2017, 28 pages.
Non-Final Office Action for U.S. Appl. No. 14/863,950, dated Aug. 3, 2016, 15 pages.
Non-Final Office Action for U.S. Appl. No. 14/863,950, dated Sep. 26, 2017, 22 pages.
Non-Final Office Action for U.S. Appl. No. 14/863,960, dated Aug. 3, 2016, 21 pages.
Non-Final Office Action for U.S. Appl. No. 14/863,960, dated Sep. 28, 2017, 28 pages.
Non-Final Office Action for U.S. Appl. No. 15/475,425, dated Jul. 12, 2018, 31 pages.
Non-Final Office Action for U.S. Appl. No. 15/531,922, dated Jun. 12, 2018, 17 pages.
Non-Final Office Action for for U.S. Appl. No. 12/464,369, dated Feb. 27, 2014, 25 pages.
Notice of Allowance dated Feb. 1, 2017 from U.S. Appl. No. 14/858,715, filed Sep. 18, 2015 (8 pages).
Notice of Allowance for U.S. Appl. No. 10/809,471, dated Mar. 24, 2008, 14 pages.
Notice of Allowance for U.S. Appl. No. 10/809,471, dated Oct. 5, 2007, 11 pages.
Notice of Allowance for U.S. Appl. No. 10/818,307, dated May 18, 2009, 8 pages.
Notice of Allowance for U.S. Appl. No. 11/334,968, dated Apr. 17, 2009, 11 pages.
Notice of Allowance for U.S. Appl. No. 11/377,042, dated Sep. 8, 2009, 16 pages.
Notice of Allowance for U.S. Appl. No. 11/510,197, dated Feb. 1, 2010, 13 pages.
Notice of Allowance for U.S. Appl. No. 11/849,969, dated Aug. 20, 2009, 21 pages.
Notice of Allowance for U.S. Appl. No. 11/849,969, dated Jul. 10, 2009, 18 pages.
Notice of Allowance for U.S. Appl. No. 11/857,432, dated Jun. 17, 2009, 17 pages.
Notice of Allowance for U.S. Appl. No. 12/429,695, dated Dec. 15, 2009, 7 pages.
Notice of Allowance for U.S. Appl. No. 12/429,695, dated Nov. 17, 2009, 12 pages.
Notice of Allowance for U.S. Appl. No. 12/464,369, dated May 8, 2015, 29 pages.
Notice of Allowance for U.S. Appl. No. 12/576,644, dated Dec. 10, 2010, 14 pages.
Notice of Allowance for U.S. Appl. No. 13/096,716, dated Oct. 30, 2013, 25 pages.
Notice of Allowance for U.S. Appl. No. 13/096,724, dated Aug. 19, 2014, 17 pages.

(56) References Cited

OTHER PUBLICATIONS

Notice of Allowance for U.S. Appl. No. 13/096,728, dated Feb. 7, 2014, 33 pages.
Notice of Allowance for U.S. Appl. No. 13/096,735, dated Jun. 24, 2013, 24 pages.
Notice of Allowance for U.S. Appl. No. 13/096,735, dated Oct. 4, 2013, 26 pages.
Notice of Allowance for U.S. Appl. No. 14/100,615, dated Sep. 28, 2015, 22 pages.
Notice of Allowance for U.S. Appl. No. 14/509,356, dated Aug. 1, 2017, 29 pages.
Notice of Allowance for U.S. Appl. No. 14/509,366, dated Jul. 31, 2017, 59 pages.
Notice of Allowance for U.S. Appl. No. 14/846,090, dated Jul. 25, 2016, 22 pages.
Notice of Allowance for U.S. Appl. No. 14/858,715, dated Feb. 1, 2017, 42 pages.
Notice of Allowance for U.S. Appl. No. 14/858,715, dated Feb. 1, 2017, 8 pages.
Notice of Allowance for U.S. Appl. No. 14/858,715, dated Mar. 1, 2017, 13 pages.
Notice of Allowance for U.S. Appl. No. 14/863,936, dated Mar. 20, 2018, 9 pages.
Notice of Allowance for U.S. Appl. No. 14/863,950, dated Mar. 27, 2018, 9 pages.
Notice of Allowance for U.S. Appl. No. 14/863,960, dated Mar. 20, 2018, 9 pages.
Office Action dated Aug. 3, 2016 from U.S. Appl. No. 14/863,950, filed Sep. 24, 2015 (15 pages).
Office Action dated Aug. 3, 2016 from U.S. Appl. No. 14/863,960, filed Sep. 24, 2015 (21 pages).
Office Action dated Aug. 4, 2016 from U.S. Appl. No. 14/863,936, filed Sep. 24, 2015 (16 pages).
Office Action dated Feb. 21, 2017 from U.S. Appl. No. 14/509,366, filed Oct. 8, 2014 (25 pages).
Office Action dated Mar. 14, 2016 from U.S. Appl. No. 14/858,715, filed Sep. 18, 2015 (9 pages).
Office Action dated Mar. 3, 2016 from U.S. Appl. No. 14/509,366, filed Oct. 8, 2014 (19 pages).
Ortiz et al., An Optimal Strategy for Dilation Based Iris Image Enrollment. IEEE International Joint Conference on Biometrics. 6 pages, Sep. 29-Oct. 2, 2014.
Restriction Requirement for U.S. Appl. No. 11/510,197, dated May 16, 2008, 12 pages.
Robert J.K. Jakob, "Eye Movement Based Human Computer Interaction Techniques; Toward Non-Command Interfaces," Advances in Human-Computer Interaction, vol. 4, ed. by H.R. Hartson and D. Hix, pp. 151-190, Ablex Publishing Co., Norwood, N.J. (1993).
Robert J.K. Jakob, "Eye Tracking in Advanced Interface Design," in Virtual Environments and Advanced Interface Dseign, ed. by W. Barfield and T.A. Furness, pp. 258-288, Oxford University Press, New York (1995).
Roth, Mouthpiece Meditations, Part 3. Online Trombone Journal, www.trombone.org. 5 pages, Jul. 23, 2018.
Schovanec, Ocular Dynamics and Skeletal Systems, IEEE Control Systems Magazine. Aug. 2001;21(4):70-79.
Scoblete, The Future of the Electronic Shutter. pdn, Photo District News, retrieved online at: https://www.pdnonline.com/gear/cameras/the-future-of-the-electronic-shutter/, 6 pates, May 9, 2016.
Second Japanese Office Action for Application 2015-545911 dated Feb. 26, 2018 ( with English translation).
Singapore Search Report and Written Report for Application No. 11201704097X, dated Mar. 13, 2018, 5 pages.
SRI International, "Seeing the Future of Iris Recognition", available at www.sri.com/iom, Mar. 2014, 9 pages.
Swiniarski, Experiments on Human Recognition Using Error Backpropagation Artificial Neural Network. Neural Networks Class (CS553) of San Diego State University Computer Science Department, Apr. 2004.
U.S. Appl. No. 14/100,615, "Iris Biometric Matching System", filed Dec. 9, 2013, 57 pages.
U.S. Appl. No. 14/100,615, "Iris Biometric Matching System," filed Dec. 9, 2013, 61 pages.
U.S. Appl. No. 61/888,130, filed Oct. 8, 2013, 20 pages.
van der Wal, et al., "The Acadia Vision Processor," IEEE International Workshop on Computer Architecture for Machine Perception, pp. 31-40, Padova, Italy, Sep. 11-13, 2000.
Weisstein E. et al.; "Circle" From MathWorld—A Wolfram Web Resource. www.mathworld.wolfram.com/circle.html, pp. 1 to 8., Jul. 3, 2008.
Wildes, R., "Iris Recognition: An Emerging Biometric Technology," Proc. IEEE, 85(9):1348-1363, Sep. 1997.
Written Opinion for Application No. PCT/US2017/065793, dated Feb. 16, 2018, 10 pages.
Written Opinion for PCT/US2015061024, dated Mar. 21, 2016.
Written Opinion of the International Searching Authority dated Jun. 28, 2018, issued in connection with International Application No. PCT/US2018/025895 (10 pages).
www.m-w.com—definition—"ellipse" (Refer to Ellipse Illustration; also attached) pp. 1 of 2.
Yokoya, Ryunosuke, and Shree K. Nayar. "Extended depth of field catadioptric imaging using focal sweep." Proceedings of the IEEE International Conference on Computer Vision. 2015.
Zhu, et al., "Biometric Personal Identification Based on Iris Patterns," Pattern Recognition, Proceedings 15th International Conference on vol. 2 IEEE (2000) (4 pages).

* cited by examiner

CONTROL OF WIRELESS COMMUNICATION DEVICE CAPABILITY IN A MOBILE DEVICE WITH A BIOMETRIC KEY

CROSS-REFERENCES TO RELATED APPLICATIONS

This application claims priority to and the benefit of U.S. Provisional Patent Application Ser. No. 62/054,415, filed Sep. 24, 2014, and entitled "Control of the Wireless Communication Device/Capability (NFC, RFID, Bluetooth, Wifi, Wimax, Satcom, etc.) in a Mobile Device with a Biometric Key".

BACKGROUND

Many existing iris recognition-based biometric devices impose strict requirements on the iris image capture process in order to meet the needs of iris biometric analysis. For example, many existing devices can only utilize images that have a clear, straight-on view of the iris. In order to obtain such images, existing devices typically require the human subject to be stationary and located very near to the iris image capture device.

BRIEF DESCRIPTION OF THE DRAWINGS

This disclosure is illustrated by way of example and not by way of limitation in the accompanying figures. The figures may, alone or in combination, illustrate one or more embodiments of the disclosure. Elements illustrated in the figures are not necessarily drawn to scale. Reference labels may be repeated among the figures to indicate corresponding or analogous elements.

DETAILED DESCRIPTION OF THE DRAWINGS

Figure 1:
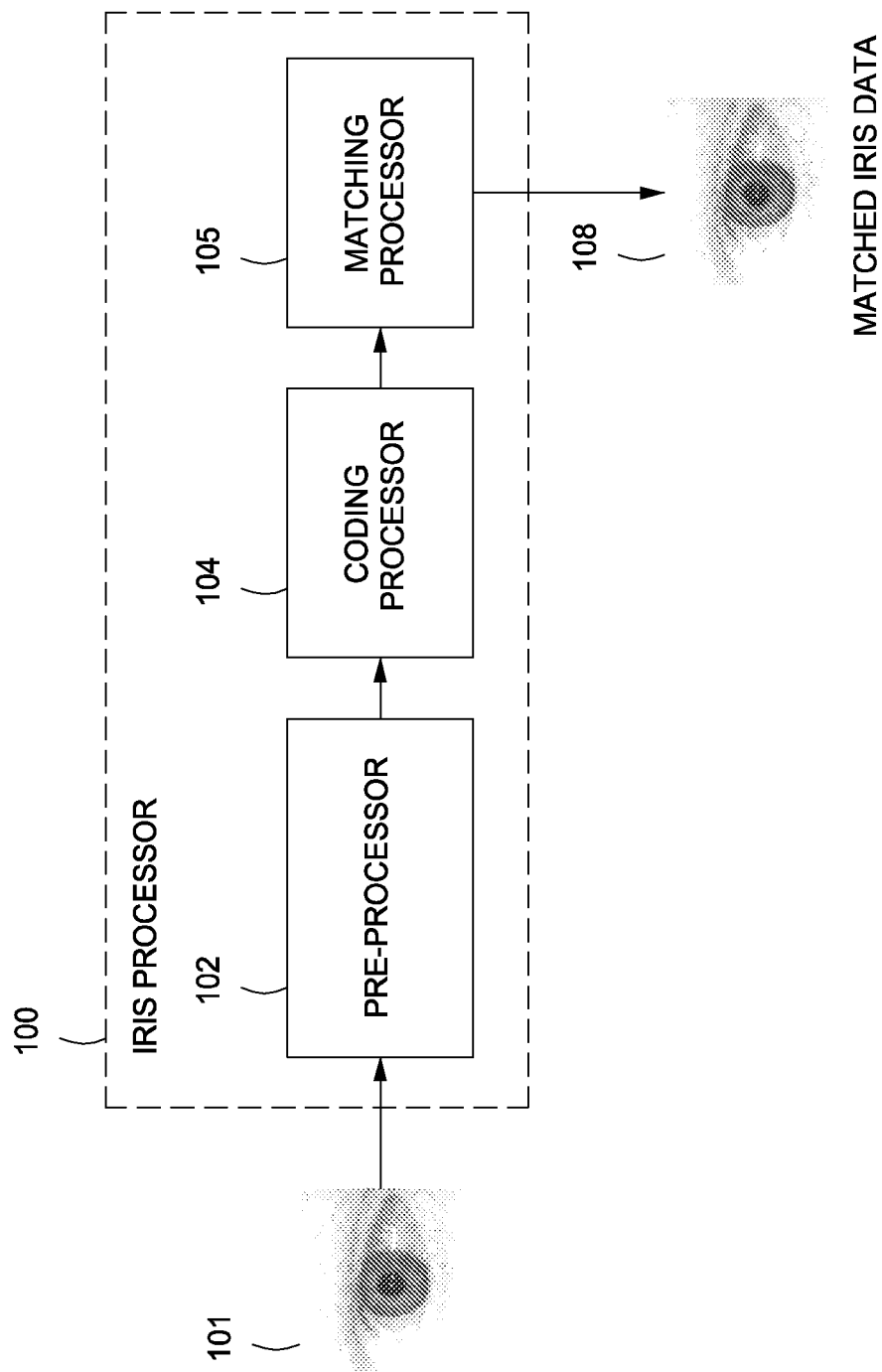
FIG. 1 depicts a simplified block diagram of at least one embodiment of an iris processor for biometric iris matching, including a pre-processor as disclosed herein.

While the concepts of the present disclosure are susceptible to various modifications and alternative forms, specific embodiments thereof are shown by way of example in the drawings and are described in detail below. It should be understood that there is no intent to limit the concepts of the present disclosure to the particular forms disclosed. On the contrary, the intent is to cover all modifications, equivalents, and alternatives consistent with the present disclosure and the appended claims.

Referring now to FIGS. 1-12, FIGS. 1-12 relate to subject matter that is shown and described in U.S. Utility patent application Ser. No. 14/100,615, filed Dec. 9, 2013, and U.S. Utility application Ser. Nos. 14/509,356 and 14/509,366, both filed Oct. 8, 2014.

FIG. 1 depicts a block diagram of an iris processor 100 for biometric iris matching in accordance with exemplary embodiments of the present invention. The iris processor 100 comprises a pre-processor 102, a coding processor 104 and a matching processor 106. The iris processor 100 receives images as input, for example, input image 101 and outputs a matched iris 108 from a remote or local database. Those of ordinary skill in the art would recognize that the database may be accessed as a "cloud" service, directly through an internet connection, or the like. The pre-processor 102, the coding processor 104 and the matching processor 106 may execute on a single device (e.g., within a software application running on, for example, a mobile device, having captured the images via a camera and/or means of illumination integrated into the mobile device), or on different devices, servers, cloud services or the like, as indicated by the dashed outline of the iris processor 100. The iris processor 100 may be modular and each processor may be implemented, e.g., on a single device, multiple devices, in the cloud as a service. Any of the components, e.g., the pre-processor 102, the coding processor 104, and the matching processor 106, may be implemented or used independently of one another.

According to exemplary embodiments of the present invention, the input image 101 is an infrared image, and is captured by an infrared capture device (not shown in FIG. 1), coupled to the iris processor 100. The infrared capture device may be any type of infrared capture device known to those of ordinary skill in the art. In other instances, the input image 101 is a red, green, blue (RGB) image, or the like. The input image 101 contains an eye with an at least partially visible iris and pupil and the iris processor 100 attempts to match that eye with an iris of an eye image in a local or remote database of eye images. According to exemplary embodiments, irises are matched based on Hamming distances between two coded iris images.

Initially, the input image 101 is processed by the pre-processor 102. The pre-processor 102 segments and normalizes the iris in the input image 101, where input image 101 may have variable iris/pupil and iris/sclera contrast, small eyelid openings, and non-frontal iris presentations. The result of the pre-processor 102 is a modified iris image with clearly delineated iris boundaries and synthesized quasi-frontal presentation. For example, if the iris in the input image 101 is rotated towards the left, right, up or down, the pre-processor 102 will synthesize an iris on the input image 101 as if it was positioned directly frontally. Similarly, a frontally positioned pupil will be synthesized on the skewed or rotated pupil of the input image 101.

The coding processor 104 analyzes and encodes iris information from the iris image generated by the pre-processor 102 at a range of spatial scales so that structural iris information contained in the input image 101 of varying resolution, quality, and state of focus can be robustly represented. The information content of the resulting code will vary depending on the characteristics of input image 101. The code generated by the coding processor 104 representing the input image 101 allows spatial interpolation to facilitate iris code alignment by the matching processor 106.

The output code from the coding processor 104 is coupled to the matching processor 106. The matching processor 106 incorporates constrained active alignment of iris structure information between stored iris images and captured iris codes generated from the input image 101 to compensate for limitations in iris image normalization by the pre-processor 102. The matching processor 106 performs alignment by performing local shifting or warping of the code to match the generated code with a stored iris code template based on estimated residual distortion of the code generated by the coding processor 104. According to some embodiments, a "barrel shift" algorithm is employed to perform the alignment. Accordingly, structural correspondences are registered and the matching processor 106 compares the aligned codes to determine whether a match exists. If a match is found, the matching processor returns matched iris data 108.

The matched iris data 108 may be used in many instances, for example, to authenticate a user in order for the user to gain access to a secure item (e.g., a safe, safety deposit box, computer, etc.), authenticate a user to access applications or wireless communication within a computing device, such as a mobile device (e.g., authenticating a user in order to transmit instructions from the user's mobile device to an automated teller machine (ATM) in order to complete a financial transaction), authorize financial transactions and/or collect, analyze and display an identify of a user in order to deliver targeted marketing to the user, as described in detail below. The pre-processor 102 may be an application executing on a mobile device, such as a mobile phone, camera, tablet, forward or rear facing camera integrated into a mobile phone or table, or the like. The pre-processor 102 on the mobile device may capture an image of a user's eye using the camera of the device, perform the pre-processing steps on the mobile device, and then transmit a bundled and encrypted request to the coding processor 104, which may be accessed via a cloud service on a remote server of, for example, a transaction initiated and completed via a wireless communication from a mobile device to an ATM and/or remote server in order to complete a financial transaction with a financial institution. In other embodiments, the application on the mobile device may also comprise the coding processor 104 and the iris coding is performed on the mobile device.

The iris processor 100 may be used to authorize a cellular device user, determining whether the device is stolen or not, in conjunction with geo-location data, or the like. In this embodiment, upon purchase of a cellular device, the user may "imprint" their identity on the device based on their iris information so that others can be prevented from using the device if reported stolen. Similarly, this imprint may be used to authenticate the mobile device user to access user-specific applications and or settings on the mobile device, including those that utilize wireless communication transmissions. Authorization can also be extended to the office or personal environments, where the iris processor 100 may be used to determine whether an authorized or detected user has access to a particular location or security enabled object within that particular location. For example, in a secure office environment, taking photographs may be prohibited for the majority of employees, but overriding this prohibition and enabling the camera is available to authorized employees. The employee's mobile device will be used to capture an image of the employee, and the iris processor 100 will match the iris of the employee to extract an employee profile, which delineates the authorizations for this employee.

In the medical field, the iris processor 100 may be used to determine whether a person accessing particular medical resources, such as medicine, devices, or the like, are permitted to access these resources. The iris processor 100 can be coupled with a recording device, which captures video of those accessing a medicine cabinet, for example, and whether they are authorized to take medical resources from the cabinet.

In summary, the iris processor may be used in any context in which the user needs to be authenticated, including any situation in which the user wants physical or electronic access to a device or data accessible via the device.

Figure 2:
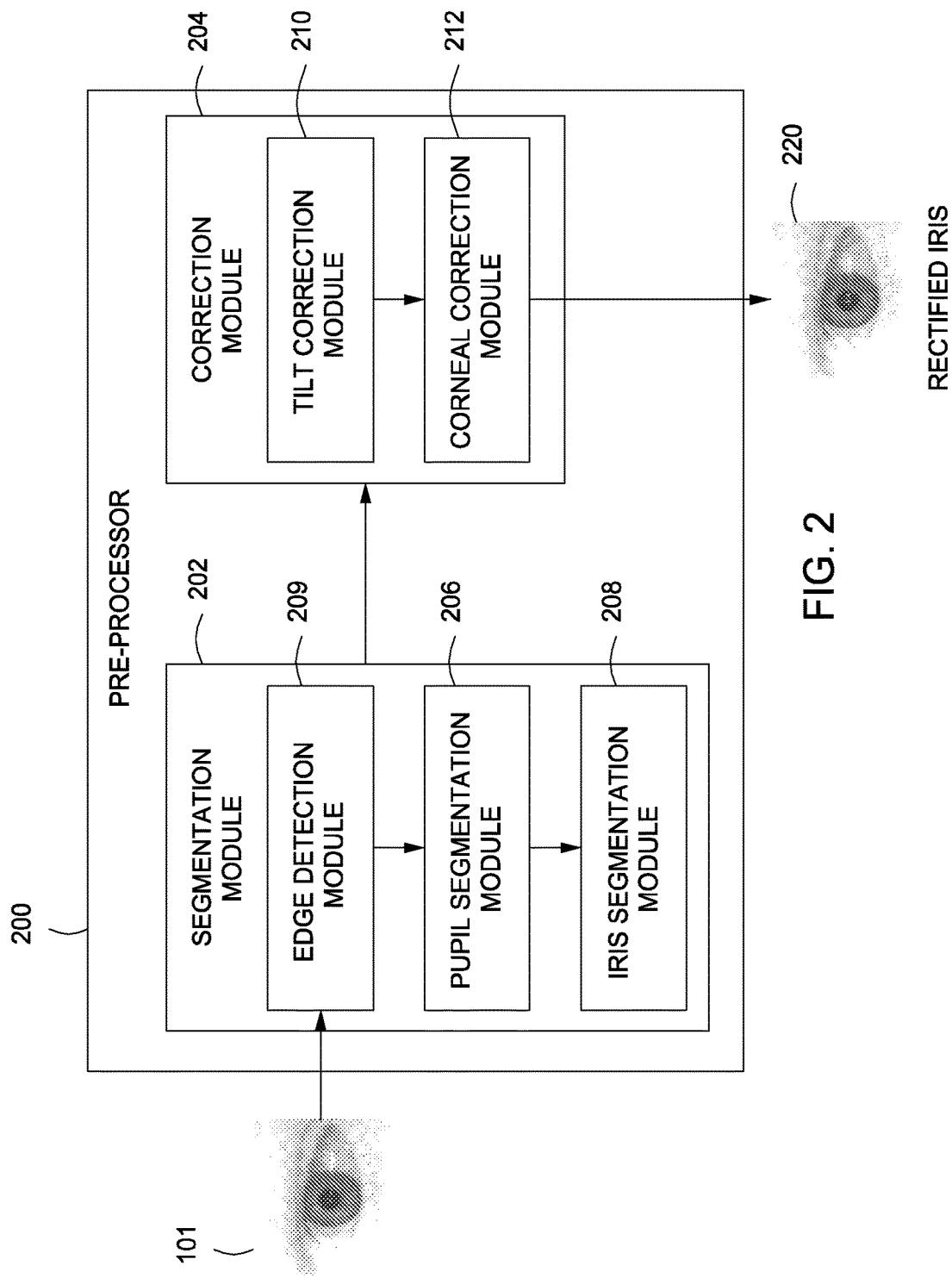
FIG. 2 depicts a simplified block diagram of at least one embodiment of the pre-processor of the iris processor of FIG. 1.

FIG. 2 depicts a block diagram of the pre-processor of the iris processor 100 in accordance with exemplary embodiments of the present invention. The pre-processor receives the input image 101 and outputs a rectified iris image 220. The rectified iris image 220 corrects for uncontrolled capture scenarios such as ambient illumination conditions, varied illumination geometries, reduced eyelid opening area, presentation angle (obliquity), or the like. The rectified iris image 220 corrects for various nonconformities.

The pre-processor 200 comprises a segmentation module 202 and a correction module 204. The segmentation module 202 further comprises a pupil segmentation module 206, an iris segmentation module 208 and an edge detection module 209. The segmentation module 202 corrects an input image for low-contrast pupil and iris boundaries. The image produced by the segmentation module 202 is then coupled to the correction module 204 for further correction. The correction module 204 comprises a tilt correction module 210 and a corneal correction module 212. The details of the segmentation module 202 are described below.

Figure 3A:
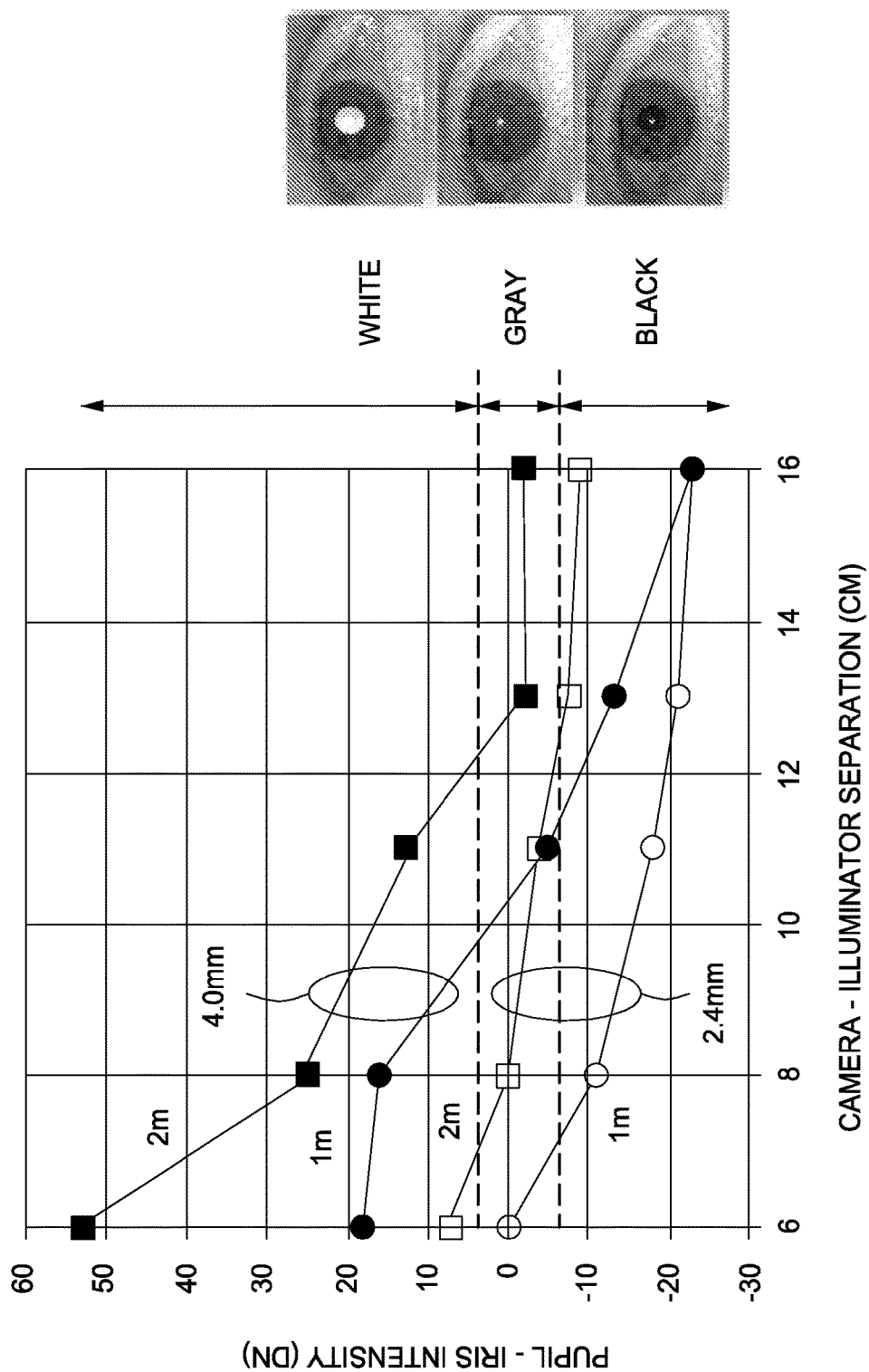
FIG. 3A depicts a simplified graphical plot illustrating an effect of camera illumination on pupil and iris intensity as disclosed herein.

FIG. 3A illustrates that varying illumination geometry produces varying pupil appearance. FIG. 3A illustrates measurement of pupil-iris intensity difference as a function of distance, e.g., 1 and 2 meters, pupil size, e.g., 2.4 mm and 4.0 mm, and camera/illuminator distance, e.g., 6 to 16 cm. As the camera/illuminator distance increases, the pupil iris intensity decreases. The contrast of the pupil varies greatly as a function of distance between camera and subject as well as functions of illuminator geometry and pupil diameter. The variation with distance is due to the fact that the angular distance between the illuminator and camera axes are greater at short range (e.g., 1 m) than at longer distances. As the illuminator and camera axes get closer, more light that is reflected from the retina back out through the pupil is captured by the camera lens. This causes red eye in ordinary photographs and bright pupils in infrared photography. An exemplary illuminator is described in U.S. Pat. No. 7,542,628 to Matey entitled "Method and Apparatus for Providing Strobed Image Capture" filed on Jan. 19, 2006, and U.S. Pat. No. 7,657,127 to Matey entitled "Method and Apparatus for Providing Strobed Image Capture" filed on Apr. 24, 2009, each of which is incorporated herein by this reference in its entirety.

The segmentation module 202 and the correction module 204 may be used, for example, in the medical field, in targeted marketing, customer tracking in a store, or the like. For example, pupil and iris insertion may be performed by the pre-processor 102, as described further with respect to FIGS. 2 and 3A-3D, in the medical field as a diagnostic tool for diagnosing diseases that a person might have based on their iris profiles.

Figure 3B:
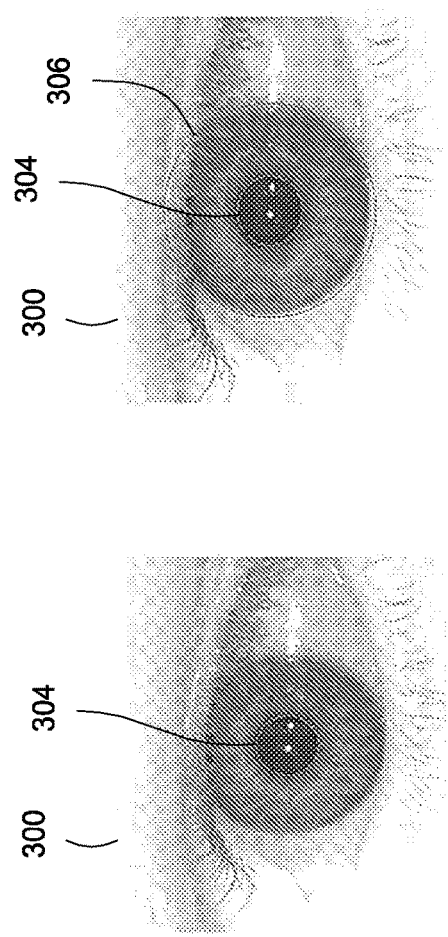
FIG. 3B depicts an illustration of a result of the operation of the pre-processor of FIG. 2.
Figure 3C:
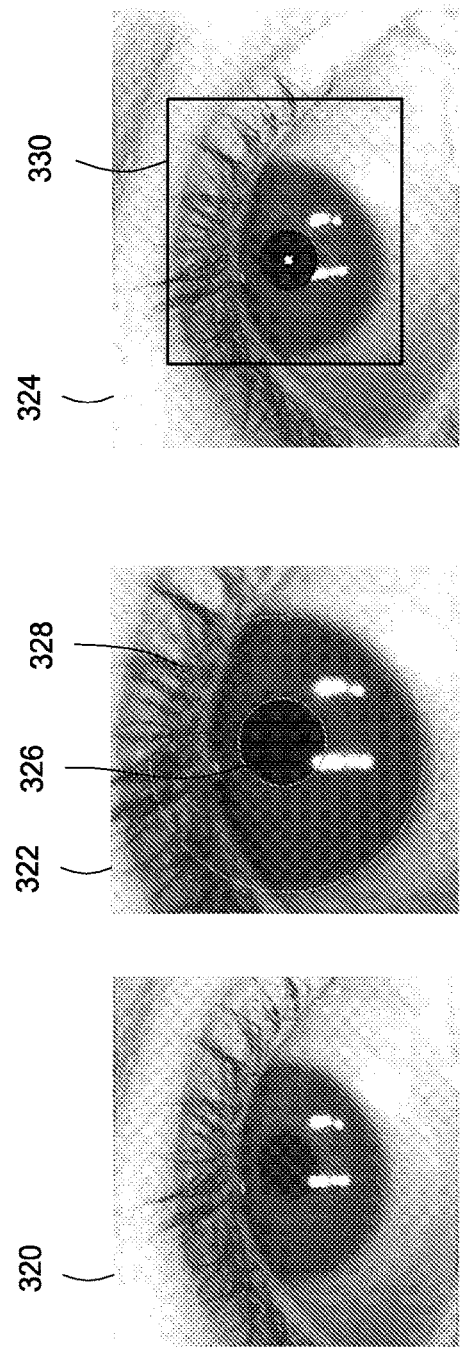
FIG. 3C depicts an illustration of another result of the operation of the pre-processor of FIG. 2, with an alternate image.
Figure 3D:
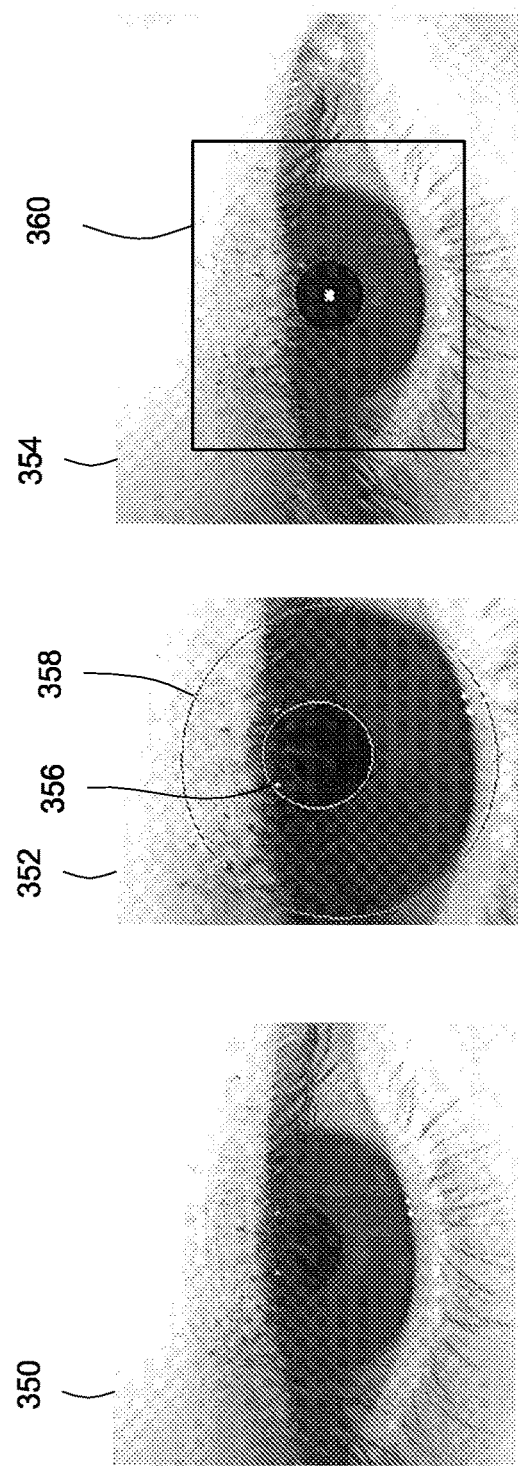
FIG. 3D depicts a simplified illustration of yet another result of the operation of the pre-processor of FIG. 2, with yet another alternate image.

FIG. 3B illustrates an example of iris and pupil boundary matching in accordance with exemplary embodiments of the present invention. According to some embodiments, iris diameters are normalized by the iris segmentation module 208. Size normalization is performed using a range estimate derived from an autofocus setting of the camera taking the image. The image 300 shows the pupil boundary 304 calculated by the pupil segmentation module 206. The pupil segmentation module 206 then inserts an artificial dark pupil in the pupil boundary 304 in image 300. Image 300 is then coupled to the iris segmentation module 208, which calculates the iris boundary. FIGS. 3C and 3D illustrate examples of inserted artificial pupils and iris boundaries. In FIG. 3C, input image 320 is coupled to the pre-processor 200. The input image 320 is then segmented by pupil segmentation module 206 to calculate a pupil boundary region 326. The pupil segmentation module then inserts an artificial black colored pupil in the pupil boundary region 326. Additionally, oblique irises and pupils are warped to be circular. The insertion of an artificial pupil in the pupil boundary region 326 may be used, for example, to remove red-eye effects in an image captured by a camera. The segmentation module 202 can be used to segment the pupil and iris areas, and the pupils may be red-eye corrected by insertion of the artificial pupil. This process of segmentation and warping is described in more detail below.

FIG. 3D shows a similar process but on a downward facing iris in image 350. The pupil boundary 356 is still detected despite being occluded by the eyelid in image 352. The pupil and iris are both warped to form circular regions to aid in segmentation. The pupil segmentation module 206 inserts a black disk/artificial pupil in the image 352 and couples the image 352 to the iris segmentation module 208. The iris segmentation module 208 determines an iris boundary 358. Ultimately, the iris and pupil boundaries are corrected for various lighting conditions and presented in image 354, where region 360 can be seen with the artificial pupil. According to some embodiments, the artificial pupil need not be necessarily black and may be another suitable color, based on compatibility with third party iris recognition software.

The pupil boundaries, for example, 304, 326 and 356 and the iris boundaries (iris/sclera boundary areas), for example, 306, 328 and 358 are calculated using a Hough transform, according to one embodiment. The pupil segmentation module 206 and the iris segmentation module 208 employ edge detection using the edge detection module 209 to generate edge maps which works for varying scales of grayscale pupils, even in instances with low edge contrast. Once the pupil segmentation module 206 determines the segmented pupil area (and therefore, the pupil contour) and the pupil and iris have been warped to form circular regions, the segmented pupil area is replaced with a black or dark disk to simulate the appearance of a dark pupil.

Figure 4A:
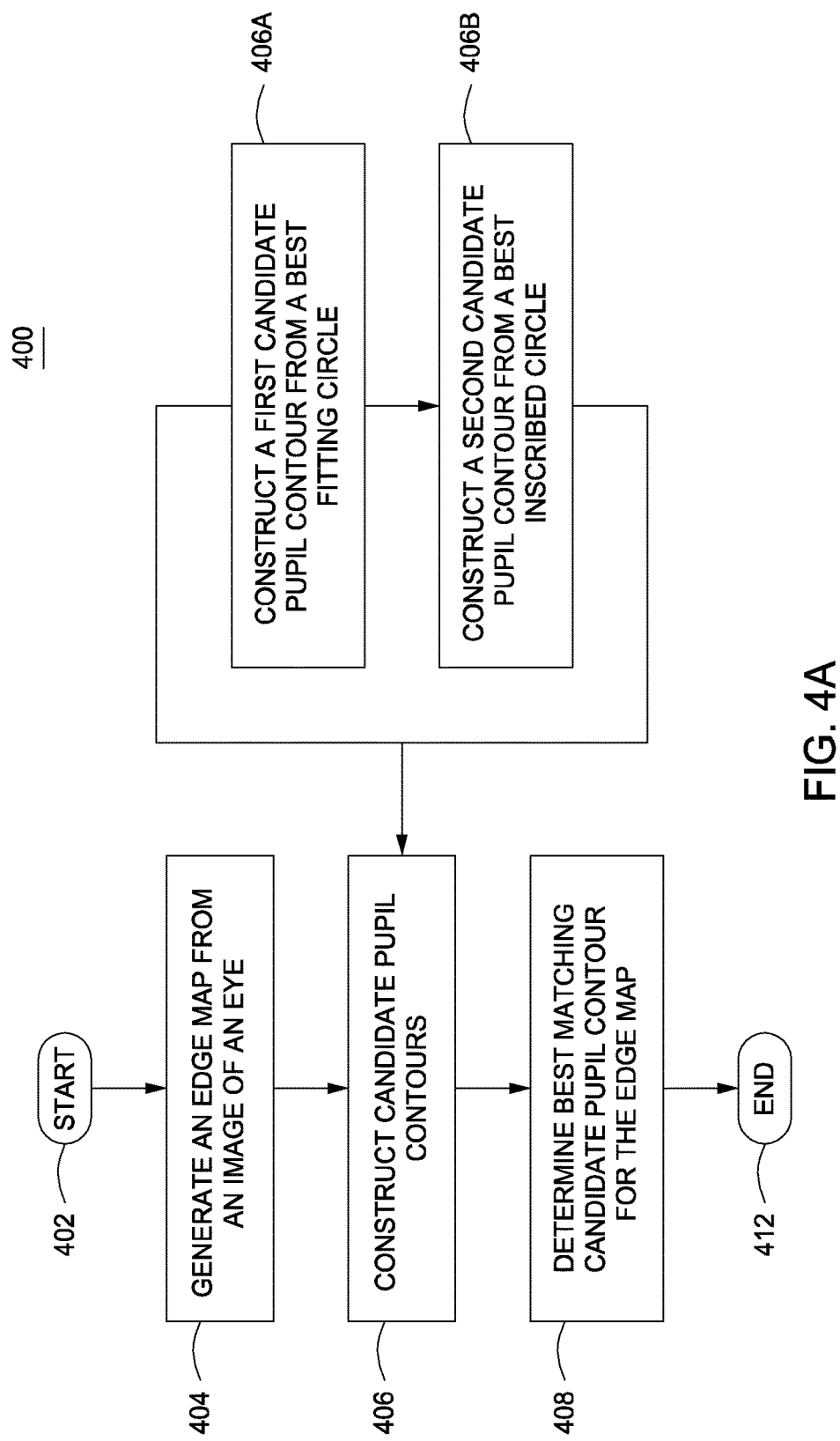
FIG. 4A depicts a simplified flow diagram for at least one embodiment of a method for edge detection, which may be performed by the iris processor of FIG. 1.

FIG. 4A depicts a flow diagram for a method 400 for edge detection in accordance with one embodiment of the present invention. The method 400 is an exemplary illustration of the operation of the edge detection module 209 used to detect pupil and iris boundaries.

Figure 4B:
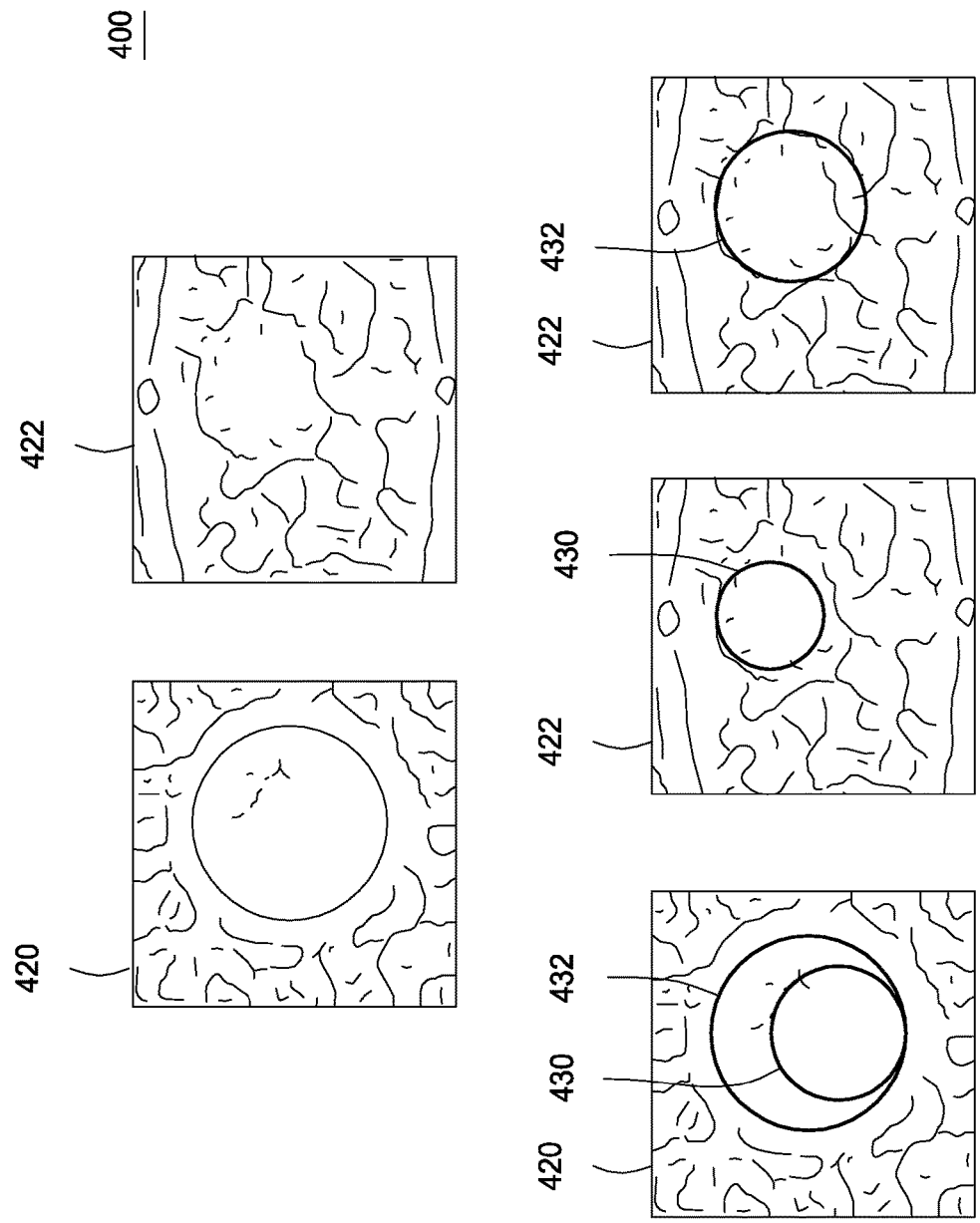
FIG. 4B shows simplified examples of candidate pupil contour curves as disclosed herein.

The method begins at step 402 and proceeds to step 404. At step 404, an edge map is generated from an image of an eye, for example, input image 101. An exemplary edge map for an iris image which was brightly illuminated is shown in FIG. 4B, image 420. Image 422 is an edge map for an iris image which was not as brightly illuminated, i.e., an indistinct pupil whose edges are not as clearly visible as those in image 420.

At step 406, candidate pupil contours are constructed for the given edge map. Step 406 consists of sub-steps 406A and 406B. At sub-step 406A, a first candidate pupil contour is created from a best fitting circle, as shown in FIG. 4B, image 420. For example, a Hough transform or RANSAC (random sample consensus) method can be used to find the circle that has the greatest level of support in the edge map in the sense that the largest fraction of circle points for that circle coincide with edge points. At step 406B, a second candidate pupil contour is constructed from a best inscribed circle as shown in FIG. 4B, image 422. Those of ordinary skill in the art would recognize that an inscribed circle is a circle that can be drawn in an area/region of the edge map so that no edge points (or no more than a specified small number of edge points) lie within the circle. According to one embodiment, the best inscribed circle is the largest such inscribed circle that can be found in the area/region of the pupil. Then method then proceeds to step 408, where the method 400 determines the best matching candidate pupil contour from the first and second candidate pupil matching contours for the edge map. According to one embodiment, the best match is determined by assessing a level of support for the best fitting circle and selecting the best fitting circle as the best match if this level of support is above a threshold value. The best inscribed circle is selected as the best match if the level of support for the best fitting circle is below a threshold value.

According to one embodiment, an automatic process based on how well the best fit contour (circle) matches the edge contour in the edge contour map is used to decide which candidate contour to choose. For example, for the best supported circle described above, a subset of edge points can be selected that is limited to those edge points whose angular orientation is consistent with that edge point being a part of the candidate circle. In other words only edge points whose direction is approximately perpendicular to the direction from the estimated center of the candidate circle are included. This process eliminates from consideration those edge points that may accidentally fall at the correct position to be part of the circle but that do not correspond to the actual circle contour. If the proportion of such selected edge points is greater than some specified fraction (e.g. 20%) of the number of points comprising the circle then the level of support for that circle is deemed to be sufficient and the best fitting circle is selected. If the level of support by the selected edge points is less than this threshold then the best fitting circle is deemed to have insufficient support and the best inscribed circle is selected instead. Generally speaking, the best fit candidate contour will provide accurate pupil segmentation in the bright pupil image, as shown in FIG. 4B, image 420, where the bright colored eye edge map is overlayed with the best-inscribed circle 430 and the best fitting circle 432. The method then terminates at step 412 when a best matching candidate pupil contour is found.

In some instances, iris images may be captured over a range of oblique viewing conditions, for example, where gaze deviation with nasal gaze angles ranges from 0 to 40 degrees, as shown in FIG. 3D. The tilt correction module 210 rectifies the images for this tilt and generates a tilt corrected image. According to one embodiment, a tilt-corrected image may be generated by estimating or determining the magnitude and direction/angle of tilt, and then applying a geometric transformation to the iris image to compensate for the oblique viewing angle. In the case where the iris is a flat disk, the simplest form of this transformation is a stretching of the image in the direction of the tilt to compensate for the foreshortening caused by the angle between the iris and the image plane. Such a non-isotropic stretching is mathematically represented as an affine transformation. A more accurate version of this geometric de-tilting replaces the affine transformation with a projective transformation which better represents the image representation of a pattern on a flat, tilted surface.

The correction module 204 has several uses independent of the other components of the iris processor 100. For example, the correction module 204 may be used to detect a person's gaze, or to track a person's gaze continuously by capturing one or more frames of a person's eyes. The tilt correction module 210 may, for example, be used to continuously track a user's gaze on a mobile device and scroll a document, perform a swipe or the like. This tilt detection can be used, for example, independently of the matching processor 106 described in FIG. 1 to enable or disable the display of a mobile device.

In some embodiments, the correction module 204 corrects the input image 101 prior to the segmentation module establishing artificial pupil discs on the input image 101. In some instances, tilt correction may still show distortions such as the apparent eccentric pupil compression of the nasal portion of the iris, causing difficulty in biometrically matching the iris with a stored iris image. The distortion is caused by the optical effect of the cornea and anterior chamber of the human eye through which the iris is imaged. These two structures have similar refractive indexes (1.336 for the aqueous humor that fills the anterior chamber and 1.376 for the cornea) so that together their optical effect is approximately that of a single water-filled plano-convex lens in contact with the iris. Viewed from an oblique angle such a lens will produce asymmetric distortion in the iris image, compressing the image in some areas and expanding it in others. The tilt corrected image generated by the tilt correction module 210 is coupled to the corneal correction module 212, which corrects for the above described corneal distortion.

Figure 4C:
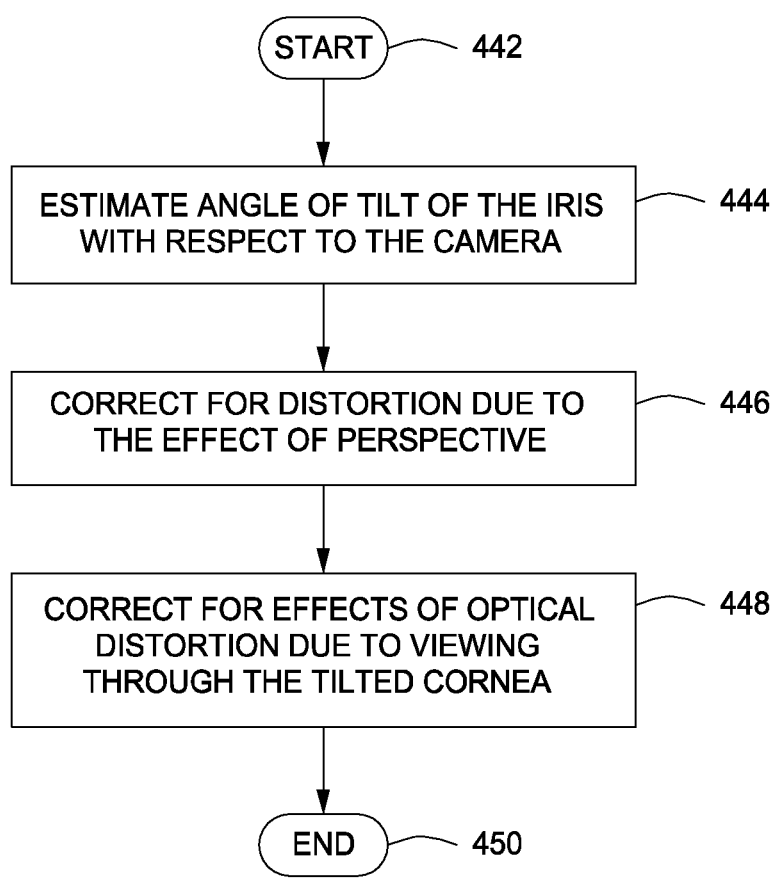
FIG. 4C depicts a simplified flow diagram for at least one embodiment of a method for corneal distortion correction, which may be performed by the iris processor of FIG. 1.

FIG. 4C depicts a flow diagram for a method 440 for corneal distortion correction in accordance with exemplary embodiments of the present invention. The method 400 is an exemplary illustration of the operation of the edge detection module 209. The method begins at step 402 and proceeds to step 404. At step 404, the tilt correction module 210 estimates the angle of tilt of the iris with respect to the camera orientation. The tilt can be estimated roughly by finding the pupil center and measuring the distance between that center and the bright reflection in the cornea caused by the near infra-red illuminator used in iris imaging. Other methods of tilt estimation known to those of ordinary skill in the art may also be used. Indeed, any method of tilt estimation may be substituted herein.

The method proceeds to step 406, where the image is corrected for the perspective distortion, i.e., the foreshortening of the iris that occurs. The effect of foreshortening can be approximated as a simple compression of the captured image in the direction or tilt. This effect can therefore be compensated for by simply stretching the image in the direction derived from the tilt estimation step. A more accurate correction can also be performed by using a projective transformation to more precisely capture the foreshortening effect.

Finally, at step 448, the method 400 corrects for effects of optical distortion due to viewing through the tilted cornea. According to one embodiment, approximate correction for the optical distortion discussed above can be achieved by measuring and correcting the effects of pupil eccentricity and pupil elongation. The method terminates at step 450.

Figure 4D:
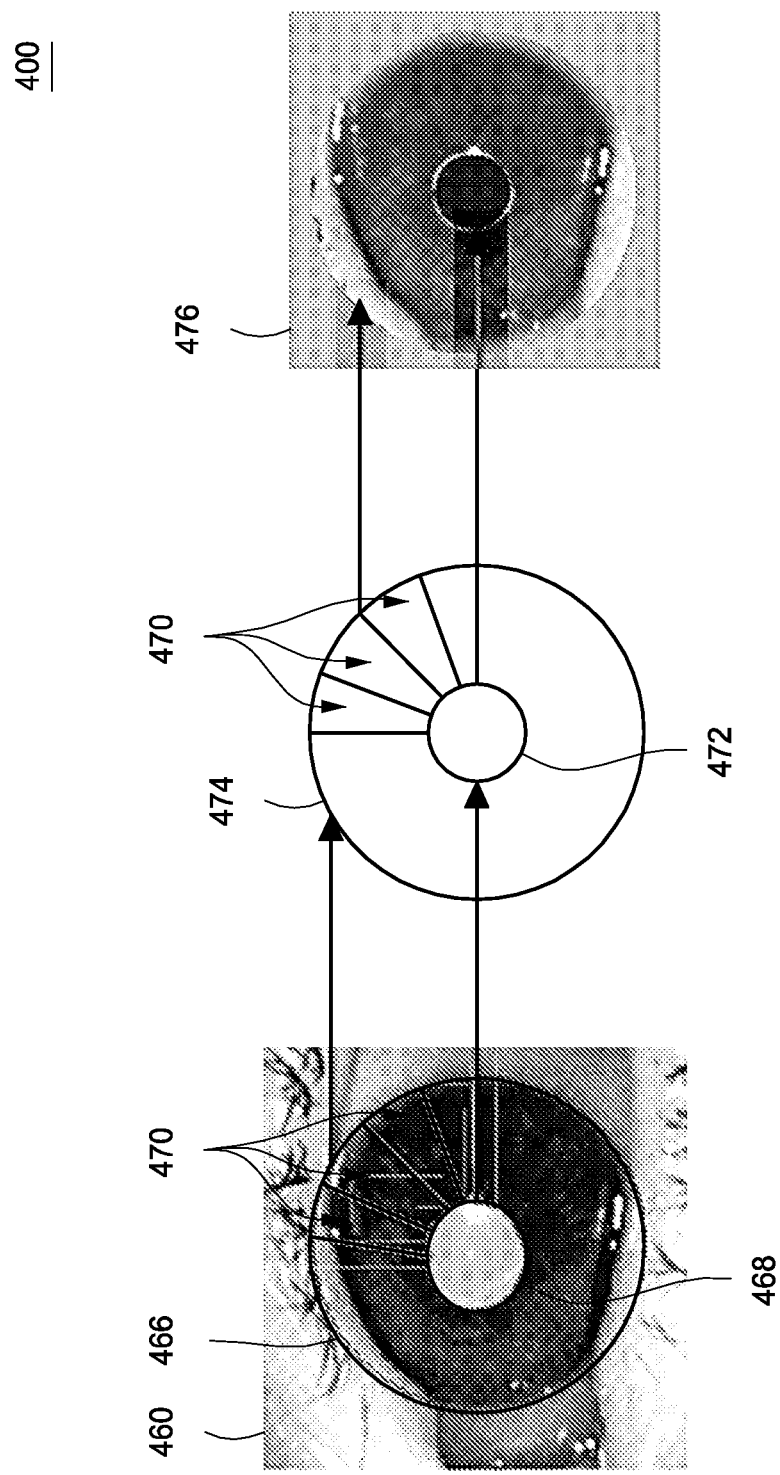
FIG. 4D illustrates a simplified result of correction for foreshortening as disclosed herein.

As seen in image 460 in FIG. 4D, after foreshortening correction based on tilt estimation, the pupil still appears shifted to the left with respect to the center of the iris and the pupil appears elongated in the horizontal direction. These effects are caused by the optical effects of the cornea. The corneal correction module 212 corrects for these distortions without modeling the optical elements that produced them by non-linearly warping the iris area/region to force the iris contour 466 and pupil contour 468 to become concentric circles. The corneal correction module 212 creates this nonlinear warping function by defining a set of spokes 470 that connect points on the non-circular pupil contour 468 to corresponding points on the non-circular iris/sclera contour 466 and mapping each spoke of the spokes 470 to a position connecting a synthetic circular pupil contour 472 to a concentric circular iris/sclera contour 474. The described transformation is then applied to the underlying image 460. The result of this mapping (with appropriate interpolation) is shown in image 476. After the pupil and iris areas/regions have been shifted to be in concentric circles, the coding process can be more accurately performed with better matching results.

After such a corrected image is constructed as described above, iris coding and matching can be performed using any desired iris biometric algorithm designed to be applied to iris images captured under standard controlled conditions. For example, the classic method of Daugman (Daugman, J., "High confidence visual recognition of persons by a test of statistical independence", IEEE Transactions on Pattern Analysis and Machine Intelligence, 15 (11), pp 1148-1161 (1993)) can be applied. However, methods developed by others can also be used, including but not limited to those of Munro (D. M. Monro and D. Zhang, An Effective Human Iris Code with Low Complexity, Proc. IEEE International Conference on Image Processing, vol. 3, pp. 277-280, September 2005) and Tan (Tan et al, Efficient Iris Recognition by Characterizing Key Local Variations IEEE TRANSACTIONS ON IMAGE PROCESSING, VOL. 13, NO. 6, June 2004).

Figure 5:
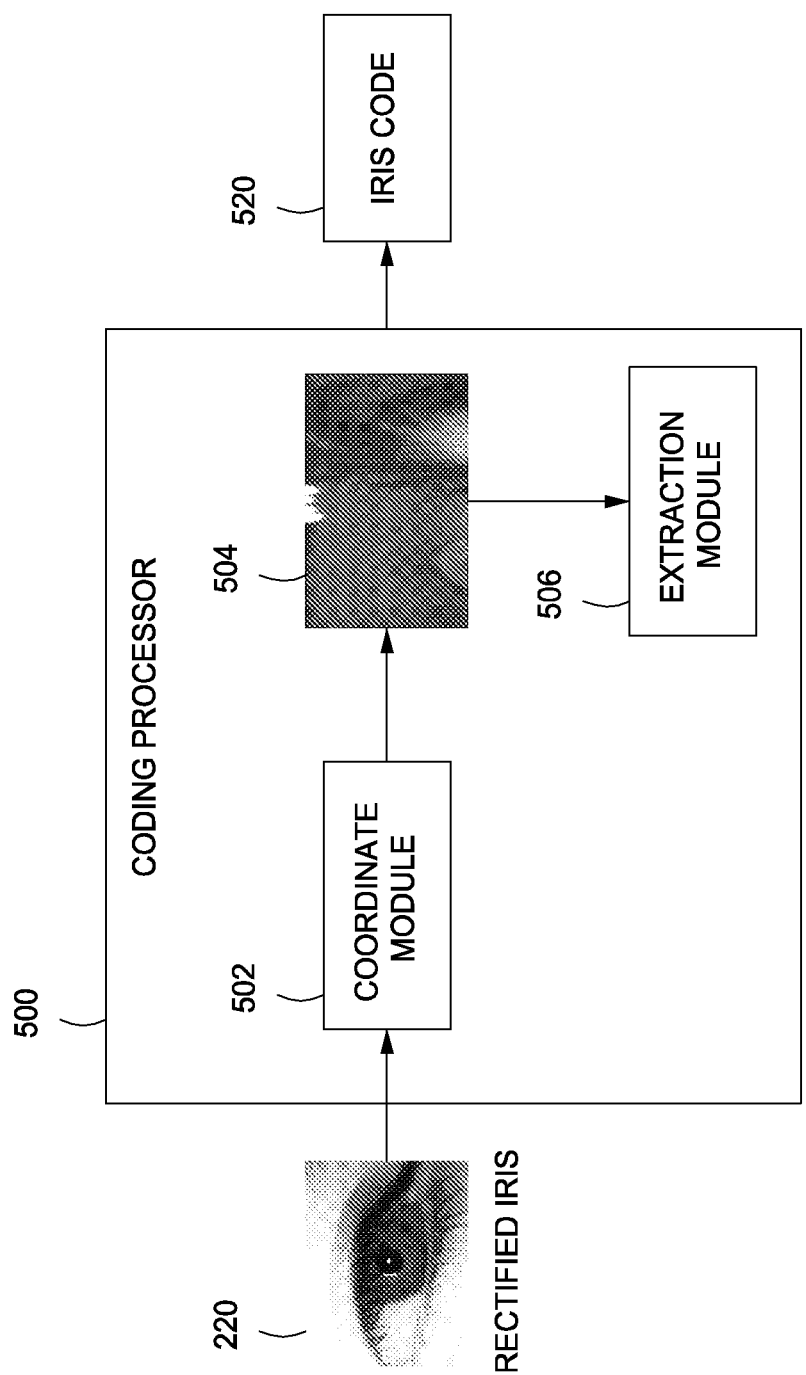
FIG. 5 depicts a simplified block diagram of at least one embodiment of a coding processor as disclosed herein.

FIG. 5 depicts a block diagram of a coding processor 500 in accordance with exemplary embodiments of the present invention. The coding processor 500 comprises a coordinate module 502 and an extraction module 506. The coordinate module 502 constructs an invariant coordinate system for an invariant coordinate system image representation that allows iris information extracted from varying iris images to be brought into register, so that corresponding spatial information can be compared. The extraction module 506 extracts information from the iris image for supporting a strong rejection of the hypothesis that two eye images presented represent statistically independent patterns. The coding processor 500 prepares the segmented and corrected iris image 220 for accurate matching with other iris images and allows unconstrained iris capture applications. For example, image size and focus may vary with distance, in addition to individual iris structure variations and variation with illumination wavelength of spatial information content of an iris structure. Generally, iris coding is based on angular frequencies between about 15 and 40 cycles/2pi or 2.5 and 6 pixels per cycle, where according to one embodiment, the present application achieves robust matching based on the codes generated by the coding processor 500 down to approximately 40 pixels per iris diameter.

According to one embodiment, the coding processor 500 uses a variant of Daugman's local phase representation, which encompasses a multi-resolution coding approach rather than choosing a single scale of analysis. Lower frequency components remain available in lower resolution images and are less prone to loss in defocused or otherwise degraded images. In one embodiment, the variant of Daugman's local phase representation allows for dense coding that is useful when dealing with iris images in which significant occlusion may occur. Although the robust segmentation and rectification process described above generates corrected iris images that can be used with a variety of iris coding and matching algorithms, there are advantages in some situations to retaining properties of standard algorithms. One advantage of the Daugman type phase coding approach is that it generates a code that represents all available parts of the iris images. This is in contrast to an approach that uses sparse local features that might be occluded or otherwise unavailable in a particular image to be matches. Further, the use of multiresolution phase approach preserves the possibility of achieving code-level compatibility with existing phase-based representations. In addition to containing multi-scale information, the code that is created can incorporate additional information to facilitate estimation of iris code alignment and spatial interpolation of local structure information prior to comparison.

As shown in FIG. 5, the coding processor 500 comprises the coordinate module 502. The coordinate module 502 transforms the rectified iris image 220 into a polar iris image 504. In this polar iris image 504 the pupil boundary appears at the top (notice the specular reflection of a biometric scanner illuminator column) and the iris-sclera boundary area appears at the bottom. The angular dimension runs clockwise from 3 o'clock at the left of the image. Proceeding from left to right, the lower and upper eyelids can be seen. Note that in image 504 the eyelashes extend from the upper eyelid all the way into the pupil.

Figure 6:
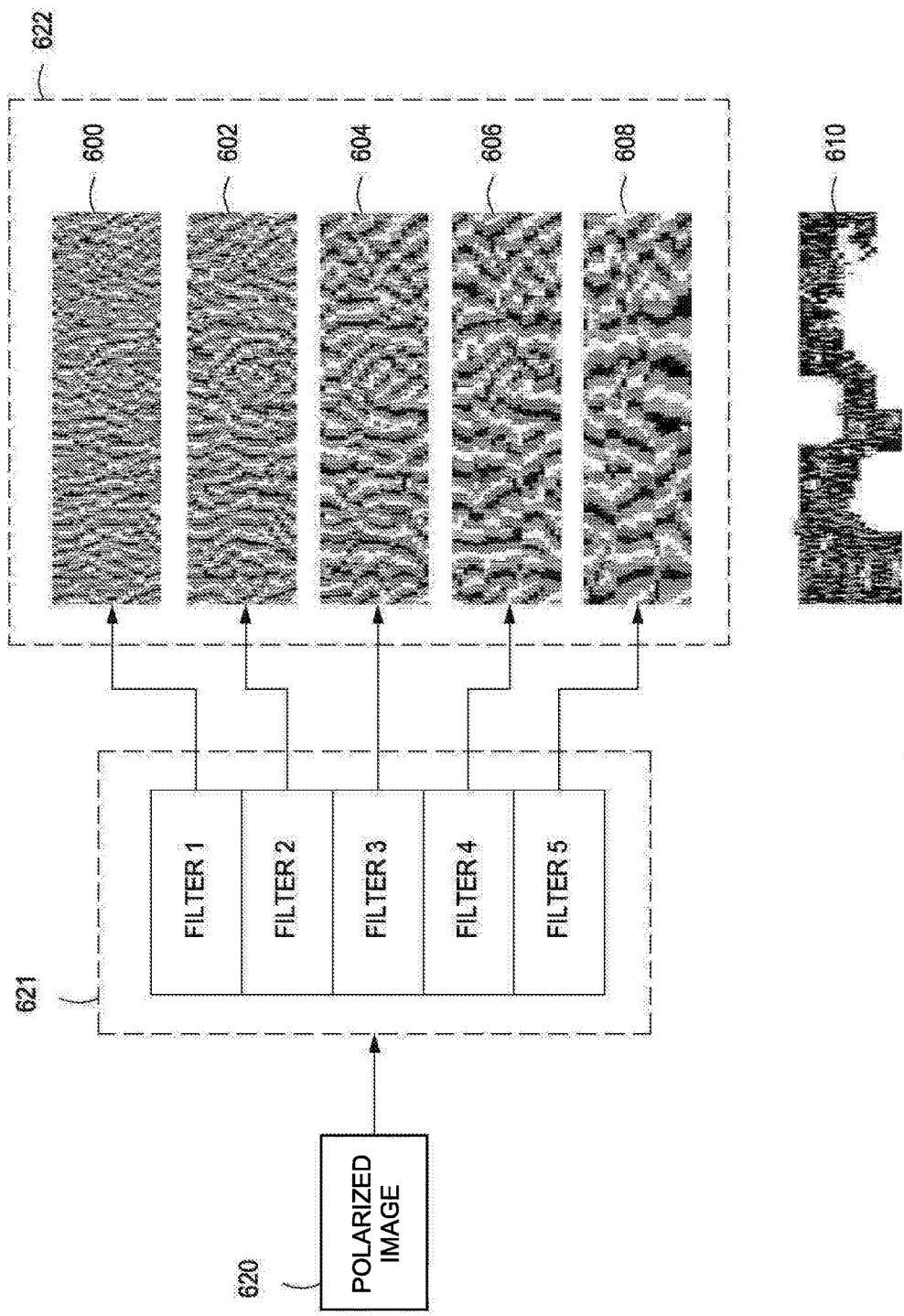
FIG. 6 depicts a simplified example of at least one embodiment of a multiresolution iris code as disclosed herein.

Subsequently, after converting the rectified iris image into a polar coordinate image, the image 504 is coupled to the extraction module 506 that filters and subsamples the polar iris image 504 to produce a multi-resolution iris code representation 520, an example of which is shown in FIG. 6. According to an exemplary embodiment, the image 504 is passed through a series of bandpass filters to produce a set of filtered images. FIG. 6 shows an example of a polar iris image 620, being filtered by filters 121 (Filters 1 . . . 5) and producing an iris code 622 comprising filtered bands 600, 602, 604, 606 and 608, respectively high-frequency domain bands to low frequency domain bands. The five bands shown correspond to Gabor filter (a linear filter used for harmonic analysis, wavelet decompositions, and edge detection) carrier wavelengths of 6, 8, 12, 16, and 24 pixels with respect to a polar image sampled at 200 pixels around the iris. Therefore, the frequencies correspond approximately to angular spatial frequencies of 33, 25, 16, 12, and 8 cycles per 2pi.

The higher frequencies are comparable to those used in standard iris matching algorithms. The mask 610 is the union of two masks: a mask (common to all bands) based on analysis of the intensities in the input polar iris image 504 that masks off area corresponding to specular reflections and approximate location of eyelid and eyelash areas, and a mask based on the signal strength in the Gabor filtered image that masks off areas in which local phase measurement is unstable (unstable regions). Multi-resolution representation as shown in iris code 622 allow representation of information from images at different camera-subject distances that result in iris images differing in number of pixels per unit distance at the iris as well as oblique camera views causing foreshortening and optical demagnification, as discussed above with reference to FIGS. 2-4D.

Other properties of an iris code representation 520 include a complete description of the filter characteristics, spatial sampling, representation and quantization. Filter characteristics comprise one or more of center frequencies, bandwidths, functional type (e.g. log Gabor), and orientation tuning Spatial sampling comprises one or more of spacing along the radial and angular normalized image axes for each filter type, and quantization specifies the number levels with which each value is represented or number of bits assigned to each. According to exemplary embodiments, the iris code representation 520 and exemplary iris code 622 is a warpable code allowing for interpolation by using sub-Nyquist spatial sampling requirements for each filter 1 . . . 5 in filters 621 that produces provide a criterion for sufficient sampling for accurate interpolation. The sub-Nyquist spatial sampling is combined with a finer intensity quantization than the 1 bit per complex phase component used in Daugman-type coding. For example, if 4 bits are used for each complex phase component this corresponds to roughly 64 steps in phase angle and thus a maximum interpolation error of pi/32 radians or less than six degrees.

In some embodiments, non-quantized iris codes may also be matched, where original complex band-pass filter outputs are stored without quantization. In one embodiment, the filter outputs are normalized in magnitude so that each represents a complex number on the unit circle. Data masks are generated based on occlusions and local complex amplitude. The match measure that is the closest analog of the standard Hamming Distance measure of a Daugman iris code is based on a phase difference histogram. This histogram constructed by computing the angles between the phase vectors of the two codes being compared (see FIG. 6), and compiling a histogram (subject to the valid data mask) of phase differences between -pi and pi. These phase differences should be small if the codes represent the same eye and more or less uniformly distributed if the codes represent statistically independent eyes.

Figure 7:
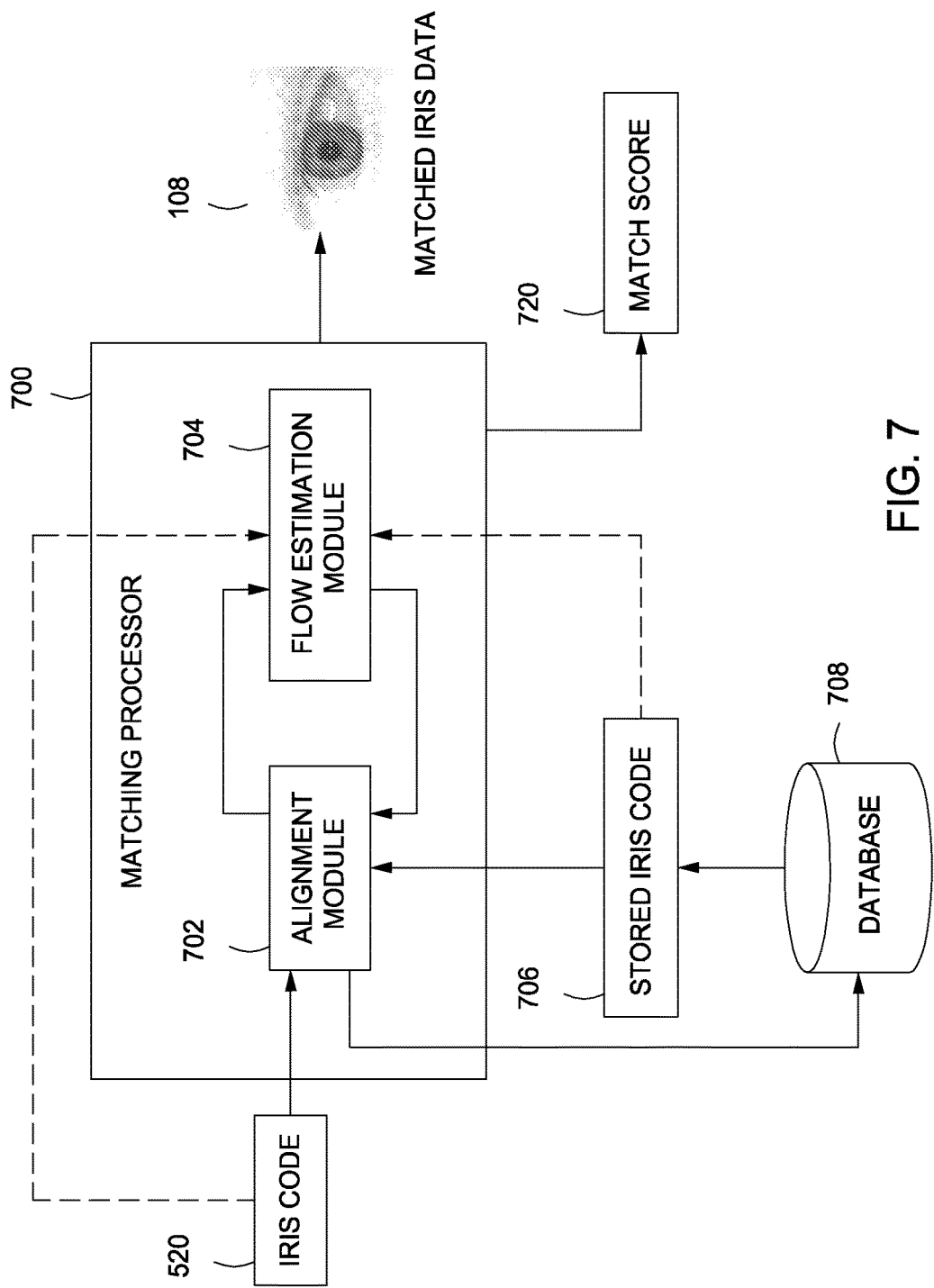
FIG. 7 depicts a simplified block diagram of at least one embodiment of a matching processor as disclosed herein.

An example of two such histograms is shown in FIG. 7. The histogram on the left corresponds to an impostor match and the one on the right to an authentic match. As expected, the authentic distribution is tightly concentrated around a zero phase shift with only a small proportion of the phase difference values larger than pi/2 in absolute value. In contrast, the impostor histogram shows many large phase differences and no clear evidence of concentration around zero value. The fraction of values larger than pi/2 can be used to generate a match statistic that behaves very much like Daugman code Hamming distance if this is desired. However, there are many other measures of central concentration and dispersion that may be used to distinguish between authentic and impostor distributions, as will be described below. Furthermore, give sufficient training sets of impostor and authentic histograms it may be beneficial to use statistical classification or machine learning techniques such as discriminant analysis, Support Vector Machines, Neural Networks, or Logistic Regression to construct an optimal decision procedure for some class of data.

Measurements of the central value of a phase difference histogram, and of the dispersion around that point takes into account the fact that the phase differences are angles and therefore the histogram is distributed on a closed circle. Ordinary mean and variance measures (or higher moments if necessary) do not correctly represent the desired properties for angular data. The Von Mises distribution provides a well characterized method for estimating properties of data distributed over a periodic domain. The Von Mises mean gives an estimate of the center of concentration of the distribution and the concentration parameter and estimate of the spread. Both quantities can be computed easily if the phase differences are represented as unit complex numbers. In this case, the mean estimate is simply the angle corresponding to the sample mean of the complex numbers, and the concentration parameter is simply related to the complex magnitude of the sample mean.

According to another embodiment, data is analyzed over a periodic domain by employing a Fourier series expansion to compute circular harmonics. Like the Von Mises parameters, the relative magnitude low order circular harmonics give information about degree of concentration of the data. Transformation of the histogram data using circular harmonics is beneficial prior to use of learning techniques to construct a decision procedure.

The phase difference histogram aids in analysis of the match level between two codes but does not represent all of the information relevant to the comparison of two codes. If the phase difference value varies as a function of the absolute phase then the histogram shows low concentration (i.e. large dispersion) even given a strong relationship. According to one embodiment, a Mutual Information or other conditional entropy description is employed to prevent this problem, which measures the reduction in the entropy of one random variable given knowledge of the value of another random variable. This more complete characterization can detect relatedness even where the variables are uncorrelated.

Another limitation of the phase difference histogram is that it completely suppresses spatial information since the histogram is a global statistic. However, local or patchwise uniformity of phase differences or other detectable relatedness would also be sufficient to conclude that the codes are not independent. This local analysis could be achieved using local histogram analysis, mutual information, or spatial correlation analyses.

FIG. 7 depicts a block diagram of a matching processor 700 in accordance with exemplary embodiments of the present invention. The matching processor 106 comprises an alignment module 702 and a flow estimation module 704. According to exemplary embodiments, the iris code 520 generated by the coding processor 500 as shown in FIG. 5 is coupled to the alignment module 702. The alignment module 702 performs various alignments to the iris code 520 based on matching algorithms described below. The alignment module 702 further couples the iris code 520 to the flow estimation module 704 to generate estimated flow vectors to aid in matching. The alignment module 702 compares the iris code 520 to an iris code 706 from database 708 to determine whether a match exists. If a match does not exist, more iris codes from the database 708 are compared with the iris code 520. Match scores are determined, and if the match score meets or is below a predetermined threshold, then a match exists. According to exemplary embodiments, a Hamming distance is used as a match score. Ultimately, the matched iris data 108 is returned by the matching processor 700. According to some other embodiments, flow estimation is applied to information derived from the unknown iris code 520 and the stored iris code 706. This information may be part of the iris code 520 per se or it may not. The resulting flow field from the flow estimation module 704 is used to generate a modified iris code that is matched against a reference iris code by the matching processor 700 to produce a match score 720.

In a binary context, i.e., comparing iris codes, a Hamming distance represents a binary distance based on XOR operations to computes the number of bits that differ between two binary images. According to exemplary embodiments, the alignment module 702 performs a Daugman barrel shift on the iris codes, i.e., finds the iris code rotation that provides the best match between the iris codes being compared. In one embodiment, the matching algorithm employed by the matching processor 700 is a modified algorithm using the Hamming distance (HD) for each set of barrel shift positions and taking the lowest Hamming distance as the score for that pair of codes. If the score is below some threshold (that may be adjusted based on the estimated number of statistical degrees of freedom represented by the codes) then the unknown code is deemed to be a match. If the HD is above the threshold then the unknown code is labeled an impostor. In one embodiment, the threshold depends on details of the iris code structure and on the statistical requirements of the matching scenario.

The modified algorithm employed by the alignment module 702 barrel shifts the iris codes being compared and also locally aligns the iris codes to each other to compensate for inaccuracies in iris image normalization due to uncorrected optical distortion or complexities of iris dilation and contraction. The local alignment function, performed by alignment module 702, allows compensation for distortions in the input iris image that are not uniform across the iris. This is accomplished by shifting local regions of the code to bring them into more accurate alignment with corresponding regions of the reference code. However, if this process is performed using very small estimation regions, virtually any iris code can be made to match any other iris code, which can result in false matches being generated. This false matching problem can be avoided by imposing suitable smoothness conditions on the estimated flow field. For example, if the flow field is estimated by performing local translation estimation using relatively large estimation regions then the local flow estimates will represent the average motion over this relatively large region.

If such region overlaps, so that the regions used to compute the flow vectors for neighboring locations contain much of the same content, then the displacement estimates will change gradually with position and false matching will be prevented. Alternatively, local displacement estimates made with small estimation regions can be smoothed by spatial filtering to eliminate rapid changes in local displacement. As a further alternative, a global parametric representation such as a low order polynomial or truncated Fourier series can be used, and the parameters of this parametric representation estimated directly or fit to local estimates. Such parametric representation has inherent smoothness properties that prevent too rapid change in local shifts to occur. The alignment module 702 further produces multiple match scores for each comparison, between iris code 520 and 706 for example, because each iris code contains multiple frequency bands.

Figure 8:
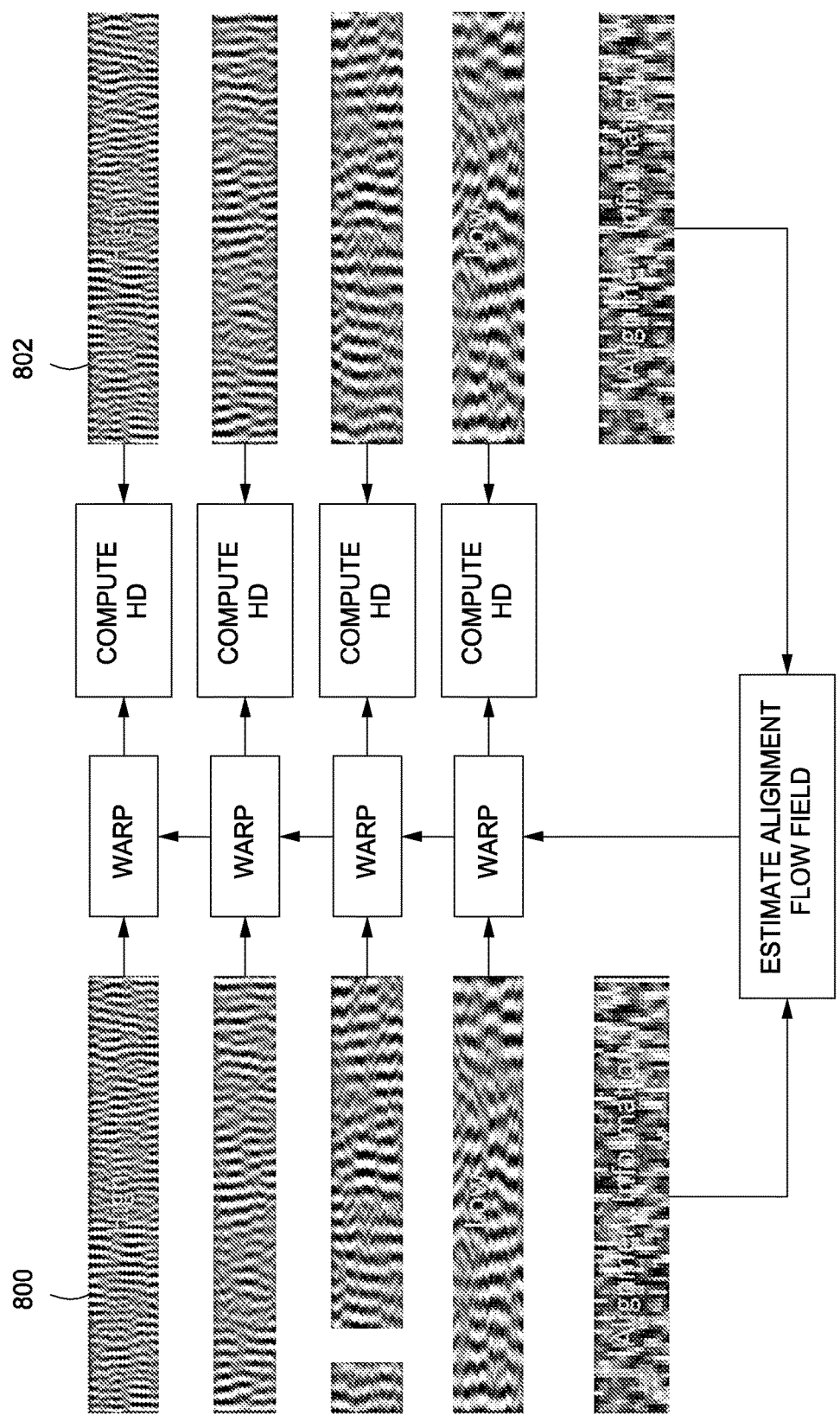
FIG. 8 depicts a simplified example of at least one embodiment of a process for matching iris codes, which may be performed by the matching processor of FIG. 7.

FIG. 8 depicts the process of matching iris codes performed by the matching processor 700 in accordance with exemplary embodiments of the present invention. As in standard iris code matching, the first code 800 and the second code 802 to be matched are represented as values over the rectified (e.g., polarized) iris image coordinate system consisting of an angular and a normalized radial coordinate. A local displacement function or flow field is computed by the flow estimation module 704 of the matching apparatus in FIG. 7 and coupled to the alignment module 702 that best aligns structure in the first iris code 800 to corresponding structure in the second code 802, subject to some smoothness or parametric constraint. This flow field estimation can include the effect of standard barrel shift alignment or that can be performed as a separate step. The vectors in this flow field each specify the displacement in the normalized image coordinate system at which the image structure in the first code 800 best matches the structure in the second code 802.

Each band in first iris code 800 is transformed using this displacement function to produce an aligned iris code, and the Hamming distance between this aligned iris code and the corresponding band of the second code 802 is computed. Because the transformation is constrained to be smooth, impostor codes will not be transformed into authentic codes as will be described below.

The flow estimation module 704 computes a flow field at a reduced resolution for each iris code, and smoothly interpolates the flow field to produce a final estimate. According to an exemplary embodiment, the flow estimation module 704 employs a pyramid-based coarse-fine flow estimation technique, though those of ordinary skill would recognize that other techniques may be used instead. The alignment module 702 introduces a small local shift in one band of each of the first iris code 800 and the second iris code 802, the shift being in the angular direction and equal at all radial positions. The displacement shift also varies smoothly in the angular direction. Calculating a Hamming distance at this point would result in a non-match (e.g., if a Daugman-type matching algorithm is employed a Hamming distance greater than 0.33 indicates a non-match). A coarse-fine algorithm is used by the flow estimate module 704 to estimate the flow field between codes 800 and 802 from the low resolution bands of the codes.

The alignment module 702 then warps the code 800 by the estimated flow field resulting in a significantly decreased Hamming Distance, signaling a high confidence match. For a Daugman-type matcher, a Hamming distance <0.3 indicates a high confidence match. Various matches may correspond with different Hamming distance values qualifying as high confidence matches. According to another embodiment, the matching processor 700 may match two iris codes by employing a mutual information measure based on the phase angles of the codes being compared as well as measures based on the local difference of phase angles.

Figure 9:
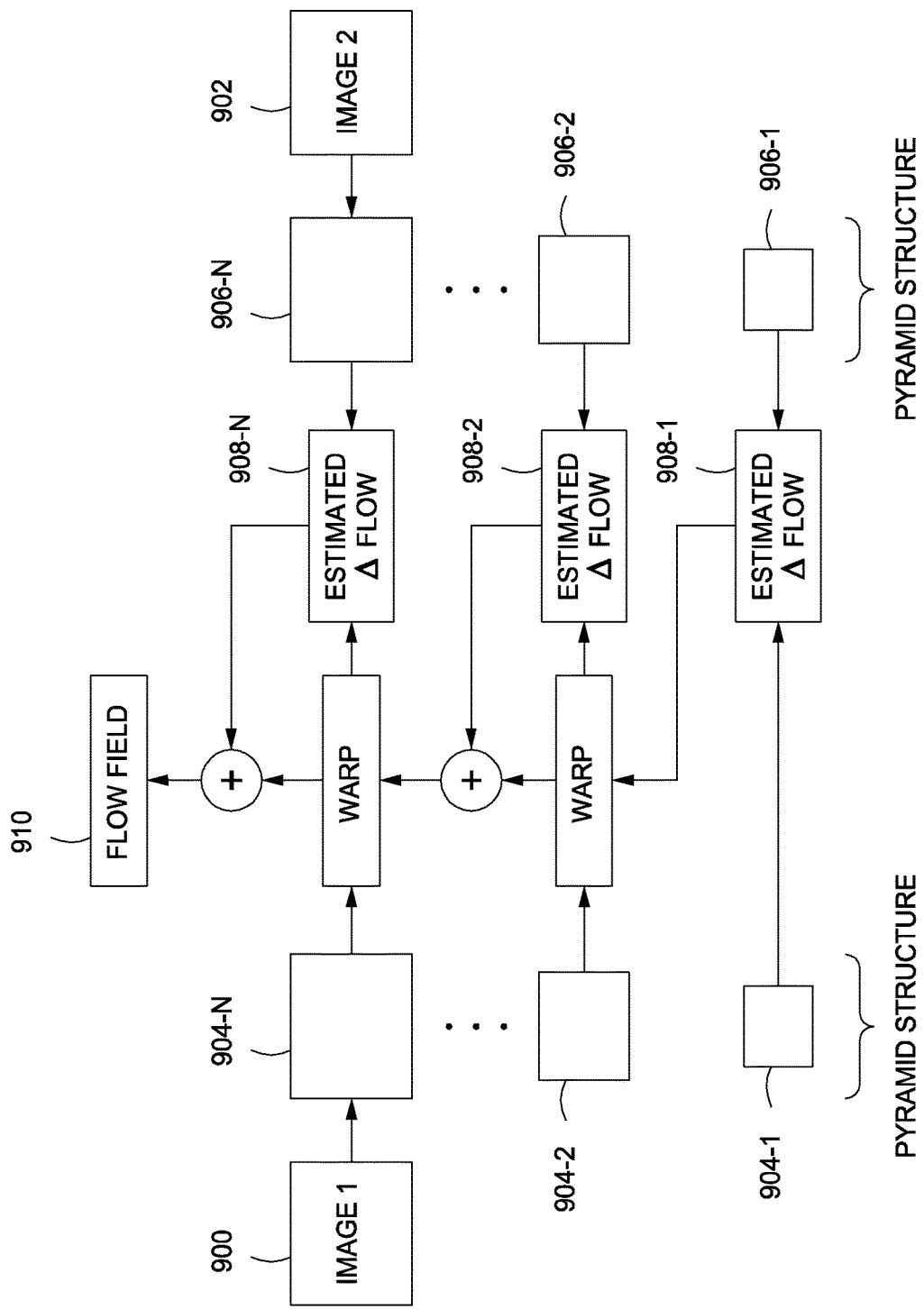
FIG. 9 is a simplified schematic depiction of a coarse-fine algorithm to estimate flow-field of an iris code, as disclosed herein.

FIG. 9 is a depiction of the coarse-fine algorithm described above to estimate flow-field of an iris code in accordance with exemplary embodiments of the present invention. Coarse-fine refinement operates on a "pyramid" structure that is essentially a collection of bandpass filtered version 904-1 to 904-N and 906-1 to 906-1 of the input images 900 and 902 respectively, as shown in FIG. 9.

Starting with the lowest frequency bands 904-1 and 906-1, at each level in the pyramid the displacements 908-1 to 908-N estimated at the previous level are used to warp the current level image and then an incremental displacement is computed based on the residual difference between the warped level and the corresponding pyramid level in the other image. This process continues until the highest level is reached and the result is the final estimated flow field 910.

Since the multi-resolution iris code is itself a collection of bandpass filtered versions of the images with which alignment is desired, according to one embodiment, these bands themselves could be used to drive the alignment process in the alignment module 702. This would produce a truly "self aligning" iris code. In this approach there is no need to store additional alignment data as part of the multi-resolution iris code structure.

Figure 10:
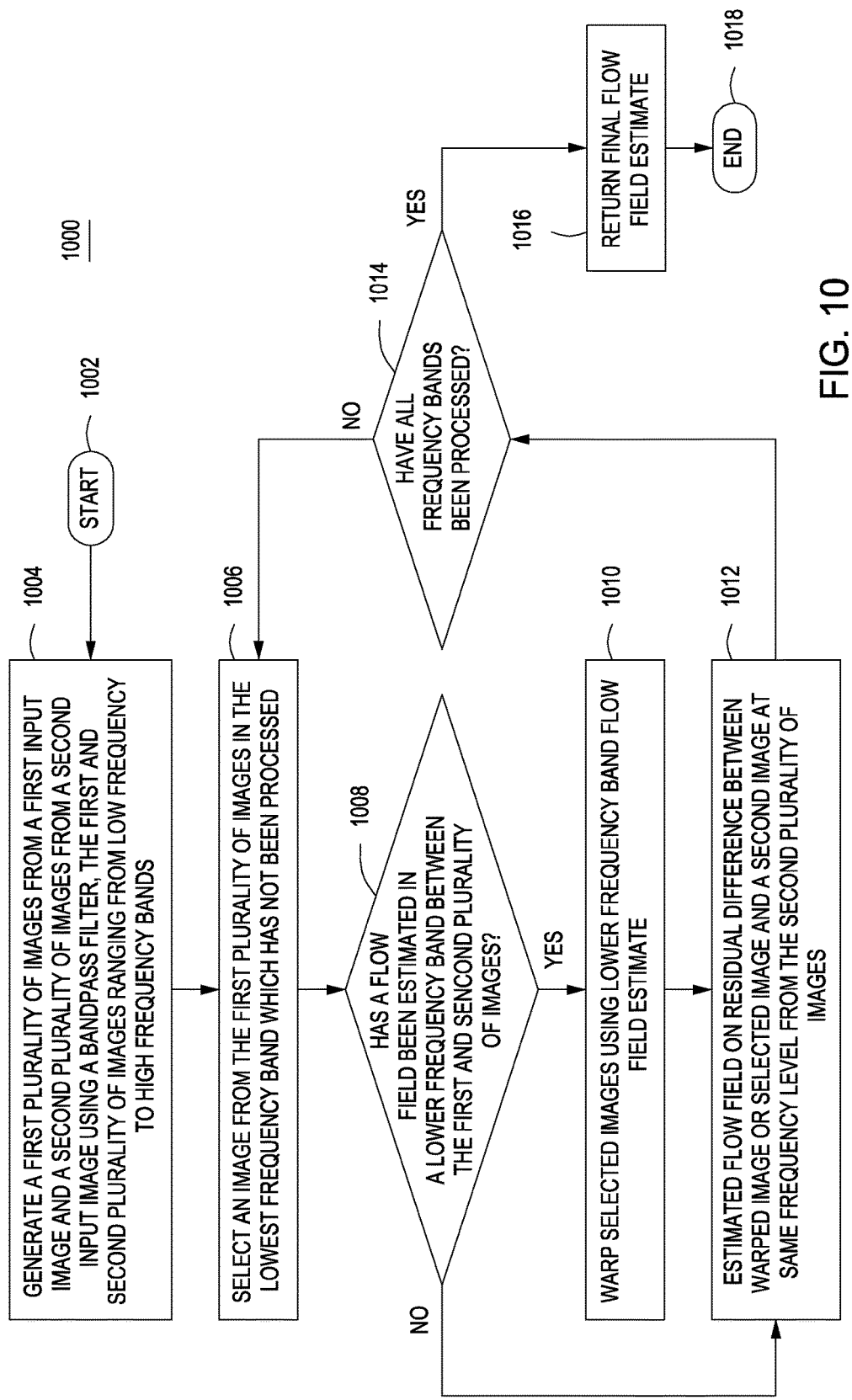
FIG. 10 is a simplified flow diagram depicting at least one embodiment of a method for estimating flow field between two iris codes, as disclosed herein.

FIG. 10 is a flow diagram depicting method 1000 for estimating flow field between two iris codes in accordance with exemplary embodiments of the present invention. The method is an implementation of the flow estimation module 704. The method begins at step 1002 and proceeds to step 1004.

At step 1004, the flow estimation module 704 generates a first plurality of images from a first input image (i.e., a first iris code) and a second plurality of images from a second input image (i.e., a second iris code to be matched against) using a bandpass filter, the first and second plurality of images comprising images ranging from low frequency to high frequency bands.

The method subsequently proceeds to step 1006, where the flow estimation module 704 selects an image from the first plurality of images in the lowest frequency band that has not been processed, i.e., for which there is no previous flow-field estimate. At step 1008, the flow estimation module 704 determines whether a flow field has been estimated in a lower frequency band between the first and second plurality of images. If a flow field has been estimated in a lower frequency band, the method proceeds to step 1010, where the selected image is warped using the lower frequency band flow field estimate. If a flow field estimate in a lower frequency band has not been estimated, then the method proceeds to step 1012, where a flow field is estimated by the flow estimation module 704 on the residual difference between the warped image and a second image at the same frequency band from the second plurality of images.

The method then proceeds to step 1014, where the flow estimation module 704 determines whether all frequency bands have been processed. If not, then the method returns to step 1006 to process the next higher frequency band until all frequency bands have been processed. When all frequency bands have been processed (i.e., warped by lower frequency flow field estimates), the method proceeds to step 1016, where the final flow field estimate is returned to the matching processor 700. The method terminates at step 1018.

Figure 11:
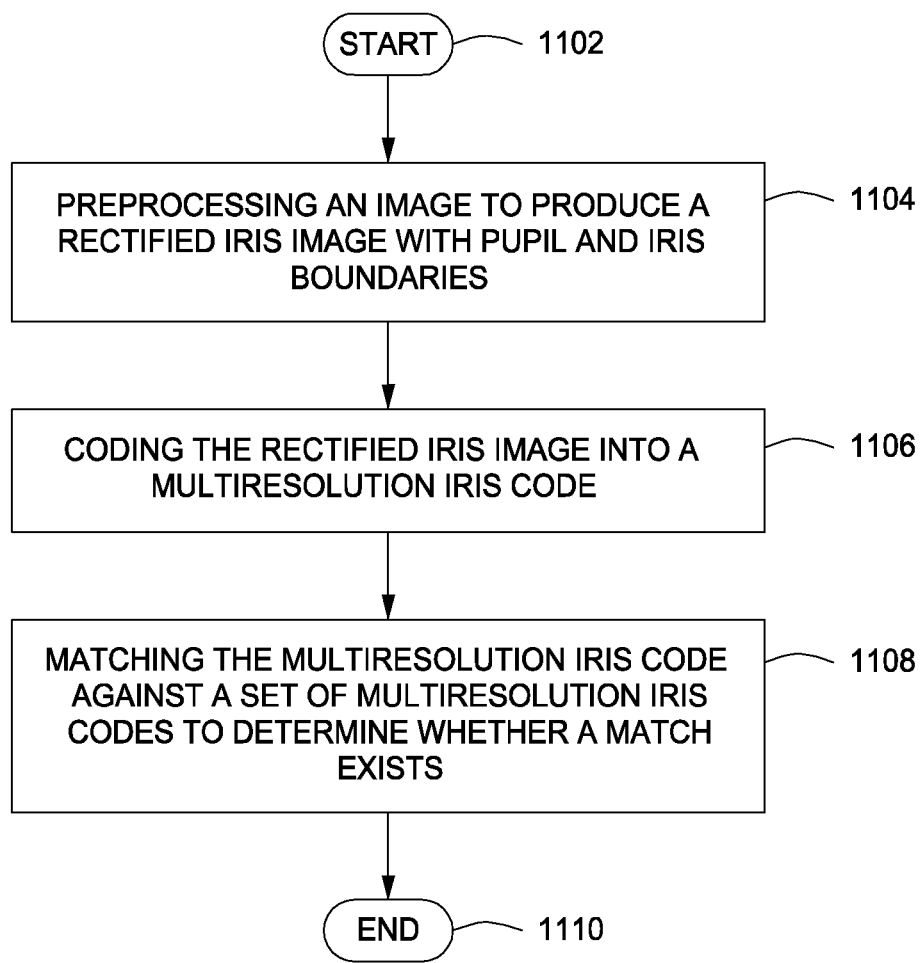
FIG. 11 is a simplified flow diagram depicting at least one embodiment of a method for estimating flow field between two iris codes as disclosed herein.

FIG. 11 is a flow diagram depicting method 1100 for estimating flow field between two iris codes in accordance with exemplary embodiments of the present invention. The method is an implementation of the iris processor 100. The method begins at step 1102 and proceeds to step 1104.

At step 1104, the pre-processor 102 pre-processes and input image containing an eye to produce a rectified iris image with rectified pupil and iris boundaries, and correction for tilt and corneal distortion.

The method proceeds to step 1106, where the coding processor 104 codes the rectified iris image into a multi-resolution iris code. The iris code contains multiple frequency band representations of a polarized version of the rectified iris image. The method then proceeds to step 1108, where the multiresolution iris code is compared to a set of stored iris codes in a database to determine whether the iris code is contained in the database and returns data associated with the matched iris. The method terminates at step 1110.

Figure 12:
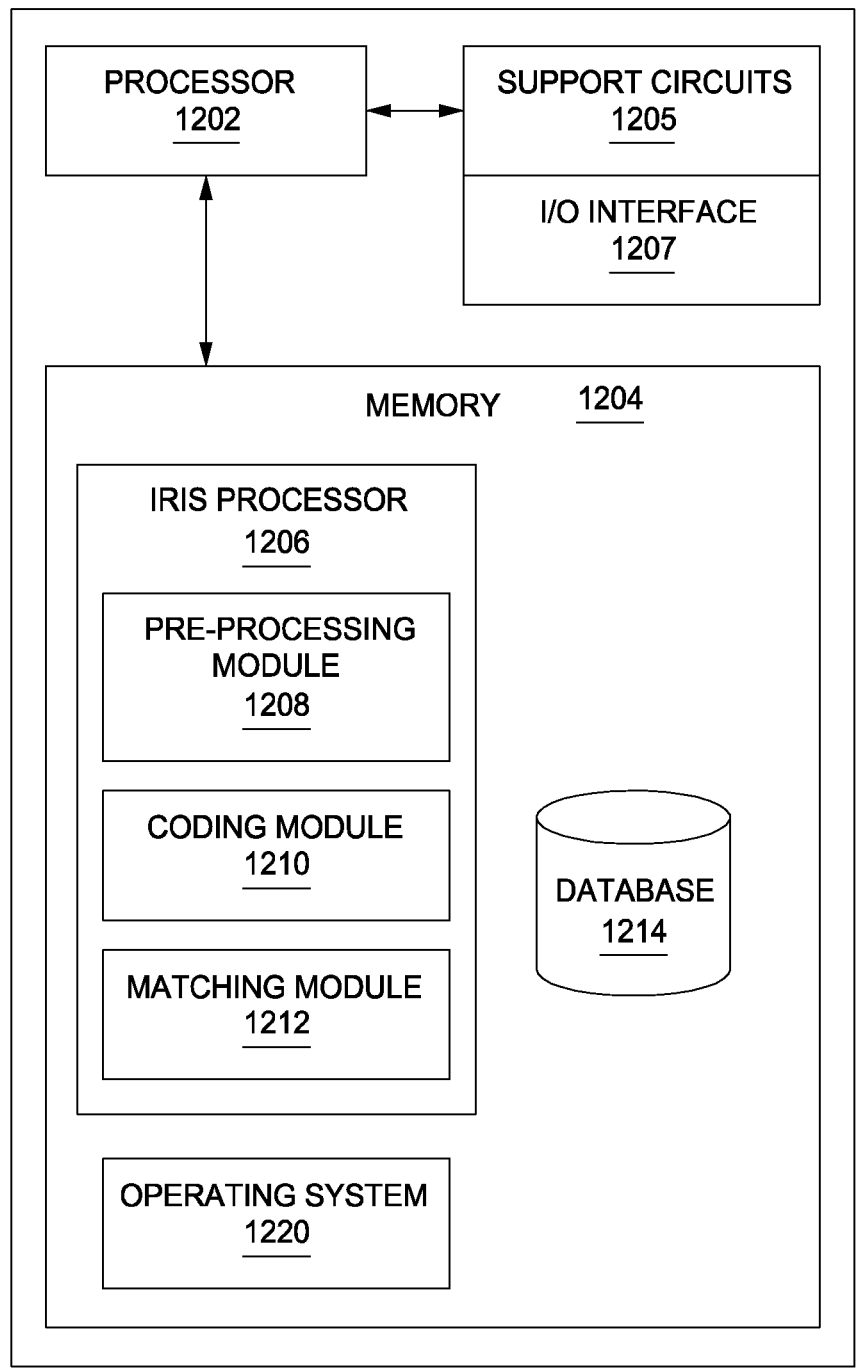
FIG. 12 depicts a simplified schematic diagram of at least one embodiment of a computer system for implementing the iris processor of FIG. 1, as disclosed herein.

FIG. 12 depicts a computer system for implementing the iris processor 100 in accordance with exemplary embodiments of the present invention. The computer system 1200 includes a processor 1202, various support circuits 1205, and memory 1204. The computer system 1200 may include one or more microprocessors known in the art similar to processor 1202. The support circuits 1205 for the processor 1202 include conventional cache, power supplies, clock circuits, data registers, I/O interface 1207, and the like. The I/O interface 1207 may be directly coupled to the memory 1204 or coupled through the support circuits 1205. The I/O interface 1207 may also be configured for communication with input devices and/or output devices such as network devices, various storage devices, mouse, keyboard, display, video and audio sensors, visible and infrared cameras and the like.

For example, in embodiments where the computer system comprises a mobile device such as a cell phone or tablet, I/O interfaces 1207, such as an integrated camera (possibly used in association with an on-board standard and/or infrared illumination device) or a wireless communication device (e.g., CNFC, RFID, Bluetooth, Wi-Fi, Wimax, Satcom, etc.), may be directly coupled to the memory 1204 and/or coupled through the support circuits 1205. In some embodiments, one or more software applications or apps may be configured to access the camera, illuminator and/or wireless communication device to accomplish the embodiments disclosed herein. In these embodiments, the apps may receive data (e.g., iris data) via the I/O interface 1207 and transmit the data, possibly via the support circuits 1205 to the memory 1204 running the app (e.g., Iris Processor 100 or Iris Biometric Recognition Module 1514). The app may perform any of the algorithms disclosed herein, and transmit the results (possibly via memory 1204 and/or support circuits 1205) to the I/O interfaces 1207 (e.g. via wireless communication) to a server and/or an additional wireless communication device (e.g., an ATM or security-enabled device such as a safe), to authenticate a user of the device.

The memory 1204, or computer readable medium, stores non-transient processor-executable instructions and/or data that may be executed by and/or used by the processor 1202. These processor-executable instructions may comprise firmware, software, mobile apps, and the like, or some combination thereof. Modules having processor-executable instructions that are stored in the memory 1204 comprise an iris processor 1206. The iris processor 1206 further comprises a pre-processing module 1208, a coding module 1210 and a matching module 1212. The memory 1204 may further comprise a database 1214, though the database 1214 need not be in the same physical memory 1204 as the iris processor 1206. The database 1214 may be remotely accessed by the iris processor 1206 via a cloud service. Additionally, the iris processor 1206 may also have several components that may not be co-located on memory 1204. For example, in some embodiments, the pre-processing module 1208 is local to the computer system 1200 or mobile device, while the coding module 1210 and the matching module 1212 may be accessed as cloud services via a wired or wireless network. In other instances, only the matching module 1212 is accessed via a network. Communication between each module may be encrypted as the data travels over the network.

The computer system 1200 may be programmed with one or more operating systems 1220 (generally referred to as operating system (OS)), that may include OS/2, Java Virtual Machine, Linux, SOLARIS, UNIX, HPUX, AIX, WINDOWS, WINDOWS95, WINDOWS98, WINDOWS NT, AND WINDOWS2000, WINDOWS ME, WINDOWS XP, WINDOWS SERVER, WINDOWS 8, Mac OS X, IOS, ANDROID among other known platforms. At least a portion of the operating system may be disposed in the memory 1204.

The memory 1204 may include one or more of the following random access memory, read only memory, magneto-resistive read/write memory, optical read/write memory, cache memory, magnetic read/write memory, and the like, as well as signal-bearing media as described below.

The computer system 1200 may be a mobile device such as a cellular phone or tablet device, for example. The mobile device may contain a camera and have the iris processor 1206 stored on memory as an application. In some embodiments, the iris processor 1206 may be a part of the operating system 1220. In some instances, the iris processor 1206 may be an independent processor, or stored on a different chip than the processor 1202. For example, often mobile devices have camera processing modules and the iris processor 1206, or portions of the iris processor 1206, may reside on the camera processing module, where the imager in the camera is a CCD or CMOS imager. In some instances, the mobile device may be customized to include some sensors, the type of the camera imager, or the like.

An image sensor may include a camera or infrared sensor or illuminator that is able to project images or other objects in the vicinity of the device. It should be understood that image capture can be performed using a single image, multiple images, periodic imaging, continuous image capturing, image streaming, etc. Further, a device can include the ability to start and/or stop image capture, such as when receiving a command from a user, application, or other device. The computing device can include one or more communication elements or networking sub-systems, such as a Wi-Fi, Bluetooth, radio frequency (RF), wired, or wireless communication system. The device in many embodiments can communicate with a network, such as the Internet, and may be able to communicate with other such devices. In some embodiments the device can include at least one additional input element able to receive conventional input from a user. This conventional input can include, for example, a push button, touch pad, touchscreen, wheel, joystick, keyboard, mouse, keypad, or any other such component or element whereby a user can input a command to the device. In some embodiments, however, such a device might not include any buttons at all, and might be controlled only through a combination of visual and audio commands, such that a user can control the device without having to be in contact with the device.

Figure 13:
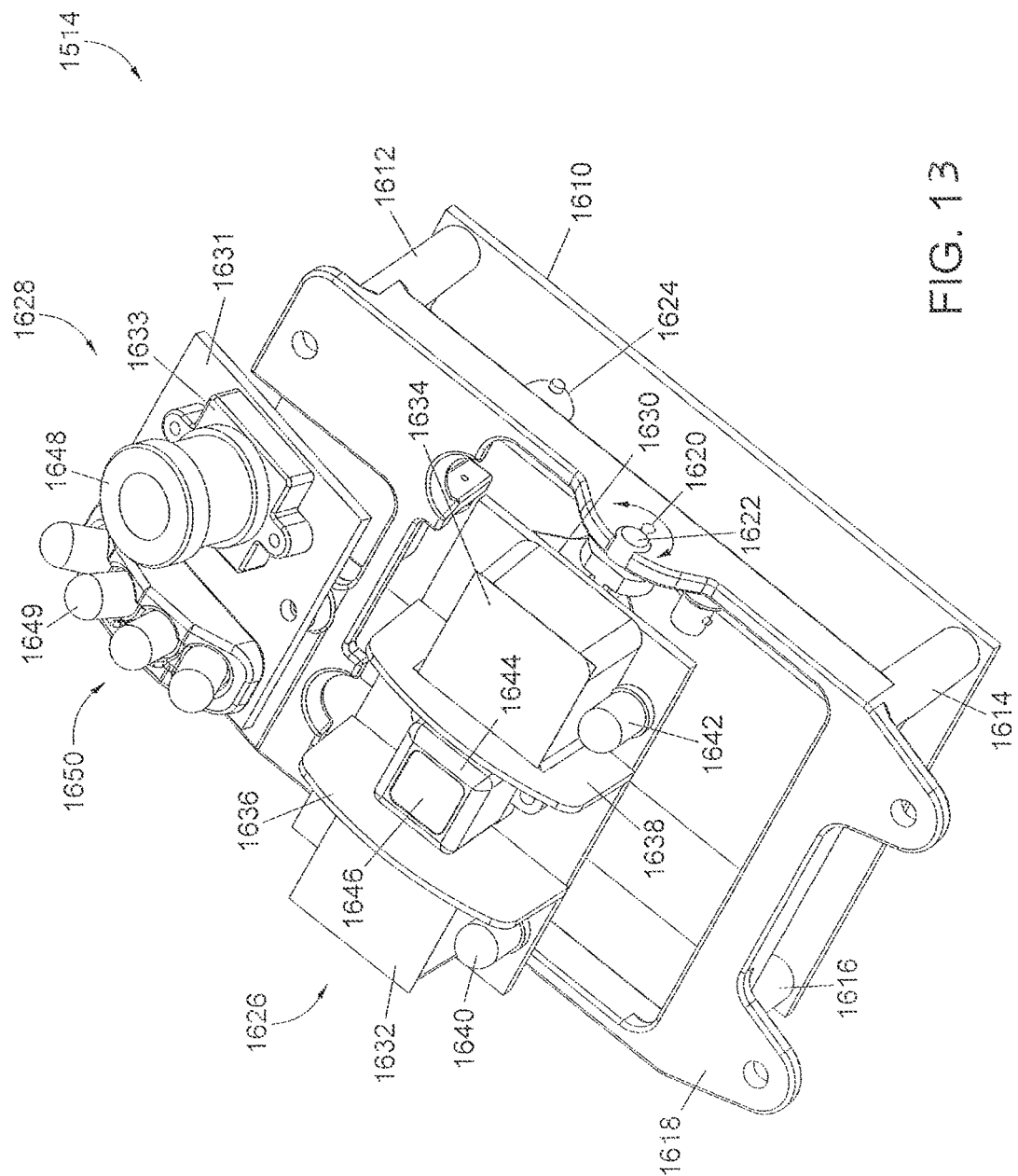
FIG. 13 is a simplified assembled perspective view of at least one embodiment of an iris biometric recognition module.
Figure 14:
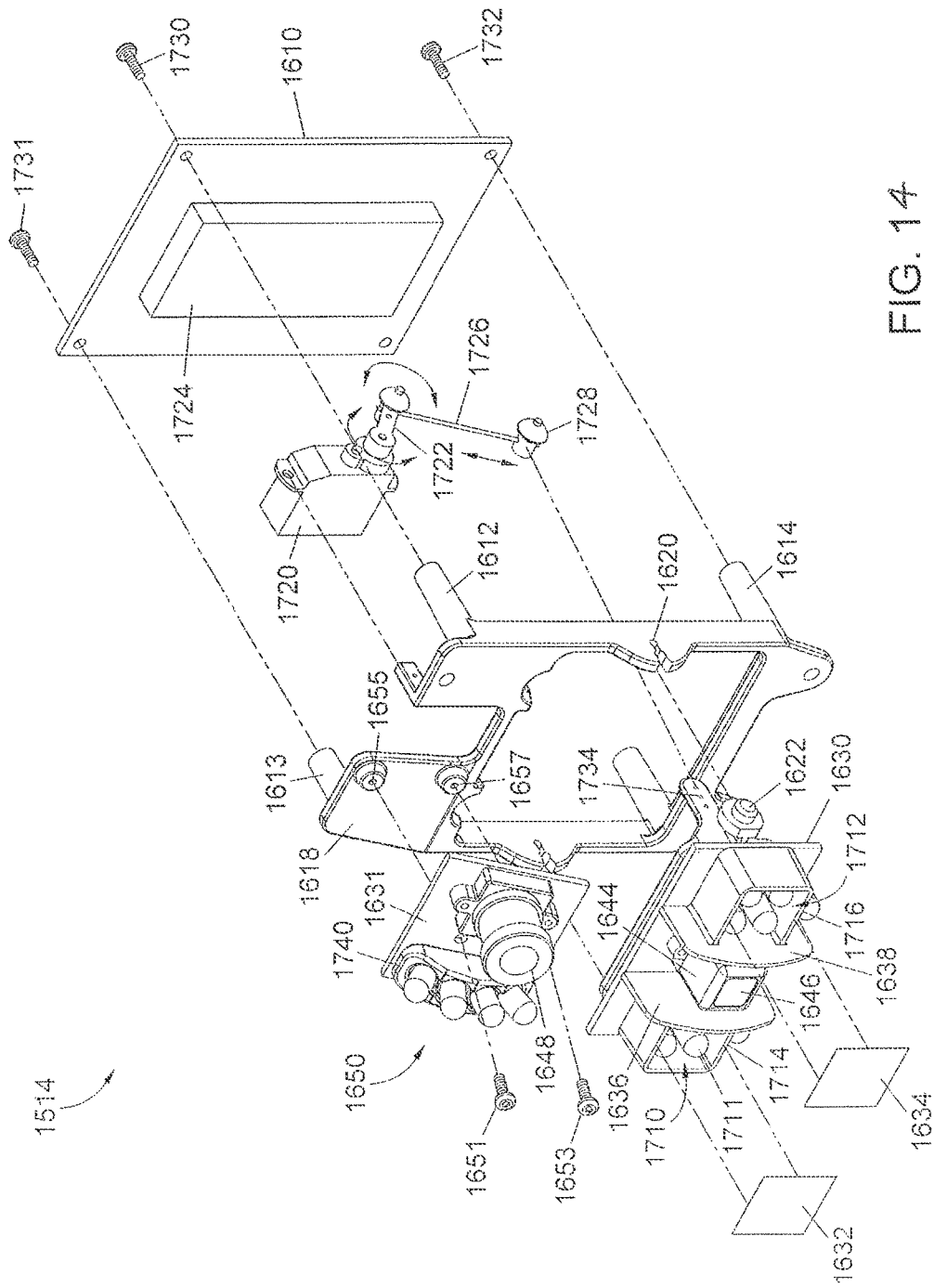
FIG. 14 is an exploded perspective view of the iris biometric recognition module of FIG. 16.

Referring now to FIGS. 13 and 14, an illustrative iris biometric recognition module 1514 is shown in greater detail. As shown in FIG. 13, when assembled, the iris biometric recognition module 1514 is a self-contained unitary module. As such, the iris biometric recognition module 1514 can be incorporated into, for example, a security or locking features, for example a door lock assembly, or any other type of device, apparatus, article, or system that can benefit from an application of iris biometric recognition technology, including, for example, a mobile device, a mobile device compatible with wireless communication, an electronic device used in a financial transaction and/or an electronic advertisement display device.

In an exemplary embodiment, the biometric recognition module 1514 may be integrated into, mounted on and/or otherwise coupled to an electronic item or device, for example, a computer or a mobile device (e.g., a laptop, a mobile telephone, a tablet, a watch or other accessory storing and/or displaying information or data or any other mobile device), in order to confirm that the user controlling the computer or mobile device is a user authorized to operate the device and any of the apps running on the device. The incorporation of an Iris Processor 100 and/or Iris Biometric Recognition Module 1514 within the device, for example, a mobile device, allows the mobile device to match the received iris biometric information to a template stored in a database, thereby allowing the mobile device or any associated hardware or software, at a certain time, to identify and/or authenticate the user and/or create a biometric record that the user was authorized to access the mobile device at a specific time.

In addition to providing access to the mobile device and its applications generally, the iris biometric recognition module 1514 may be incorporated into an electronic item or device in order to authenticate the user to allow access to the wireless communication capabilities of the wireless device (NFC, Bluetooth, RFID, WiFi, WiMax, Satcom, etc), in order to communicate with another wireless communication capable devices to exchange information that would allow an event, task, or transaction to be completed.

The wireless communication device contained in a mobile device may be authorized for use by the operator of the device, after iris biometric authentication, to activate an application that directs the wireless communication device to complete a defined event, task, or transaction (authorize a payment, open a door, gain access to information, etc.). Once the identity of the user is validated, applications that leverage the wireless communication device may be activated for a limited time period to allow the user to complete an event, task, or transaction associated with using the wireless communication device.

In some embodiments, the accurate biometric identification used to authenticate the user may further provide access to any utilized wireless capabilities integrated into the mobile device. For example, if a user desired to use the mobile device to transmit a wireless communication to a second device (e.g., another mobile device, an ATM machine, or any other electronic device necessitating authentication) enabled for wireless communication, the user would authenticate themselves via iris biometric authentication, and once authenticated, would be enabled to transmit a wireless communication to the second device. Although additional biometrics may be used, the iris biometric method of authentication may be superior to other currently utilized methods of authentication, including PINS, swipes, and other biometrics.

As another example, if the user wants to unlock a door with a NFC device as the receiver, the user would authenticate his identify on his mobile device, which would enable an application on the mobile device that can be used to transmit a unique code from the NFC device on his mobile device to the door lock device to unlock the door. Once the event is completed, the NFC may be locked and, if the user wants to perform another action that requires the NFC, he would be required to again authenticate his identity to enable the applications associated with the NFC. The door lock device or other lock device may be on a cabinet, safe, box, medical equipment container, residence, office, blood supply container, liquor cabinet, gun cabinet, jewelry box, locker, vehicle, or any other device, container, or object to be secured.

In an exemplary embodiment, the integration of the biometric recognition module 1514 in, for example, a computer, mobile device, or any other electronic device, may be applied to a financial transaction originating from a software application. The biometric authentication of the user to operate, for example, a mobile device, may occur using iris biometric recognition, as described above (rather than entering a PIN or password, as is typical of authenticating financial transactions), and the software application used to request the financial transaction may be accessed. Once the identity of the user is validated, the ability to complete the financial transaction may be activated for a limited time period to allow the user to complete an event, task, or transaction. Once the event, task, or transaction is completed, the software application and/or electronic device may be locked and, if the user wants to perform another financial transaction that requires the iris biometric recognition, he would be required to again authenticate his identity to enable the application. The biometric collection device described may be used alone or in conjunction with other authentication techniques (PIN, pattern, different biometric, etc.) if multi-levels of authentication are desired.

In an exemplary embodiment, the user may be authenticated to access a device using wireless technology in order to complete a financial transaction. As a non-limiting example, a user may be authenticated to access a mobile device running a financial software application used to complete financial transactions. This software application may also access the wireless communication capabilities of the mobile device in order to transmit information for the financial transaction to, for example, an ATM that also has wireless communication capabilities. After authentication of the user, the user may be authorized to complete the transaction and transmit the data for the transaction, via the wireless communication capabilities in the mobile device, to complete the transaction via the ATM. The transaction may be authorized through iris biometric recognition and/or any data or other information (e.g., a withdrawal amount, a transaction selection, etc.) may be entered, for example, through the mobile device or, for example, an application on the mobile device. In such situations, iris biometric recognition would allow completion of the transaction, for example, at the ATM, without pressing a single button in the ATM. One skilled in the art will understand that iris biometric recognition could similarly be implemented within any electronic device to conduct any type of event, task, or transaction, for example, in ticket machines, kiosks, payment machines, or any other electronic devices.

In embodiments that are not integrated into or attached and coupled to the structure, memory and circuitry of a mobile device, the iris biometric recognition module 1514 includes a support base 1610, to which an iris biometric recognition controller 1724 is mounted. A number of support posts, e.g., posts 1612, 1613, 1614, 1616, are coupled to the support base 1610 (by, e.g., a corresponding number of screws or other fasteners 1730, 1731, 1732, 1733) (1733 not shown). The support posts 1612, 1613, 1614, 1616 are connected to and support a pivot mount base 1618.

Coupled to and supported by the pivot mount base 1618 are an iris imager assembly 1626 and a face imager assembly 1628. In some embodiments, the iris imager assembly 1626 and the face imager assembly 1628 are the same device or utilize one or more of the same components (e.g., the same imaging device). However, in the illustrative embodiment, the iris imager assembly 1626 and the face imager assembly 1628 are separate assemblies utilizing different components. As described in more detail below, the face imager assembly 1628 captures digital images of a human subject, and more particularly, images of the subject's face and eyes, using a face imager 1648 that is equipped with a wide field of view lens. The iris imager assembly 1626 captures digital images of an iris of an eye of the human subject using an iris imager 1644 that is equipped with a narrow field of view lens. In some embodiments, both the face imager 1648 and the iris imager 1644 utilize the same type of imager (e.g., a digital camera, such as the Omnivision model no. OV02643-A42A), equipped with different lenses. For example, the face imager 1648 may be equipped with a wide field of view lens such as the Senview model no. TN01920B and the iris imager 1644 may be equipped with a narrow field of view lens such as model no. JHV-8M-85 by JA HWA Electronics Co. In other embodiments, a single high resolution imager (e.g., a 16+ megapixel digital camera) may be used with a wide field of view lens (rather than a combination of two cameras with different lenses) to perform the functionality of the iris imager 1644 and the face imager 1648.

The illustrative iris imager assembly 1626 is pivotably coupled to the pivot mount base 1618 by an axle 1622. The axle 1622 is e.g. removably disposed within a pivot groove 1620. The pivot groove 1620 is defined in the pivot mount base 1618. The components of the iris imager assembly 1626 are mounted to an iris pivot mount base 1630. The iris pivot mount base 1630 is coupled to the axle 1622 and to a support tab 1734. The support tab 1734 is coupled to a lever arm 1726 by a pivot link 1728. The lever arm 1726 is coupled to a control arm 1722. The control arm 1722 is driven by rotation of an output shaft of a motor 1720. The motor 1720 may be embodied as, for example, a servo motor such as a magnetic induction brushless servo motor (e.g., the LTAIR model no. D03013). Operation of the motor 1720 rotates the control arm 1722, which causes linear motion of the lever arm 1726, resulting in linear motion of the tab 1734. The linear motion of the tab 1734 rotates the axle 1622 in the pivot groove 1620. Depending on the direction of rotation of the output shaft of the motor 1720, the resulting rotation of the axle 1622 in the pivot groove 1620 causes the iris pivot mount base 1630 to tilt in one direction or the other, with respect to the pivot mount base 1618. For example, clockwise rotation of the motor output shaft may result in the iris pivot mount base 1630 tilting in an upwardly direction toward the face imaging assembly 1628 and vice versa. This pivoting capability of the iris pivot mount base 1630 enables the position of the iris imaging assembly 1626 to be mechanically adjusted to accommodate potentially widely varying heights of human subjects (e.g., the human subject 1424), ranging from small children to tall adults. In other embodiments, however, the iris imager assembly 1626 is stationary with respect to the pivot mount base 1618 and the ability to detect the irises of human subjects of widely varying heights is provided by other means, e.g., by software or by the use of a column of vertically-arranged iris imagers 1644 coupled to the mount base 1618.

The components of the iris imaging assembly 1626 include the iris imager 1644, a filter 1646 disposed on or covering the iris imager 1644, a pair of iris illuminator assemblies 1710, 1712 each adjacent to, e.g., disposed on opposite sides of, the iris imager 1644, and a pair of baffles or light guides 1636, 1638 disposed between the each of the iris illuminator assemblies 1710, 1712, respectively, and the iris imager 1644. Each of the illustrative iris illuminator assemblies 1710, 1712 includes one or more infrared light sources, e.g., infrared light emitting diodes (LEDs). In the illustrative embodiment, each iris illuminator assembly 1710, 1712 includes a number "N" of illuminators 1711, where N is a positive integer. While N=4 for both of the iris illuminator assemblies 1710, 1712 in the illustrative embodiment, the number N may be different for each assembly 1710, 1712 if required or desirable for a particular design of the iris biometric recognition module 1514. Each set of N illuminators is bounded by an additional light guide or shield 1714, 1716. Diffusers 1632, 1634 cover the iris illuminator assemblies 1710, 1712, respectively. For example, the diffusers 1632, 1634 may be coupled to the shields 1714, 1716 respectively (e.g., by an adhesive material). In the illustrative embodiments, the diffusers 1632, 1634 correct for the inherent non-uniformity of the light emitted by the illuminators 1711 (e.g., uneven lighting). This non-uniformity may be due to, for example, manufacturing irregularities in the illuminators 1711. As such, the diffusers 1632, 1634 may not be required in embodiments in which higher quality illuminators (or different types of illuminators) 1711 are used.

Although not specifically required for purposes of this disclosure, the illustrative iris imaging assembly 1626 further includes a pair of visual cue illuminators 1640, 1642, which are embodied as emitters of light having a wavelength in the visible light spectrum (e.g., colored light LEDs). The baffles 1636, 1638 and the shields 1714, 1716 are configured to prevent stray light emitted by the illuminator assemblies 1710, 1712 (and, for that matter, the visual cue LEDs 1640, 1642) from interfering with the operation of the iris imager 1644. That is, the baffles 1636, 1638 and the shields 1714, 1716 help ensure that when infrared light is emitted by the illuminator assemblies 1710, 1712, only the emitted light that is reflected by the eyes of the human subject (e.g., human subject 1424) is captured by the iris imager 1644. Additionally, a filter 1646 covers the lens of the iris imager 1644. The filter 1646 further blocks any extraneous light from entering the lens of the iris imager 1644. The filter 1646 may be embodied as, for example, an 840 nm narrow-band filter and may be embedded in the lens assembly of the iris imager 1644. In other embodiments, other types of filters may be used, depending on the type of illuminators selected for the illuminator assemblies 1710, 1712. In other words, the selection of the filter 1646 may depend on the type or configuration of the illuminator assemblies 1710, 1722, in some embodiments.

The illustrative face imager assembly 1628 includes a face imager mount base 1631. The illustrative face imager mount base 1631 is non-pivotably coupled to the pivot mount base 1618. In other embodiments, however, the face imager mount base 1631 may be pivotably coupled to the pivot mount base 1618 (e.g., the face imager assembly 1628 and the iris imager assembly 1626 may both be mounted to the pivot mount 1630), as may be desired or required by a particular design of the iris biometric recognition module 1514. The face imager assembly 1628 includes the face imager 1648 and a face illuminator assembly 1650 located adjacent the face imager assembly 1628. The face imager assembly 1628 and the iris imager assembly 1626 are illustratively arranged so that the face imager assembly 1628 is vertically above the iris imager assembly 1626 when the iris biometric recognition module 1514 is mounted to a vertical structure (such as the door 1416). In other words, the face imager assembly 1628 and the iris imager assembly 1626 are arranged so that the face imager assembly 1628 is positioned adjacent to a first edge of the pivot mount base 1618 and the iris imager assembly 1626 is positioned adjacent to another edge of the pivot mount base 1618 that is opposite the first edge.

The face imager 1648 is secured to the face imager mount base 1631 by a bracket 1633. The face illuminator assembly 1650 includes one or more infrared light sources 1649 (e.g., infrared LEDs) mounted to a concavely shaped illuminator mount base 1740. In the illustrative embodiment, the face illuminator assembly 1650 includes a number "N" of illuminators 1649, where N is a positive integer (e.g., N=4). The configuration of the mount base 1740 enables the illuminators 1649 to be arranged at an angle to one another, in order to illuminate the desired portion of the capture zone (e.g., the range of vertical heights H1 of the eye levels of the anticipated population of human subjects 1424). The illuminators 1649 of the face illuminator assembly 1650 and the illuminators 1711 of the iris illuminator assemblies 1710, 1712 may each be embodied as a high power 840 nm infrared emitter (e.g., model no. OV02643-A42A available from OSRAM Opto Semiconductors).

The illustrative iris biometric recognition controller 1724 is embodied as an integrated circuit board including a microprocessor (e.g., model no. MCIMX655EVM10AC available from Freescale Semiconductor). The iris biometric recognition controller 1724 is configured to control and coordinate the operation of the face illuminator assembly 1650, the face imager 1648, the iris illuminator assemblies 1710, 1712, and the iris imager 1644, alone or in combination with other components of the iris biometric recognition module 1514.

While the iris biometric recognition module 1514 appears large in structure, it is possible to scale down the size of the iris biometric recognition module 1514 to fit within smaller items or devices, for example, a mobile device (e.g., a mobile telephone, a tablet, or any other portable device). The iris biometric recognition module 1514 may be implemented, for example, as part of a forward and/or rearward facing camera in a mobile device. Optionally, the iris biometric recognition module 1514 may be implemented within a mobile device in any other suitable manner.

One or more cameras or other image sensors within the mobile device may capture image or video content to be utilized by the iris biometric recognition module 1514. The one or more cameras may include, or be based at least in part upon any appropriate technology, such as a CCD or CMOS image sensor having a sufficient resolution, focal range, and/or viewable area, to capture an image of the user when the user is operating the device.

Figure 15:
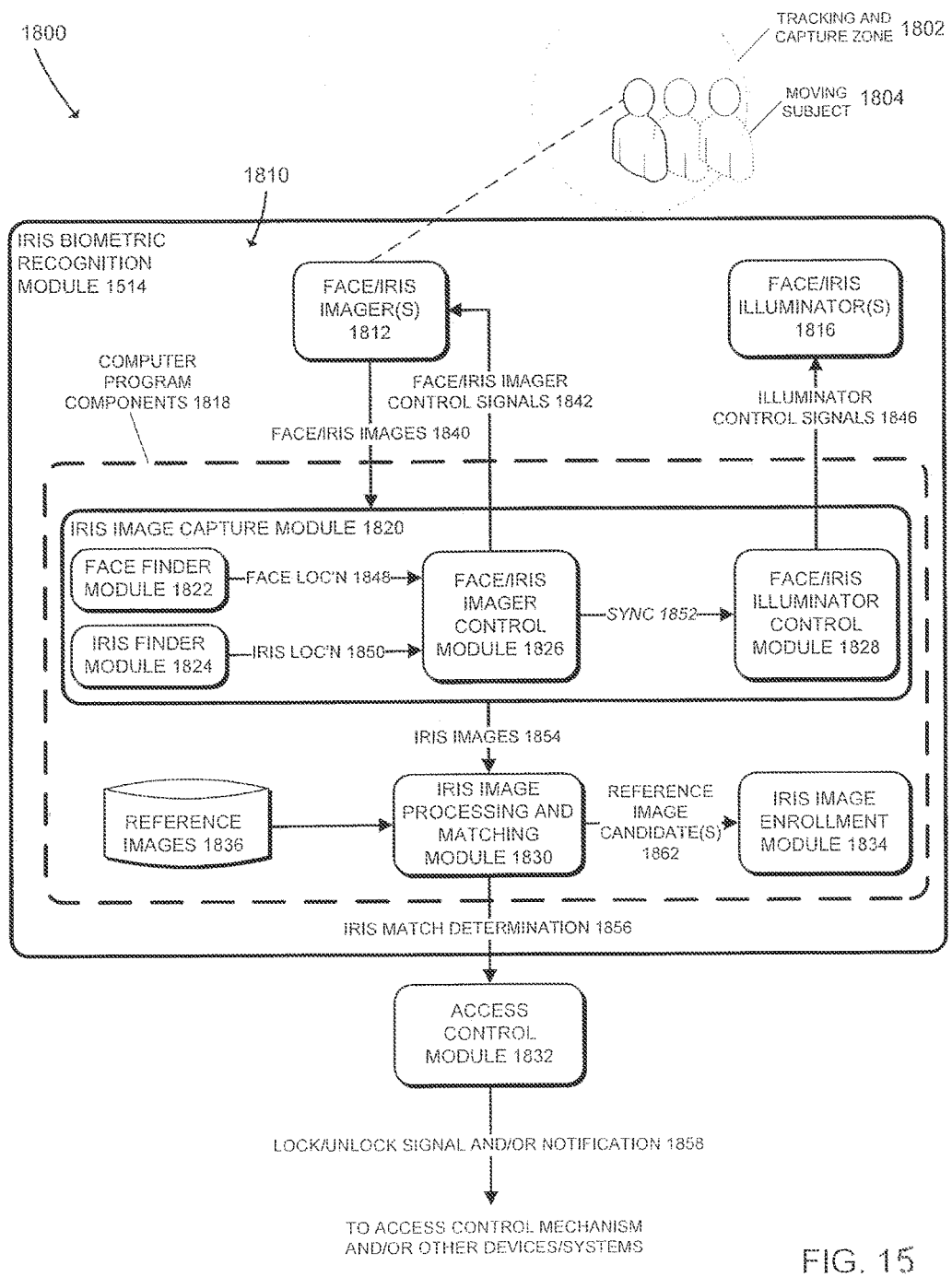
FIG. 15 is a simplified schematic diagram showing components of an iris biometric recognition module and an access control module in an environment of the access control assembly of FIG. 13.

Referring now to FIG. 15, an embodiment 1800 of an iris biometric-enabled access control system is shown. The iris biometric-enabled access control system 1800 is shown in the context of an environment 1810 that may be created during the operation of the iris biometric recognition module 1514 (e.g., a physical and/or virtual execution or "runtime" environment). As shown in the environment 1810, in addition to the hardware components described above, the iris biometric recognition module 1514 includes a number of computer program components 1818, each of which is embodied as machine-readable instructions, modules, data structures and/or other components, and may be implemented as computer hardware, firmware, software, mobile app, or a combination thereof, in memory of the controller board 1724, for example.

The iris biometric recognition module computer program components 1818 include an iris image capture module 1820. The illustrative iris image capture module 1820 includes a face finder module 1822, an iris finder module 1824, a face/iris imager control module 1826, and a face/iris illuminator control module 1828. In operation, the face/iris imager control module 1826 controls a face/iris imager 1812 (e.g., the face imager 1648 and/or the iris imager 1644) by transmitting face imager control signals 1842 to the face/iris imager 1812 to capture digital images of a human subject 1804 entering or located in a tracking and capture zone 1802. In some embodiments, the iris biometric recognition module 1514 may be equipped with a motion sensor that can detect the human subject 1804 in the tracking and capture zone 1802. In those embodiments, the face/iris imager control module 1826 may initiate operation of the face/iris imager(s) 1812 in response to a motion detection signal received from the motion sensor. In other embodiments, the presence of a human subject 1804 can be detected using an image processing routine that recognizes a face in the field of view of the face/iris imager 1812. As noted above, the iris biometric recognition module 1514 can utilize iris images captured from moving subjects and/or subjects that are at a distance that is greater than, e.g., 45 cm away from the iris imaging device.

The illustrative face finder module 1822 executes a face recognition algorithm (e.g., FaceRecognizer in OpenCV), to determine whether an image captured by the face/iris imager 1812 (e.g., by a wide field of view camera) includes a human face. If the face finder module 1822 detects a human face, the face finder module 1822 returns the face location 1848, e.g., bounding box coordinates of the detected face within the captured image. In response to the face detection, the face/iris imager control module 1826 configures the face/iris imager 1812 to capture an image of an iris of the detected face. To do this, the illustrative face/iris imager control module 1826 may compute the tilt angle by which to tilt the iris imager assembly 1626 based on the bounding box coordinates of the detected face. This can be done by approximating the linear distance from the face/iris imager 1812 to the detected face, if the location and the field of view of the face/iris imager 1812 are known. For example, the proper tilt angle for the face/iris imager 1812 can be derived from the geometry of the triangle formed by connecting the location of the face/iris imager 1812 to the top and bottom edges of the bounding box of the detected face.

Once the tilt angle for the face/iris imager 1812 is determined, the face/iris imager control module 1826 operates the motor 1720 to achieve the computed tilt angle of the face/iris imager 1812. Once the face/iris imager 1812 is properly positioned with respect to the detected face, the iris finder module 1824 locates an eye and then the iris of the eye, on the human face, by executing eye and iris detection algorithms (e.g., the algorithms mentioned above with reference to FIGS. 1-12). In response to receiving iris location information 1850 from the iris finder module 1824, the face/iris imager control module 1826 initiates the process of capturing images of the iris by transmitting iris imager control signals 1842 to the face/iris imager 1812. These iris detection and image capture processes can be performed, for example, using the techniques described above with reference to FIGS. 1-12.

In capturing images of the face and iris of the detected human subject, the iris image capture module 1820 interfaces with a face/iris illuminator control module 1828 to coordinate, e.g., synchronize 1852, the operation of the face/iris imager 1812 and face/iris illuminators 1818. During the face image capture process, the control modules 1826, 1828 synchronize the operation of the face illuminator assembly 1650 with the capturing of face images by the face imager 1648. This helps ensure consistent face image quality irrespective of the available ambient lighting conditions. In other words, the coordination of the face image capture and the operation of the face illuminator assembly 1650 is analogous to traditional flash photography, albeit using infrared light rather than visible light. Additionally, during the process of capturing the iris images, the control modules 1826, 1828 synchronize the operation of the iris illuminators 1816 (e.g., iris illuminator assemblies 1710, 1712) with the capturing of iris images by the iris imager 1644. To accommodate the possibility that the subject 1804 may be moving, the iris imager control module 1826 operates the iris imager 1644 using a focal sweep technique in which several (e.g., 10-15 or more) images of the iris are captured in rapid succession (e.g., at a shutter speed in the range of about 5 frames per second). Synchronously, the iris illuminator control module 1828 pulses/strobes the iris illuminators 1710, 1712 at the same rate/frequency. This helps ensure that at least one good quality iris image is obtained irrespective of the available ambient lighting conditions and regardless of whether the subject is moving or whether the view of the iris is obstructed or distorted. In other words, the coordination of the iris image capture and the operation of the iris illuminators 1710, 1712 is analogous to traditional "red eye reduction" flash photography, except that the images of the iris are taken at the same time as the pulsing/strobing of the iris illuminators 1710, 1712 rather than after the pulsing/strobing is completed (and also, using infrared illuminators rather than visible light).

The iris image capture module 1820 outputs or otherwise makes available the resulting iris images 1854 to an iris image processing and matching module 1830. The iris image processing and matching module 1830 processes the images by, e.g., removing portions of the image that depict eyelids and eyelashes and adjusting for enlarged pupils, and producing the "iris code" in, for example, the manner described above with reference to FIGS. 1-12. The iris image processing and matching module 1830 compares the processed iris images 1854 or usable portions thereof, or the iris code, to reference image data 1836, to determine whether any of the captured iris images 1854 match an image stored in the reference images 1836. The reference image data 1836 includes iris image samples and/or related data that has been obtained previously, e.g., through an enrollment procedure. If the iris images 1854 are not found to match any of the images in the reference images data 1836, the iris image processing and matching module 1830 may initiate an enrollment procedure. That is, the iris biometric recognition module 1514 can be configured to perform iris image enrollment directly at the device, if required or desired for a particular implementation. To do this, the iris image processing and matching module 1830 passes the collected iris image(s) 1862 to an iris image enrollment module 1834. To complete the enrollment process, the illustrative iris image enrollment module 1834 may execute an image quality analysis on one or more of the reference image candidates 1862. An iris image may be added to the reference images data 1836 if the image quality analysis indicates that the image is suitable for use as a reference image. In performing the image quality analysis, the iris image enrollment module 1834 may analyze a number of different image quality factors, such as: the amount of the iris that is exposed in the image (e.g., the person is not squinting or blinking), the sharpness of the image, and the number of artifacts in the image (e.g., the number of eyelashes, specularities, etc.).

As a result of the iris image processing and matching performed by the module 1830, the iris biometric recognition module 1514 outputs or otherwise makes available an iris match determination 1856. The iris match determination 1856 may be embodied as a simple "positive" or "negative" indication, or may include other information (such as person-identifying information connected with the matched iris image), alternatively or in addition. In the illustrative access control system 1800, an access control module 1832 executes business logic encoded as, e.g., computer program logic, to determine how or even whether the access control system 1800 should respond to the iris match determination data 1856. For example, the access control module 1832 may issue an electronic notification to another device or system, such as authentication on the mobile device, wireless communication, apps, financial transaction, etc. For instance, the access control module 1832 may enable or disable certain other electronic features of a device in response to the iris match determination 1856. As an example, the access control module 1832 may, in response to a positive iris match, transition the access control mechanism from a locked state to an unlocked state (or transition an access control assembly from a locked state in which the access control assembly prevents the person from accessing, for example, functionality of a mobile device, to an unlocked state in which the access control assembly allows the person to access the functionality), for example unlocking a wireless communication capability of, for example, a mobile device based on, e.g., personal profile information associated with the positive iris match. Similarly, the access control module 1832 may, in response to a negative iris match, transition the access control mechanism from a locked state to an unlocked state (or transition an access control assembly from a locked state in which the access control assembly prevents the person from accessing the functionality, to an unlocked state in which the access control assembly allows the person to access the functionality).

Figure 16:
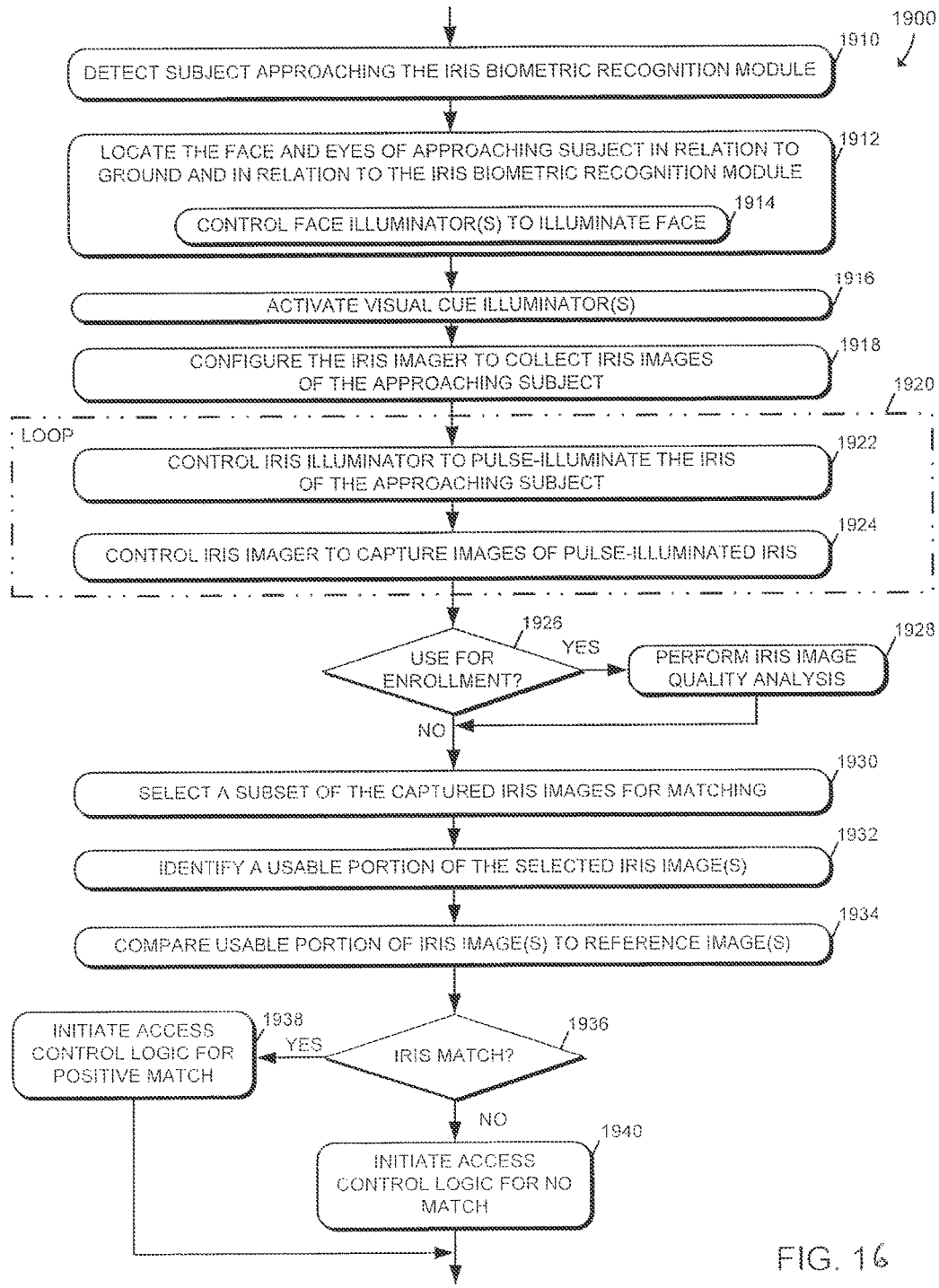
FIG. 16 is a simplified flow diagram of at least one embodiment of a method for performing iris biometric recognition-enabled access control as disclosed herein, which may be performed by one or more components of the iris biometric recognition module of FIG. 13.

Referring now to FIG. 16, an example of a method 1900 executable by one or more components of the iris biometric recognition module 1514. The method 1900 may be embodied as computerized programs, routines, logic and/or instructions, which may be embodied in hardware, software, mobile apps, firmware, or a combination thereof, of the iris biometric recognition module 1514 and/or one or more other systems or devices in communication with the iris biometric recognition module 1514. In block 1910, the module 1514 detects a human subject approaching the iris biometric recognition module 1514. To do this, the module 1514 may analyze signals received from a wide field of view camera (e.g., the face imager 1648) or may analyze signals received from a motion sensor monitoring a capture zone of the iris biometric recognition module 1514. In block 1912, the module 1514 locates the face and eyes of the approaching subject in relation to a ground plane and in relation to the iris biometric recognition module 1514. To do this, the module 1914 may, in block 1914, control the face illuminators 1649 to illuminate (with infrared light) the area in which the human subject, or more particularly, the subject's face, is detected.

Once the subject's face is located, in block 1916, the module 1514 configures the iris imager 1644 to collect images of an iris of an eye of the approaching subject. As noted above, configuring the iris imager may involve operating a motor to tilt a platform to which the iris imager is mounted. Alternatively, the configuring may be performed e.g. by software controlling the lens focus and/or field of view of the iris imager. In any event, the procedure of block 1916 aligns the iris imager with the eye (or more particularly the iris) of the approaching subject.

In some embodiments, in block 1918, the module 1514 activates the visual cue illuminators 1640, 1642, to try to draw the subject's attention or visual focus toward the iris biometric recognition module 1514. The visual cue illuminators 1640, 1642 are typically activated after the subject's face is detected and the iris imager is configured (e.g., mechanically positioned), in order to draw the subject's eyes in-line with the iris imager camera.

Once the subject's face and eyes are detected, the iris biometric recognition module 1514 enters a loop 1920 in which the module 1514 coordinates the operation of the iris illuminator and the iris imager in rapid succession to obtain multiple images of the iris (e.g., frame rate of the iris imager and short-duration pulse frequency of the iris illuminator are coordinated/synchronized). More specifically, in block 1922, the module 1514 causes the iris illuminator assemblies to issue short pulses of high intensity infrared light. As discussed above with reference to FIGS. 1-12, in some embodiments of the module 1514, a light intensity of the illumination source (e.g., illuminators 1711) is increased during strobe to maintain a predetermined signal-to-noise (S/N) ratio, while an average irradiance of the illumination source over the course of the strobing remains below a safety threshold. At substantially the same time, the module 1514 causes the iris imager to capture a series of images of the pulse-illuminated iris (using, e.g., a "focal sweep" technique). That is, the iris image captures are timed to substantially coincide with the short, high intensity pulses of illumination, resulting in a "freeze" effect on the subject if the subject is in motion. In other embodiments, other alternatives to the focal sweep technique can be used, e.g.: auto focus on a target spot, if the subject is standing still for a length of time, or by using a fixed lens to provide a large fixed focus area.

In block 1926, the module 1514 determines whether to use any of the captured iris images are candidates to be used for enrollment purposes. If an iris image is a candidate to be used for enrollment, the module 1514 performs an iris image quality analysis on the image in block 1928, and updates the reference database of iris images if the quality analysis is successful.

In blocks 1930, 1932, and 1934, the module 1514 performs iris image processing and matching in accordance with, for example, the techniques described above with reference to FIGS. 1-12. In block 1930, the module 1514 selects a subset of the captured iris images for matching purposes, based on image quality, size of the iris depicted in the image, and/or other factors. In block 1932, the module 1514 identifies a usable portion of the iris image(s) selected in block 1930 (using, e.g., the segmentation techniques described above). The "usable portion" of an iris image may correspond to the iris code, in some embodiments. In block 1934, the module 1514 compares the usable portion of the iris image identified in block 1932 to one or more reference images (e.g., the reference images 1836). In block 1936, the module 1514 determines whether the comparison performed in block 1934 results in an iris match.

While the flow diagram of FIG. 16 references an approaching subject, the steps discussed in relation to the flow diagram of FIG. 16 may be performed for a moving or a stationary subject. For example, the flow diagram in FIG. 16 may be utilized to authenticate a subject that is waiting for a bus or otherwise stationary for any reason or to authenticate a user that desires to access a mobile device, access wireless communication, make a financial transaction, etc. In any situation where the subject/user is stationary, the subject/user may remain stationary in order to draw the subject's eyes in line with the iris imager camera on the mobile device and the iris image may then be captured and matched as discussed in detail above.

An "iris match" as determined by the module 1514 may refer to, among other things, a numerical score that represents the probability that the captured iris image corresponds to the known iris image of a specific person. The "iris match" parameters are tunable, and can be set, for example, based on the accuracy requirements of a particular implementation of the module 1514 (e.g., how stringent is the test for acceptance of the subject as matching the identity of a known subject). As mentioned above with reference to FIGS. 1-12, the illustrative module 1514 computes a Hamming distance between an iris code representative of the captured iris image and the iris code representative of a reference iris image. In information theory, the Hamming distance between two strings of equal length is the number of positions at which the corresponding symbols are different. Put another way, the Hamming distance measures the minimum number of substitutions required to change one string into the other, or the number of errors that transformed one string into the other. So, for example, if the module 1514 uses a Hamming distance of 0.35, that corresponds to a 1:133,000 false accept rate. Similarly, if the module 1514 is configured to use a Hamming distance of 0.28, the false accept rate is 1:10E11.

If the module 1514 determines in block 1936 that there is an iris match, the module 1514 outputs a match signal that can be used by an access control assembly to initiate access control logic for a positive match in block 1938 (e.g., transitioning from a locked to an unlocked state (or transitioning an access control assembly from a locked state in which the access control assembly prevents the person from accessing functionality, to an unlocked state in which the access control assembly allows the person to access the functionality)). If the module 1514 determines in block 1936 that there is not an iris match, the module 1514 outputs a "no match" signal (or the absence of a signal may also be used as a no-match indication), which can be used by an access control assembly to initiate access control logic for a negative match condition (e.g., disable access to the functionality).

Example Usage Scenarios

Numerous applications of the disclosed technology exist that would benefit if the user and/or subject who is at a location, accessing an object, entering a premises, etc. could be accurately authenticated, verified, identified, or biometrically recorded at that instance of time for a variety of reasons. Many of these instances do not require one to know who the person is at that time. To date, this has not been possible due to the cumbersome nature of creating a biometric record and/or accurately matching to an existing template for the user or subject.

Today, documenting/recording the presence of an individual at a location at a moment in time is typically managed by the individual being identified by another person by sight, via a set of questions, and/or the person inspecting credentials such as a passport, driver license, employee badge, etc. (which must be validated) presented by the individual or recording a video or photograph of the individual at that location. None of these approaches is entirely accurate. The process of inspecting the credentials only validates the credentials presented. It does not validate that the person holding those credentials is actually the person described on the credentials. In addition, videos and photos can be easily manipulated to inaccurately record or misrepresent the presence of a person at a specific location.

The ability to record the presence of a user or subject by using an iris biometric collection device (which may be incorporated into another type of device, such as a fixed or mobile electronic device) that uses strobe illumination above the continuous wave eye safe limit would allow the documentation that the actual person was at that location, accessed an item, used a service, or obtained a benefit at the specific time. The use of the strobe illumination above the continuous wave eye safe limits allows collection of the biometric image in all lighting conditions (indoor, outdoor, bright sunlight, extreme darkness) and without requiring the subject or user to be stationary. Unlike existing biometric iris readers, the disclosed devices can be equipped with wired and/or wireless connectivity to maintain the most recent data on the device. Use of the iris as the enabling biometric allows identity to be determined without touching the subject as in a fingerprint and is less obtrusive than other biometric identification modalities. The implementations disclosed herein allow the collection of a high quality record with cooperative or uncooperative subjects including covert operations. Recording of the person's iris at a location at a specific time can be used verifiable proof that the specific person was at a particular location. The relevant location information can be captured as well (e.g., by a Global Positioning System or cellular location-based system), and stored along with the iris image and/or associated information. The biometric collection device described may be used alone or in conjunction with other collection and authentication techniques (e.g., PIN, pattern, different biometric) if multi-levels of authentication are desired.

Examples of events, activities or locations where the ability to document/record the presence or access of a person(s) to the location at a specific times are as follows: safes and safety deposit boxes; amusement parks; animal tagging and tracking (domestic, wild, aquatic, etc.); appliances (refrigerator, oven, gym equipment); assisted living facilities; automated teller machine; automated gate control; background checks; blood donors/red cross; brokerage account; casino; check cashing agencies; child day care facilities; commercial shipping facility; cruise ships; data-center cabinets; detox centers; document screening activity; driver vehicle enrollment; drug testing collection location; entertainment facilities (club, theater, concert hall, skyboxes, stadiums, etc.); entitlement programs activities; ez pass authorization; fire drills; first responders securing an event; gun access; half-way houses; health club/gym/spa; hospitals; hotels/motels; insurance claim validations; large clinical studies; law enforcement activities; library; medical lab (quest/labcorp); mining operations; parole tracking; patient history; pay per usage; prisons; property storage locations; real-time monitoring of person using computer; refuge tracking; rehabilitation clinics; resorts; retail services; schools; shopper loyalty; ski lifts; sporting events; tax preparing and paying services; tele-medical services; tradeshow/conferences; validation of service personnel; vehicle management; voting and petitions; workforce management, and/or others.

Figure 18:
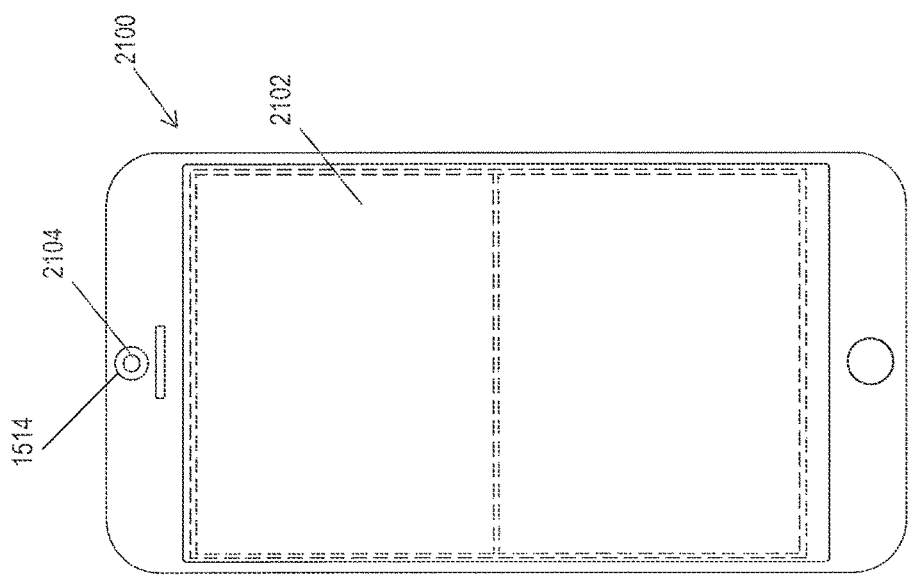
FIG. 18 is a simplified view of at least one embodiment of an iris biometric recognition enabled access control assembly in an exemplary operating environment (i.e., a mobile device)

FIG. 18 illustrates the iris biometric module 1514 of FIGS. 13 and 14 (or any other embodiment of the iris biometric module) implemented within a mobile device 2100 (e.g. a mobile telephone, a tablet, an electronic watch or bracelet, or any other mobile device). The mobile device 2100 may be any mobile or semi-mobile electronic device, for example, a personal computer, laptop computer, tablet computer, e-reader, smartphone, personal data assistant, set-top box, digital media player, microconsole, home automation system, or other computing device having a processor, central processing unit, microprocessor, or other suitable processor. The mobile device 2100 may include a display 2102, which may be a monitor, liquid crystal display screen, light-emitting diode (LED or organic LED (OLED)) screen, or other output-only video display. The display 2102 may function as an input device, such as a capacitive, resistive, or inductive touchscreen.

The iris biometric module 1514 may be configured as an add-on to the mobile device 2100 or may be incorporated into the mobile device 2100, for example, as part of a camera 2104 within the mobile device 2100. In some embodiments in which the iris biometric module 1514 is incorporated within the mobile device 2100, the iris imager assembly 1626 may replace or work in conjunction with the mobile device camera 2104.

The iris processor 100 described above with respect to FIGS. 1-11 may be implemented within the mobile device 2100 system in any suitable manner, for example, as discussed with respect to FIG. 12. In one embodiment, the iris processor 100 may be a separate processor within the mobile device memory or the mobile device 2100 may include a single processor that implements all mobile device functionality, including the functionality of the iris processor 100. The iris processor 100 may be used to identify and authorize a user (or users) of the mobile device 2100. By using identity information derived from iris biometrics, the iris processor 100 may determine whether the user is an authorized user of the mobile device 2100 and/or may determine what applications, settings, and/or other features of the mobile device 2100 may be accessed by the user. In at least one embodiment, a first user may have permission to use all or a first subset of applications, settings, and/or features (e.g., a parent that can access all applications, settings, and/or other features on the mobile device 2100) and a second user may have permission to use all or a second subset of applications, settings, and/or features (e.g., a child that may only be able to access child-friendly applications on the mobile device 2100). In some embodiments, the mobile device 2100 may be configured to require identification and authorization to access the device (i.e., as a login procedure) and/or may be configured to require identification and authorization to access one or more applications, settings, and/or features on the mobile device 2100.

Implementation Examples

Figure 17:
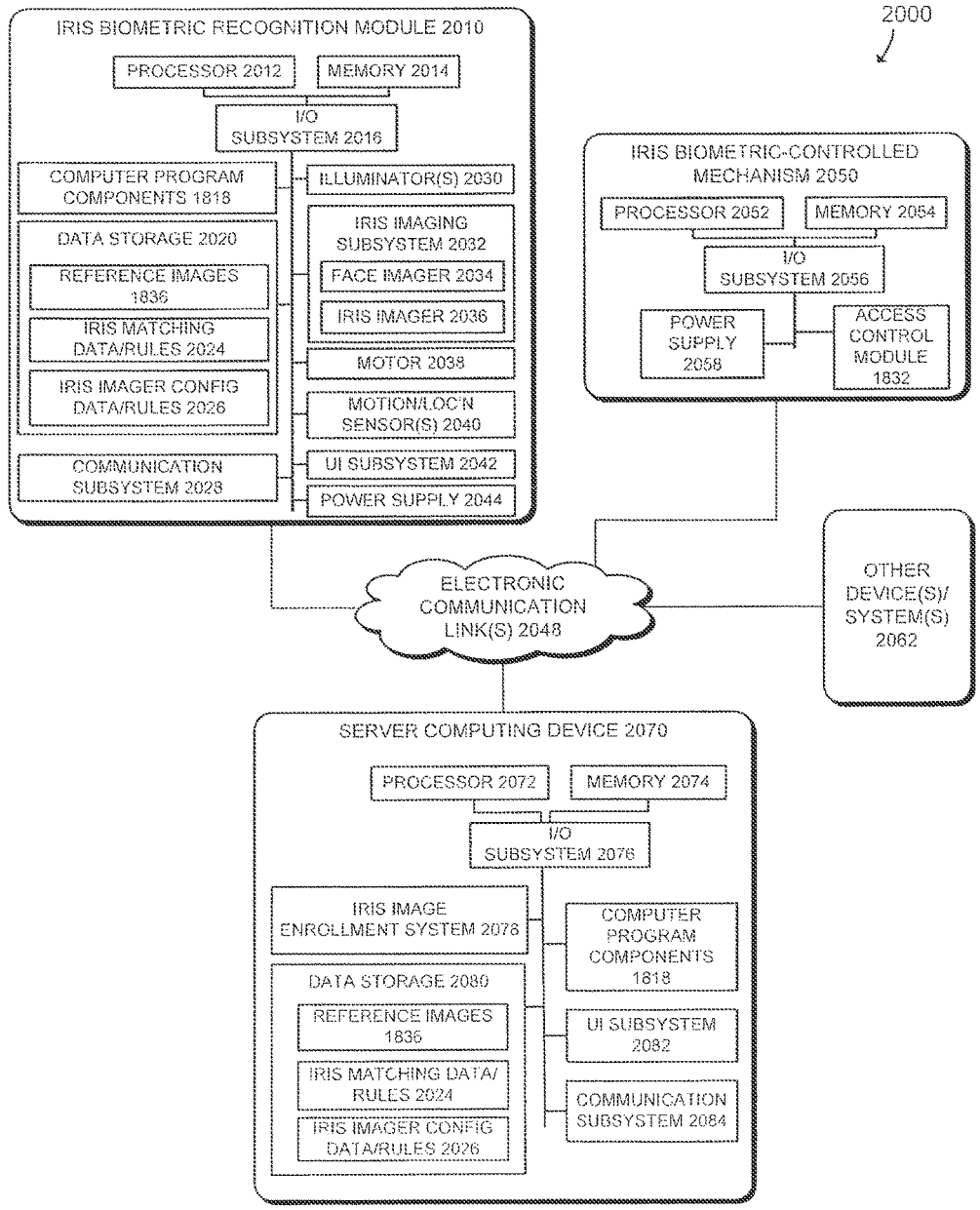
FIG. 17 is a simplified block diagram of at least one embodiment of a system including an iris biometric recognition module as disclosed herein.

Referring now to FIG. 17, a simplified block diagram of an iris biometric recognition-enabled system 2000 is shown. While the illustrative embodiment 2000 is shown as involving multiple components and devices, it should be understood that the system 2000 may constitute a single device, alone or in combination with other devices. The system 2000 includes an iris biometric recognition module 2010, an iris biometric-controlled mechanism 2050, one or more other devices and/or systems 2062, and a server computing device 2070. Each or any of the devices/systems 2010, 2050, 2062, 2070 may be in communication with one another via one or more electronic communication links 2048.

The system 2000 or portions thereof may be distributed across multiple computing devices as shown. In other embodiments, however, all components of the system 2000 may be located entirely on, for example, the iris biometric recognition module 2010 or one of the devices 2050, 2062, 2070. In some embodiments, portions of the system 2000 may be incorporated into other systems or computer applications. Such applications or systems may include, for example, commercial off the shelf (COTS) or custom-developed cameras, operating systems, authentication systems, or access control systems. As used herein, "application" or "computer application" may refer to, among other things, any type of computer program or group of computer programs, whether implemented in software, hardware, or a combination thereof, and includes self-contained, vertical, and/or shrink-wrapped software applications, distributed and cloud-based applications, and/or others. Portions of a computer application may be embodied as firmware, as one or more components of an operating system, a runtime library, an application programming interface (API), as a self-contained software application, or as a component of another software application, for example.

The illustrative iris biometric recognition module 2010 includes at least one processor 2012 (e.g. a microprocessor, microcontroller, digital signal processor, etc.), memory 2014, and an input/output (I/O) subsystem 2016. The module 2010 may be embodied as any type of electronic or electromechanical device capable of performing the functions described herein. Although not specifically shown, it should be understood that the I/O subsystem 2016 can include, among other things, an I/O controller, a memory controller, and one or more I/O ports. The processor 2012 and the I/O subsystem 2016 are communicatively coupled to the memory 2014. The memory 2014 may be embodied as any type of suitable computer memory device, including fixed and/or removable memory devices (e.g., volatile memory such as a form of random access memory or a combination of random access memory and read-only memory, such as memory cards, e.g., SD cards, memory sticks, hard drives, and/or others).

The I/O subsystem 2016 is communicatively coupled to a number of hardware and/or software components, including computer program components 1818 such as those shown in FIG. 15 or portions thereof, illuminator(s) 2030 (e.g., face and iris illuminators 1816), an imaging subsystem 2032 (which may include separate face and iris imagers 2034, 2036), a motor 2038, and one or more motion and/or location sensors 2040. As used herein, an "imager" or "camera" may refer to any device that is capable of acquiring and recording two-dimensional (2D) or three-dimensional (3D) still or video images of portions of the real-world environment, and may include cameras with one or more fixed camera parameters and/or cameras having one or more variable parameters, fixed-location cameras (such as "stand-off" cameras that are installed in walls or ceilings), and/or mobile cameras (such as cameras that are integrated with consumer electronic devices, such as laptop computers, smart phones, tablet computers, wearable electronic devices and/or others).

The I/O subsystem 2016 is also communicatively coupled to one or more data storage devices 2020, a communication subsystem 2028, a user interface subsystem 2042, and a power supply 2044 (e.g., a battery). The user interface subsystem 2042 may include, for example, hardware or software buttons or actuators, a keypad, a display device, visual cue illuminators, and/or others. It should be understood that each of the foregoing components and/or systems may be integrated with the module 2010 or may be a separate component or system that is in communication with the I/O subsystem 2016 (e.g., over a network or a bus connection). In some embodiments, the UI subsystem 2042 includes a push button or similar mechanism for initiating the iris image enrollment process described above. In other embodiments, the iris image enrollment process takes place off the module 2010, e.g., on another device, such as a desktop computing device. Alternatively or in addition, iris image enrollment capabilities can be provided at a "central" module or server computer and then propagated to other modules 2010, e.g., via a communications network. For instance, in access control applications, enrollment may take place at a main entrance to a facility or security command center. Privileges can be determined at the central module or server and then pushed out to or "downloaded" by the individual door lock assemblies in the facility.

The data storage device 2020 may include one or more hard drives or other suitable data storage devices (e.g., flash memory, memory cards, memory sticks, and/or others). In some embodiments, portions of the system 2000 containing data or stored information, e.g., a database of reference images 1836, iris matching data/rules 2024 (e.g., access control logic or business logic for determining when an iris match has occurred and what to do when an iris match does or does not occur), iris imager configuration data/rules 2026 (e.g., mapping tables or functions for mapping iris imager tilt angles to motor control parameters), and/or other data, reside at least temporarily in the storage media 2020. Portions of the system 2000, e.g., the iris image database 2022, the iris matching data/rules 2024, the iris imager configuration data/rules 2026, and/or other data, may be copied to the memory 2014 during operation of the module 2010, for faster processing or other reasons.

The communication subsystem 2028 communicatively couples the module 2010 to one or more other devices, systems, or communication networks, e.g., a local area network, wide area network, personal cloud, enterprise cloud, public cloud, and/or the Internet, for example. Accordingly, the communication subsystem 2028 may include a databus, datalink, one or more wired or wireless network interface software, firmware, or hardware, for example, as may be needed pursuant to the specifications and/or design of the particular embodiment of the module 2010.

The iris biometric-controlled mechanism 2050, the other device(s)/system(s) 2062, and the server computing device 2070 each may be embodied as any suitable type of computing device, electronic device, or electromechanical device capable of performing the functions described herein, such as any of the aforementioned types of devices or other electronic devices. For example, in some embodiments, the server computing device 2070 may operate a "back end" portion of the iris biometric computer program components 1818, by storing the reference images 1836, iris matching data/rules 2024, and/or iris imager configuration data/rules 2026, in a data storage device 2080 or by performing other functions of the module 2010. In general, components of the server computing device 2070 having similar names to components of the module 2010 described above (e.g., processor 2072, memory 2074, I/O subsystem 2076) may be embodied analogously. The illustrative server computing device 2070 also includes a user interface subsystem 2082, a communication subsystem 2084, and an iris image enrollment system 2078 (which may capture and evaluate iris images for enrollment purposes, similar to the iris image enrollment module 1834 described above).

Further, each of the mechanisms/devices/systems 2050, 2062 may include components similar to those described above in connection with the module 2010 and/or the server computing device 2070, or another type of electronic device (such as a portable electronic device, embedded system (e.g., a vehicle infotainment system or smart appliance system). For example, the iris biometric-controlled mechanism 2050 includes one or more processors 2052, memory 2054, and an I/O subsystem 2056 (analogous to the processor 2012, memory 2014, and I/O subsystem 2016), an on-board power supply 2058 (e.g., a battery), and an access control module 1832 (e.g., to perform access control logic in response to an iris match determination made by the module 2010). The system 2000 may include other components, sub-components, and devices not illustrated in FIG. 17 for clarity of the description. In general, the components of the system 2000 are communicatively coupled as shown in FIG. 20 by one or more electronic communication links 2048, e.g., signal paths, which may be embodied as any type of wired or wireless signal paths capable of facilitating communication between the respective devices and components, including direct connections, public and/or private network connections (e.g., Ethernet, Internet, etc.), or a combination thereof, and including short range (e.g., Near Field Communication) and longer range (e.g., Wi-Fi or cellular) wireless communication links.

The wireless communication device contained in a computer or mobile device is authorized for use by the operator of the device by activating an application that directs the wireless communication device to complete a defined event, task, or transaction. Knowing who is controlling the wireless capability on a mobile device allows new applications to be developed that will leverage that knowledge. Today the wireless capability is controlled by the person holding the mobile device, regardless of whether they are the authorized user. Today, people use PINS, swipes, and other biometrics. The process in place does not validate the person holding that device is actually the person authorized to use the device or the person authorized to initiate the application to allow an event to occur or benefit from the results of the event (i.e., unlock a door, process a financial transaction, etc.). Adding an accurate biometric identification capability and tying it directly to the wireless capability solves the problem. Using an iris biometric is the most accurate biometric and the disclosed approach allows it to be used in all environmental conditions.

Figure 19:
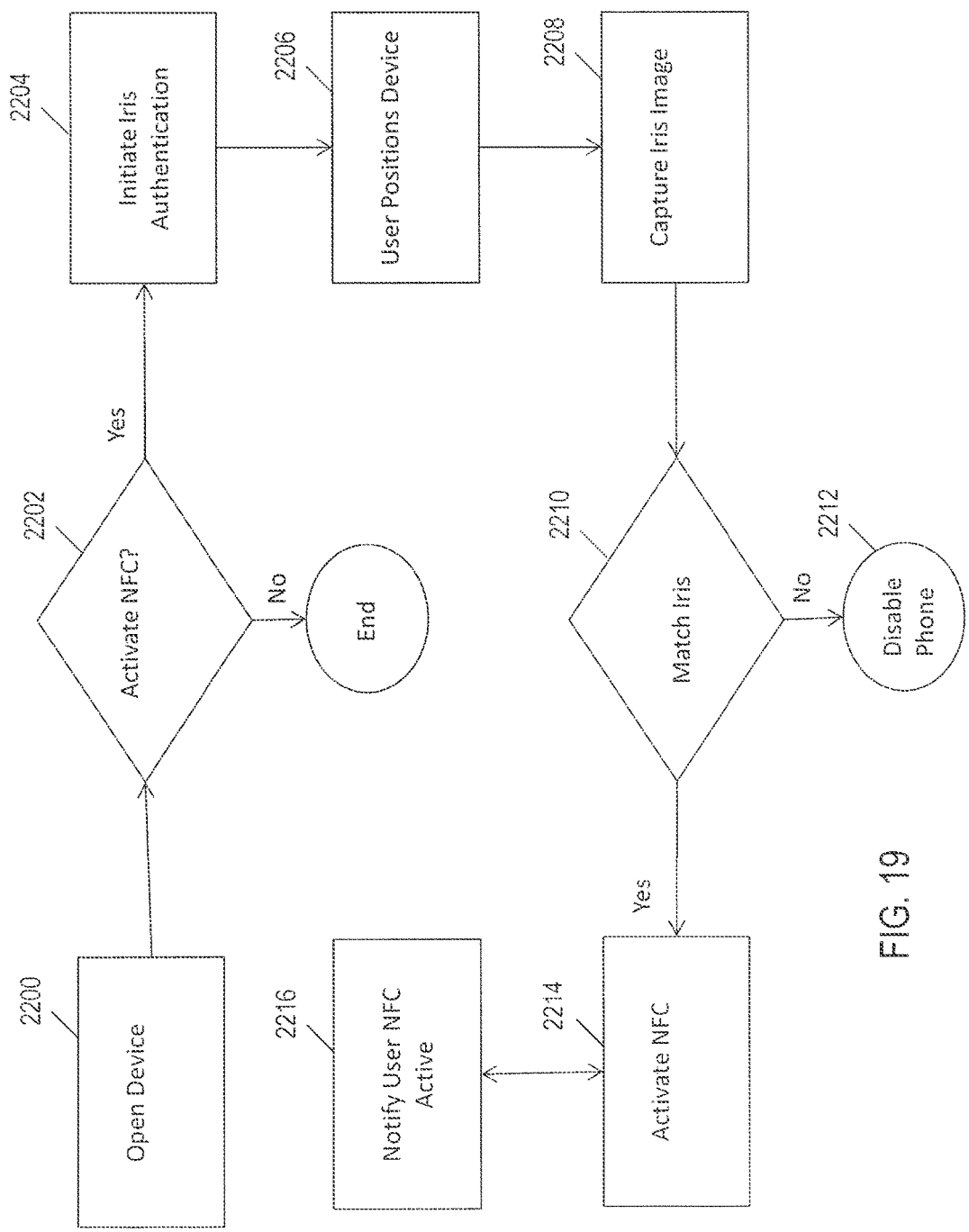
FIG. 19 is a flowchart depicting an exemplary method for activating wireless capability of a device.

In the disclosed invention and as seen in FIG. 19, a user may open a mobile or other electronic device running apps with wireless communication capability (Block 2200). The user may then try to activate the wireless communication capability (Block 2202). In response, the electronic device may initiate iris authentication for the user (Block 2204), and the user may position the device (Block 2206) for image capture (Block 2208). If the iris does not match the template in the database (at Block 2210), the app and/or the device may be disabled (Block 2212). However, if a match is found, the wireless communication capability may be activated (Block 2214). In some embodiments, the user may be notified that the wireless communication capability has been activated (Block 2216).

Additional Examples

Illustrative examples of the technologies disclosed herein are provided below. An embodiment of the technologies may include any one or more, and any combination of, the examples described below.

In an example 1, a biometric access control device includes a camera having a field of view, an illuminator device comprising one or more illuminators that emit light into the field of view, a client device enabled to authenticate a person to access a wireless communication capability to transmit a wireless communication to a second device, an input device, memory storing program instructions, and a processor communicatively coupled to the illuminator device, the camera, the client device, the input device, and the memory, and further communicatively coupled to a database storing a reference iris image for a user validated to access the client device, the processor executing the program instructions to: receive an input signal from the input device, determine that the input signal comprises a permission to scan an iris of a person in proximity to the client device, align the camera with the iris of the person, send a first control signal to the illuminator device, the first control signal activating a synchronous emission of light by the one or more illuminators at a pulse frequency above continuous wave eye safe limits, send a second control signal to the camera, the second control signal activating a capture of a plurality of digital images by the camera, the capture being synchronous with the synchronous emission of light, receive the plurality of digital images from the camera, access the database and retrieve the reference iris image, determine that a first digital image of the plurality of digital images matches the reference iris image, authenticate the person as authorized to access the wireless communication capability, and transmit the wireless communication from the client device to the second device.

An example 2 includes the subject matter of example 1, wherein the client device comprises mobile software application, the wireless communication capability comprises a financial transaction performed by the mobile software application, and the second device comprises an automated teller machine configured to complete the financial transaction responsive to receiving the wireless communication.

An example 3 includes the subject matter of any of examples 1 or 2, wherein the processor executing the program instructions to: determine that the first digital image of the plurality of digital images does not match the reference iris image and deny the person access to the wireless communication capability on the client device.

An example 4 includes the subject matter of any of examples 1, 2, or 3, wherein the camera, the illuminator device, the input device, the memory and the processor are incorporated into the client device.

An example 5 includes the subject matter of any of examples 1, 2, 3, or 4, wherein the illuminator device comprises at least one infrared illuminator and the program instructions operate the illuminator device to illuminate the iris with a pulsing or strobe illumination operation above continuous wave eye safe limits.

An example 6 includes the subject matter of any of examples 1, 2, 3, 4, or 5, wherein the camera, the illuminator device, the client device, the input device, the memory and the processor are communicatively coupled, via wired or wireless internet connectivity, to a local, remote or cloud database.

In an example 7, an iris biometric system controlling access to a wireless communication capability for a device includes an iris biometric recognition module that authenticates a person to access a first device to transmit a wireless communication to a second device, the iris biometric recognition module including an iris imager device comprising a lens, an illuminator device, memory storing program instructions, and one or more processors communicatively coupled to the iris imager device, the illuminator device, and the memory, the one or more processors executing the program instructions to: align the lens of the iris imager device with an iris of the person, operate the illuminator device to illuminate the iris, operate the iris imager device to produce a digital image of the iris, compare the digital image to a reference iris image, and responsive to a determination that the digital image matches the reference iris image, authenticate the person as authorized to access the first device and transmit the wireless communication from the first device to the second device.

An example 8 includes the subject matter of example 7, wherein the iris imager device, the illuminator device and the iris biometric recognition module are incorporated into the first device.

An example 9 includes the subject matter of any of examples 7 or 8, wherein the illuminator device comprises at least one infrared illuminator and the one or more processors executing the program instructions operates the illuminator device to illuminate the iris with a pulsing or strobe illumination operation above continuous wave eye safe limits.

An example 10 includes the subject matter of any of examples 7, 8, or 9, wherein the iris imager device, the illuminator device and the iris biometric recognition module are incorporated into a mobile device.

An example 11 includes the subject matter of any of examples 7, 8, 9, or 10, wherein the iris biometric recognition module is communicatively coupled, via wired or wireless internet connectivity, to a local, remote or cloud database.

An example 12 includes the subject matter of any of examples 7, 8, 9, 10, or 11, wherein the one or more processors execute the program instructions to deny the person access to the first device to terminate authorization to transmit the wireless communication after a predetermined time period.

An example 13 includes the subject matter of any of examples 7, 8, 9, 10, 11, or 12, wherein the second device is a secure device through which a transaction may be conducted.

In an example 14, a method comprising authenticating a person to access a first device to transmit a wireless communication to a second device via an iris biometric recognition module comprises program instructions stored in memory and causing one or more processors to execute the steps of: aligning a lens of an iris imager device with the iris of the person, operating an illuminator device to illuminate the iris, operating the iris imager device to produce a digital image of the iris, comparing the digital image to a reference iris image, and responsive to a determination that the digital image matches the reference iris image, authenticating the person as authorized to access the first wireless communication-enabled device and transmitting the wireless communication from the first device to the second device.

An example 15 includes the subject matter of claim 14, wherein authenticating the person to access a first device to transmit a wireless communication to a second device via the iris biometric recognition module is executed via the first device incorporating the iris imager device, the illuminator device and the one or more processors.

An example 16 includes the subject matter of any of claim 14 or 15, wherein operating the illuminator device comprises operating an infrared illuminator and operating the infrared illuminator comprises illuminating the iris with a pulsing or strobe illumination operation above continuous wave eye safe limits.

An example 17 includes the subject matter of any of claim 14, 15, or 16, wherein authenticating the person to access a first device to transmit a wireless communication to a second device via the iris biometric recognition module is executed via a mobile device incorporating the iris imager device, the illuminator device and the one or more processors.

An example 18 includes the subject matter of any of claim 14, 15, 16, or 17, and further comprises accessing the reference iris image via wired or wireless internet connectivity, from a local, remote or cloud database.

An example 19 includes the subject matter of any of claim 14, 15, 16, 17, or 18, and further comprises terminating authorization to transmit the wireless communication after a predetermined time period.

An example 20 includes the subject matter of any of claim 14, 15, 16, 17, 18, or 19, wherein the second device is a secure device through which a transaction may be conducted.

GENERAL CONSIDERATIONS

In the foregoing description, numerous specific details, examples, and scenarios are set forth in order to provide a more thorough understanding of the present disclosure. It will be appreciated, however, that embodiments of the disclosure may be practiced without such specific details. Further, such examples and scenarios are provided for illustration, and are not intended to limit the disclosure in any way. Those of ordinary skill in the art, with the included descriptions, should be able to implement appropriate functionality without undue experimentation.

References in the specification to "an embodiment," etc., indicate that the embodiment described may include a particular feature, structure, or characteristic, but every embodiment may not necessarily include the particular feature, structure, or characteristic. Such phrases are not necessarily referring to the same embodiment. Further, when a particular feature, structure, or characteristic is described in connection with an embodiment, it is believed to be within the knowledge of one skilled in the art to affect such feature, structure, or characteristic in connection with other embodiments whether or not explicitly indicated.

Embodiments in accordance with the disclosure may be implemented in hardware, firmware, software, or any combination thereof. Embodiments may also be implemented as instructions stored using one or more machine-readable media, which may be read and executed by one or more processors. A machine-readable medium may include any mechanism for storing or transmitting information in a form readable by a machine (e.g., a computing device or a "virtual machine" running on one or more computing devices). For example, a machine-readable medium may include any suitable form of volatile or non-volatile memory.

Modules, data structures, blocks, and the like are referred to as such for ease of discussion, and are not intended to imply that any specific implementation details are required. For example, any of the described modules and/or data structures may be combined or divided into sub-modules, sub-processes or other units of computer code or data as may be required by a particular design or implementation. In the drawings, specific arrangements or orderings of schematic elements may be shown for ease of description. However, the specific ordering or arrangement of such elements is not meant to imply that a particular order or sequence of processing, or separation of processes, is required in all embodiments. In general, schematic elements used to represent instruction blocks or modules may be implemented using any suitable form of machine-readable instruction, and each such instruction may be implemented using any suitable programming language, library, application-programming interface (API), and/or other software development tools or frameworks. Similarly, schematic elements used to represent data or information may be implemented using any suitable electronic arrangement or data structure. Further, some connections, relationships or associations between elements may be simplified or not shown in the drawings so as not to obscure the disclosure. This disclosure is to be considered as exemplary and not restrictive in character, and all changes and modifications that come within the spirit of the disclosure are desired to be protected.

The claimed invention is:

1. A biometric access control device comprising:
    a camera having a field of view;
    an illuminator device comprising one or more illuminators that emit light into the field of view;
    a client device enabled to authenticate a person to access a wireless communication capability to transmit a wireless communication to a second device;
    an input device;
    memory storing program instructions; and
    a processor communicatively coupled to the illuminator device, the camera, the client device, the input device, and the memory, and further communicatively coupled to a database storing a reference iris image for a user validated to access the client device, the processor executing the program instructions to:
      receive an input signal from the input device;
      determine that the input signal comprises a permission to scan an iris of a person in proximity to the client device;
      align the camera with the iris of the person;
      send a first control signal to the illuminator device, the first control signal activating a synchronous emission of light by the one or more illuminators;
      send a second control signal to the camera, the second control signal activating a capture of a plurality of digital images by the camera, the capture being synchronous with the synchronous emission of light;
      receive the plurality of digital images from the camera;
      access the database and retrieve the reference iris image;
      determine that a first digital image of the plurality of digital images matches the reference iris image, wherein the first digital image is a low resolution image selected from a plurality of resolutions, and wherein determining the match comprises selecting a low frequency component corresponding to said low resolution image, said low resolution image and said low frequency component being the lowest sufficient to identify coarse iris features;
      authenticate the person as authorized to access the wireless communication capability; and
      transmit the wireless communication from the client device to the second device.

2. The biometric access control device of claim 1, wherein:
    the client device comprises mobile software application;
    the wireless communication capability comprises a financial transaction performed by the mobile software application; and
    the second device comprises an automated teller machine configured to complete the financial transaction responsive to receiving the wireless communication.

3. The biometric access control device of claim 1, wherein the processor executing the program instructions to:
    determine that the first digital image of the plurality of digital images does not match the reference iris image; and
    deny the person access to the wireless communication capability on the client device.

4. The biometric access control device of claim 1, wherein the camera, the illuminator device, the input device, the memory and the processor are incorporated into the client device.

5. The biometric access control device of claim 1, wherein:
    the illuminator device comprises at least one infrared illuminator; and
    the program instructions operate the illuminator device to illuminate the iris with a pulsing or strobe illumination operation above continuous wave eye safe limits.

6. The biometric access control device of claim 1, wherein the camera, the illuminator device, the client device, the input device, the memory and the processor are communicatively coupled, via wired or wireless internet connectivity, to a local, remote or cloud database.

7. An iris biometric system controlling access to a wireless communication capability for a device comprising:
    an iris biometric recognition module that authenticates a person to access a first device to transmit a wireless communication to a second device, the iris biometric recognition module comprising:
      an iris imager device comprising a lens;
      an illuminator device;
      memory storing program instructions; and
      one or more processors communicatively coupled to the iris imager device, the illuminator device, and the memory, the one or more processors executing the program instructions to:
        align the lens of the iris imager device with an iris of the person;
        operate the illuminator device to illuminate the iris;
        operate the iris imager device to produce a digital image of the iris;
        compare the digital image to a reference iris image; and responsive to a determination that the digital image matches the reference iris image:
  authenticate the person as authorized to access the first device, wherein the digital image is a low resolution image selected from a plurality of resolutions, and wherein determining the match comprises selecting a low frequency component corresponding to said low resolution image, said low resolution image and said low frequency component being the lowest sufficient to identify coarse iris features; and
  transmit the wireless communication from the first device to the second device.

8. The iris biometric system of claim 7, wherein the iris imager device, the illuminator device and the iris biometric recognition module are incorporated into the first device.

9. The iris biometric system of claim 7, wherein:
the illuminator device comprises at least one infrared illuminator; and
the one or more processors executing the program instructions operates the illuminator device to illuminate the iris with a pulsing or strobe illumination operation above continuous wave eye safe limits.

10. The iris biometric system of claim 7, wherein the iris imager device, the illuminator device and the iris biometric recognition module are incorporated into a mobile device.

11. The iris biometric system of claim 7, wherein the iris biometric recognition module is communicatively coupled, via wired or wireless internet connectivity, to a local, remote or cloud database.

12. The iris biometric system of claim 7, wherein the one or more processors execute the program instructions to deny the person access to the first device to terminate authorization to transmit the wireless communication after a predetermined time period.

13. The iris biometric system of claim 7, wherein the second device is a secure device through which a transaction may be conducted.

14. A method comprising authenticating a person to access a first device to transmit a wireless communication to a second device via an iris biometric recognition module comprising program instructions stored in memory and causing one or more processors to execute the steps of:
  aligning a lens of an iris imager device with the iris of the person;
  operating an illuminator device to illuminate the iris;
  operating the iris imager device to produce a digital image of the iris;
  comparing the digital image to a reference iris image; and
  responsive to a determination that the digital image matches the reference iris image:
    authenticating the person as authorized to access the first wireless communication-enabled device, wherein the digital image is a low resolution image selected from a plurality of resolutions, and wherein determining the match comprises selecting a low frequency component corresponding to said low resolution image, said low resolution image and said low frequency component being the lowest sufficient to identify coarse iris features; and
    transmitting the wireless communication from the first device to the second device.

15. The method of claim 14, wherein authenticating the person to access a first device to transmit a wireless communication to a second device via the iris biometric recognition module is executed via the first device incorporating the iris imager device, the illuminator device and the one or more processors.

16. The method of claim 14, wherein:
operating the illuminator device comprises operating an infrared illuminator; and
operating the infrared illuminator comprises illuminating the iris with a pulsing or strobe illumination operation above continuous wave eye safe limits.

17. The method of claim 14, wherein authenticating the person to access a first device to transmit a wireless communication to a second device via the iris biometric recognition module is executed via a mobile device incorporating the iris imager device, the illuminator device and the one or more processors.

18. The method of claim 14, further comprising accessing the reference iris image via wired or wireless internet connectivity, from a local, remote or cloud database.

19. The method of claim 14, further comprising terminating authorization to transmit the wireless communication after a predetermined time period.

20. The method of claim 14, wherein the second device is a secure device through which a transaction may be conducted.

* * * * *